(12) United States Patent
Cook et al.

(10) Patent No.: US 8,268,854 B2
(45) Date of Patent: Sep. 18, 2012

(54) AZA-BETA-CARBOLINES AND METHODS OF USING SAME

(75) Inventors: James M. Cook, Whitefish Bay, WI (US); Michael L. Van Linn, Shorewood, WI (US); Wenyuan Yin, Milwaukee, WI (US)

(73) Assignee: The UWM Research Foundation, Inc., Milwaukee, WI (US)

( * ) Notice: Subject to any disclaimer, the term of this patent is extended or adjusted under 35 U.S.C. 154(b) by 461 days.

(21) Appl. No.: 12/471,019

(22) Filed: May 22, 2009

(65) Prior Publication Data

US 2009/0306121 A1 Dec. 10, 2009

Related U.S. Application Data

(60) Provisional application No. 61/055,334, filed on May 22, 2008.

(51) Int. Cl.
  C07D 471/12 (2006.01)
  A61K 31/437 (2006.01)
(52) U.S. Cl. .............................. 514/290; 546/82; 546/85
(58) Field of Classification Search .................... 546/82, 546/85; 514/290
See application file for complete search history.

(56) References Cited

U.S. PATENT DOCUMENTS

2003/0176456 A1 9/2003 June et al.

FOREIGN PATENT DOCUMENTS

| EP | 0030254 | 6/1981 |
| WO | 2007/085679 | 8/2007 |
| WO | 2008/132454 | 11/2008 |
| WO | 2009/143445 | 11/2009 |

OTHER PUBLICATIONS

Dorwald F. A. Side Reactions in Organic Synthesis, 2005, Wiley: VCH, Weinheim p. IX of Preface.*
Allen, M.S. et al., "Predictive binding of beta-carboline inverse agonists and antagonists via the CoMFA/GOLPE approach," J. Med. Chem. (1992) 35:4001-4010.
Allen, M.S. et al., "Synthesis of novel 3-substituted beta-carbolines as benzodiazepine receptor ligands: probing the benzodiazepine receptor pharmacophore," J. Med. Chem. (1988) 31:1854-1861.
Allen, M.S. et al., "Synthetic and computer-assisted analyses of the pharmacophore for the benzodiazepine receptor inverse agonist site," J. Med. Chem. (1990) 33:2343-2357.
Barberis, C. et al., "Cu(I)-catalyzed intramolecular cyclization of ene-carbamates: synthesis of indoles and pyrrolo [2,3-c] pyridines," Tetrahedron Lett. (2005) 46:8877-8880.
Bedford, R.B. et al., "N-H Carbazole synthesis from 2-chloroanilines via consecutive amination and C-H activation," J. Org. Chem. (2003) 71:9403-9410.
Bell, R.L. et al., "The alcohol-preferring P rat and animal models of excessive alcohol drinking," Addict Biol. (2006) 11:270-288.
Cao, R. et al., "Beta-carboline alkaloids: biochemical and pharmacological functions," Curr. Med. Chem. (2007) 14:279-500.
Choudhary, M.S. et al., "Identification of receptor domains that modify ligand binding to 5-hydroxytryptamine2 and 5-hydroxytryptamine 1c serotonin receptors," Mol. Pharmacol. (1992) 42:627-633.
Cox, E. et al., "Bz1 receptor subtype specific ligands. Synthesis and biological properties of betaCC5, a Bz1 receptor subtype specific antagonist," Med. Chem. Res. (1995) 5:710-718.
Driver, M.S. et al., "A second generation catalyst for aryl halide amination," J. Am. Chem. Soc. (1996) 118:7217-7218.
Estel, L. et al., "Metalation/SRN1 coupling in heterocyclic synthesis. A convenient methodology for ring functionalization," J. Org. Chem. (1988) 53:2740-2744.
Fuchs, K. et al., "Endogenous [3H] flunitrazepam binding in human embryonic kidney cell line 293," Eur. J. Pharmacol. (1995) 289:87-95.
Harvey, S. et al., "The GABA(A) receptor alpha1 subtype in the ventral palladum regulates alcohol-seeking behaviors," J. Neuroscience (2002) 22:3765-3775.
Jonckers, T.H.M. et al., "Synthesis of isocryptolepine via a Pd-catalyzed 'amination-arylation' approach," Synlett. (2003) 615-617.
June, H.L. et al., "The reinforcing properties of alcohol are mediated by GABAA1 receptors in the ventral pallidum," Neuropsychopharmacol. (2003) 28:2124-2137.
Li, X. et al., "Synthesis of optically active tryptophans as IDO inhibitors," Tetrahedron Lett. (2004) 45:8569-8573.
Monguchi, Y. et al., "Pd/C-ET3N-mediated catalytic hydrodechlorination of armatic chlorides under mild conditions," Tetrahedron Lett. (2006) 62:7926-7933.
Namjoshi, O.A. et al., "Development of a two-step route to 3-PBC and betaCCt, two agents active against alcohol self-administration in rodent and primate models," J. Org. Chem. (2011) 76:4721-4727.
Roth, B.L. et al., "5-hydroxytryptamine2 receptors coupled to phospholipase C in rat aorta: modulation of phosphoinositide turnover by phorbol ester," J. Pharmacol. Exp. Ther. (1986) 238:480-485.
Roth, B.L. et al., "Binding of typical and atypical antipsychotic agents to 5-hydroxytryptamine-6 and 5-hydroxytryptamine-7 receptors," J. Pharmacol. Exp. Ther. (1994) 268:1403-1410.
Savic, M. M. et al., "PWZ-029, a compound with moderate inverse agonist functional selectivity at GABAa receptors containing alpha5 subunits, improves passive but not active, avoidance learning in rats," Brain Res. (2008) 1208:150-159.
Sigel, E. et al., "The effect of subunit composition of rat brain GABAa receptors on channel function," Neuron (1990) 5:703-711.
Sigel, E., "Properties of single sodium channels translated by Xenopus oocytes after injection with messenger ribonucleic acid," J. Physiol. (1987) 386:73-90.

(Continued)

Primary Examiner — Rita Desai
(74) Attorney, Agent, or Firm — Michael Best & Friedrich LLP

(57) ABSTRACT

Provided are compounds having the general structure according to Formula (I):

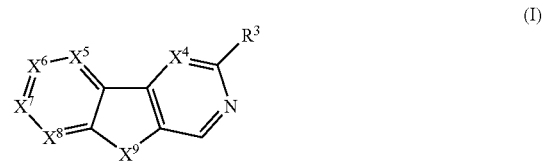

Further provided are pharmaceutical compositions comprising these compounds. The invention still further provides methods of treating alcoholism, methods of reducing alcohol intake, methods of treating anhedonia, and methods of treating anxiety using theses compounds or the compositions containing them.

18 Claims, 21 Drawing Sheets

OTHER PUBLICATIONS

Turner, J.A., "Regiospecific electrophilic substitution of aminopyridines: ortho lithiatiion of 2-, 3-, and 4-(pivaloylamino)pyridines," J. Org. Chem. (1983) 48:3401-3408.

Yin, W. et al., "Search for benzodiazepine/GABA(A) subtype selective ligands that reverse alcohol self-administration," Abstracts of Papers, 224th ACS National Meeting, Boston, MA, Aug. 18-22, 2002, MEDI-244.

Yin, W. et al., "Synthesis of bivalent ligands of beta-carboline-3-carboxylates via a palladium-catalyzed homo-coupling process," Tetrahedron Lett. (2005) 46:6363-6368.

Yin, W., Ph.D. Thesis, "Part II. Design, synthesis and pharmacology of selective ligands for alpha1-containing GABAa/benzodiazepine receptor subtypes. SAR studies of beta-carbolines at positions-3 and -6 and their corresponding bivalent ligands," University of Wisconsin-Milwaukee, Milwaukee, WI (2007) 163-198.

Yu, J. et al., "General approach for the synthesis of sarpagine indole alkaloids. Enantiospecific total synthesis of (+)-vellosimine, (+)-normacusine B, (−)-alkaloid A3, (−)-panarine, (+)-na-methyl-16-epipericyclivine," J. Org. Chem. (2003) 68:7565-7581.

International Search Report and Written Opinion for Application No. PCT/US2009/045014 dated Oct. 29, 2009 (9 pages).

* cited by examiner

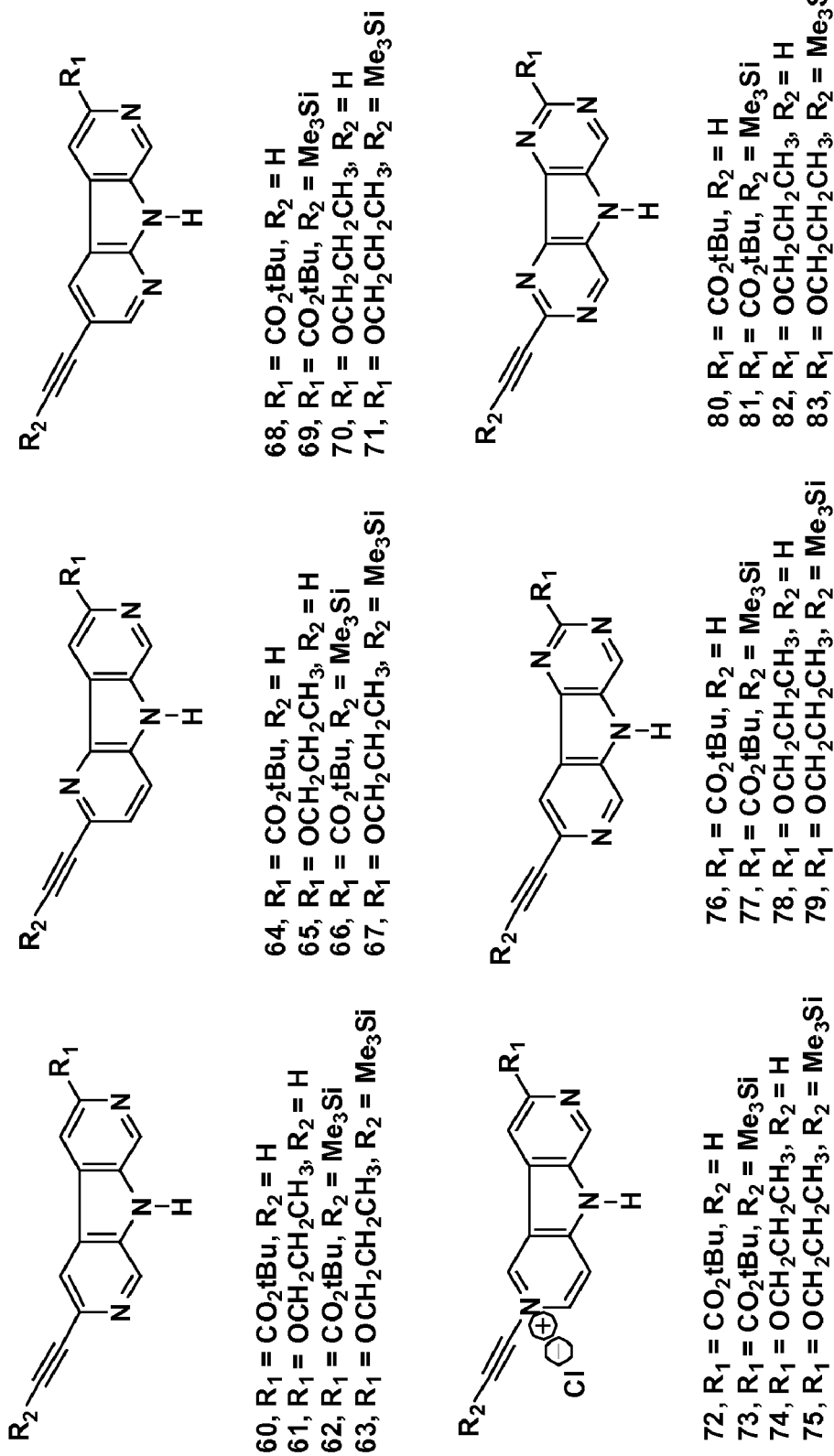
FIG. 2 (1 of 2)

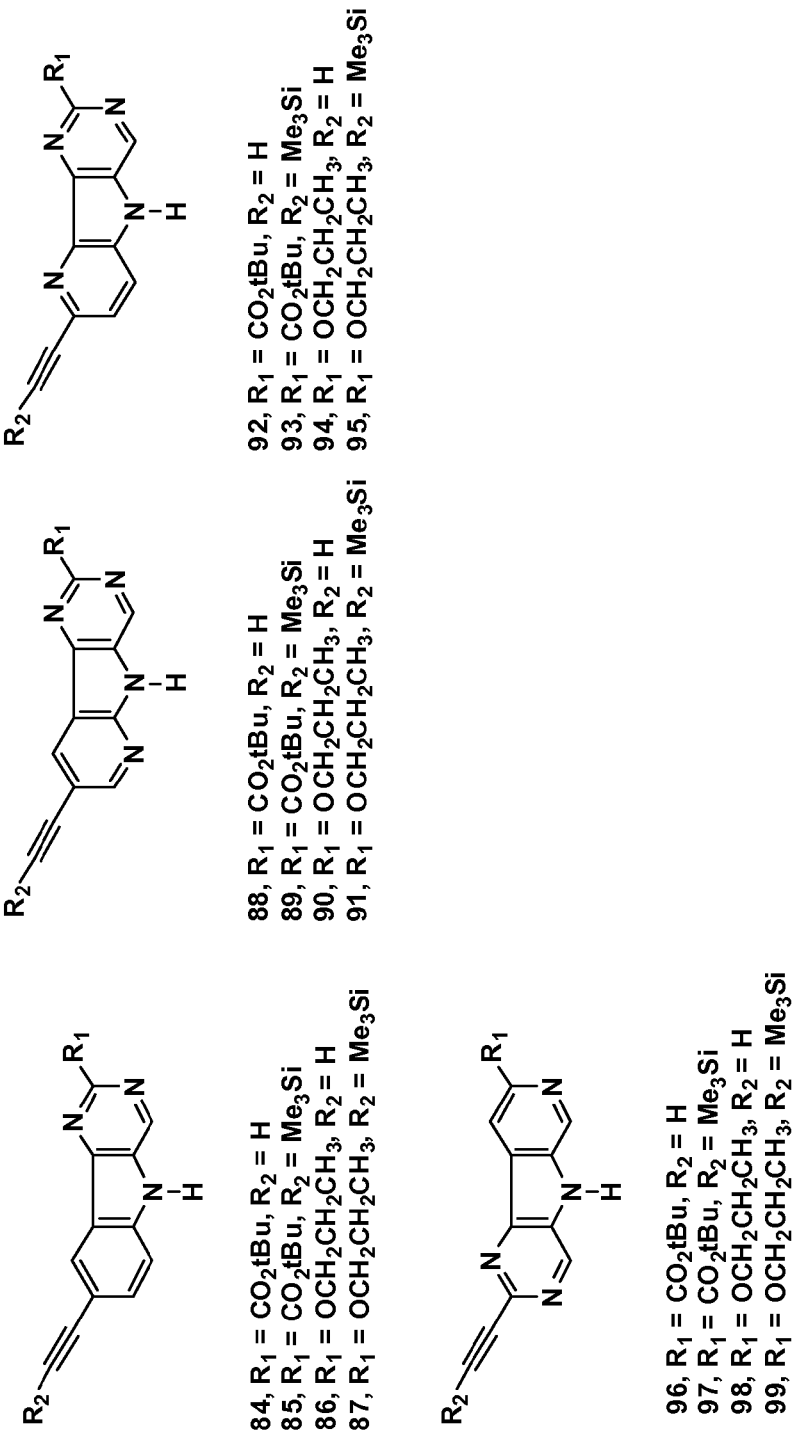
FIG. 2 (2 of 2)

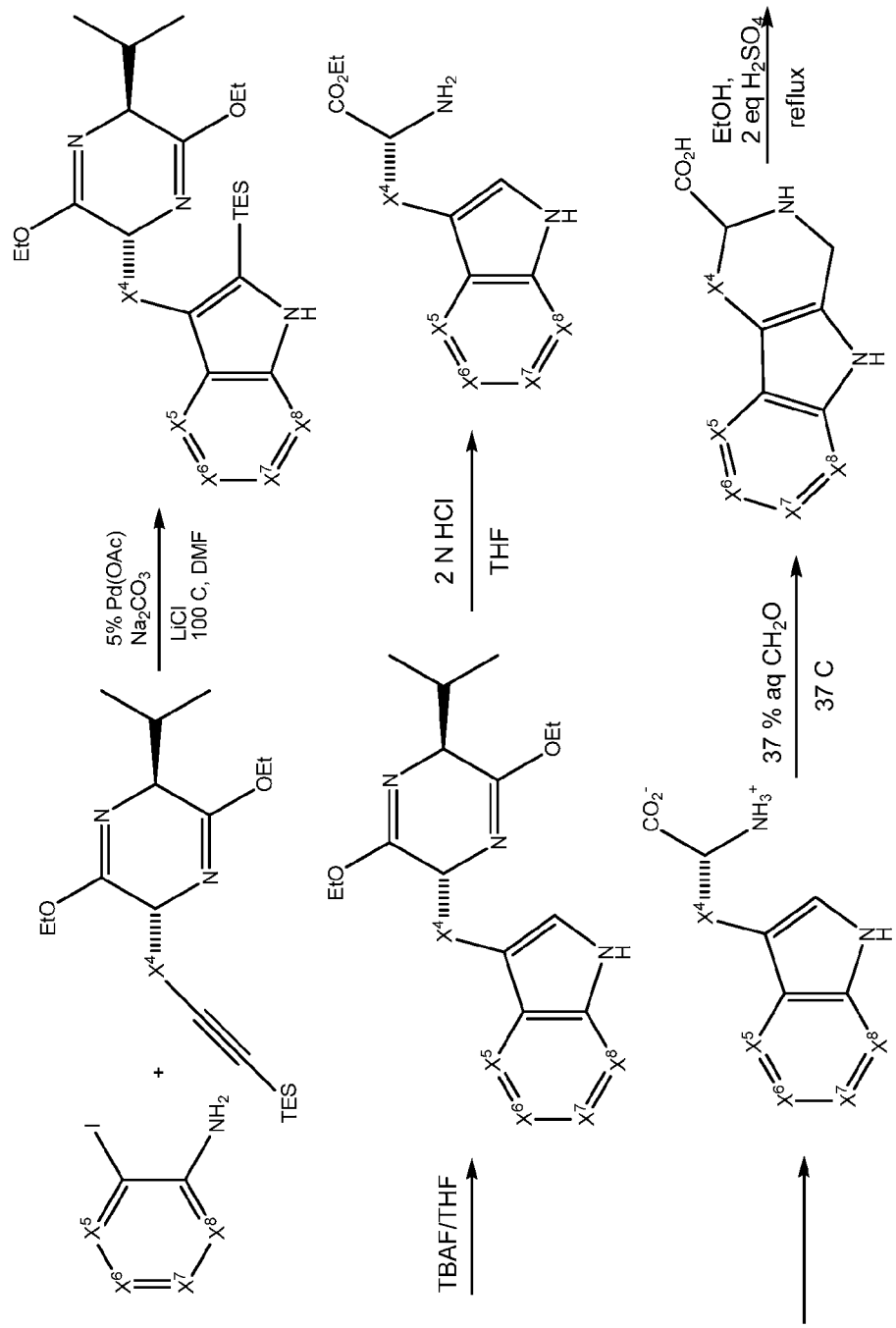
FIG. 3 (1 of 2)

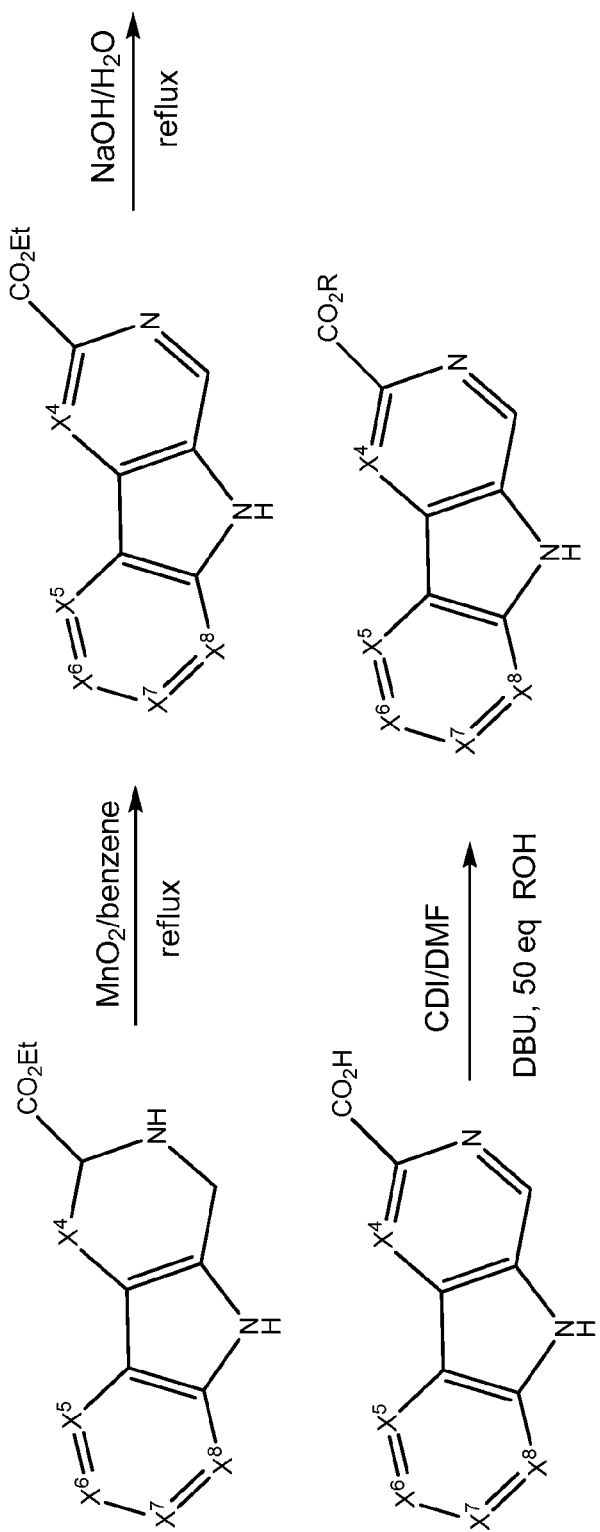
FIG. 3 (2 of 2)
where $X^4$, $X^5$, $X^6$, $X^7$, $X^8$ and R are as defined for Formula (I).

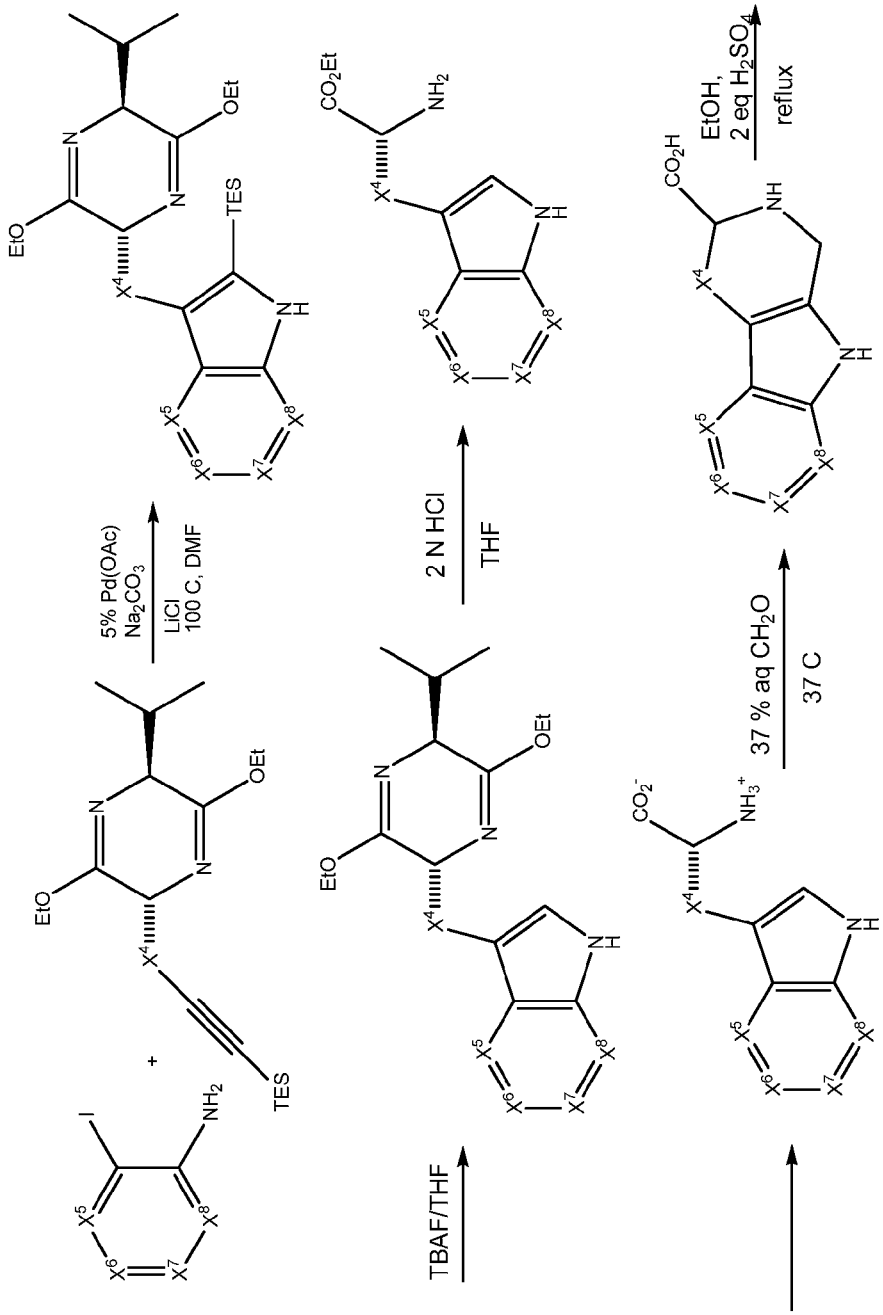
FIG. 4 (1 of 2)

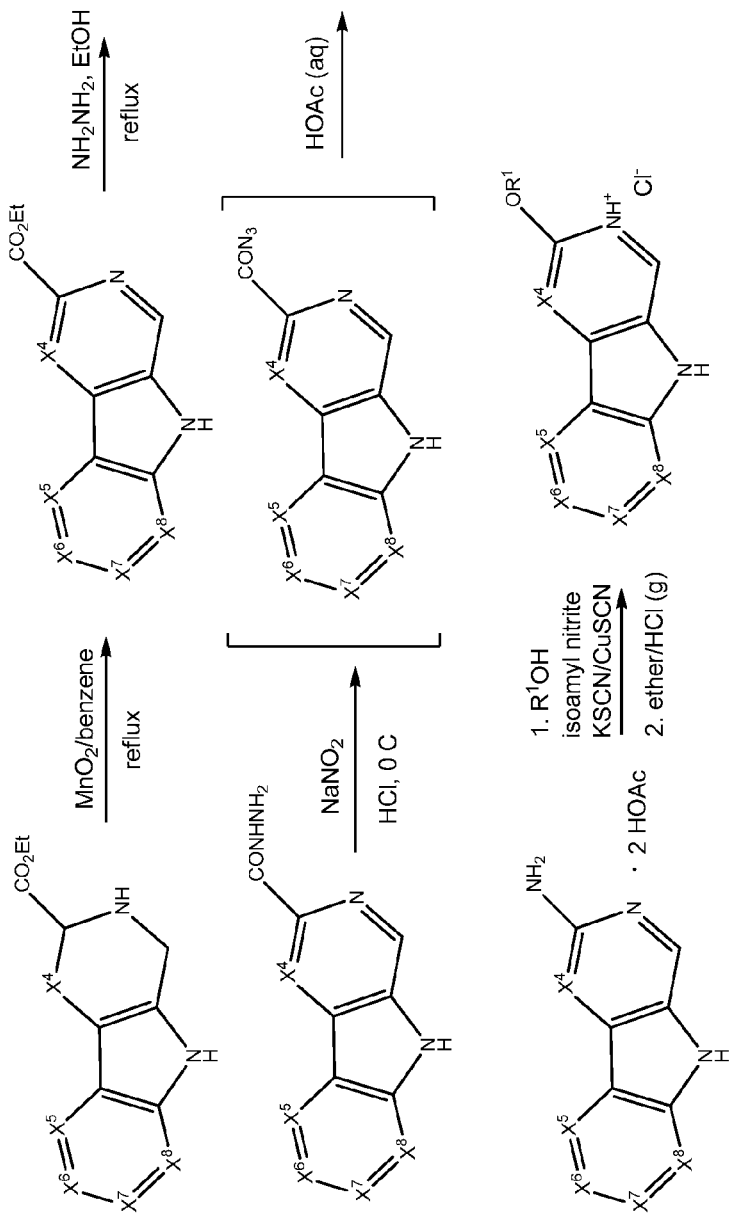
FIG. 4 (2 of 2)

where $X^4$ is CH, and $X^5$, $X^6$, $X^7$, $X^8$ and R are as defined for Formula (I).

where $X^4$, $X^5$, $X^6$, $X^7$, $X^8$ and $R^3$ are as defined for Formula (I).

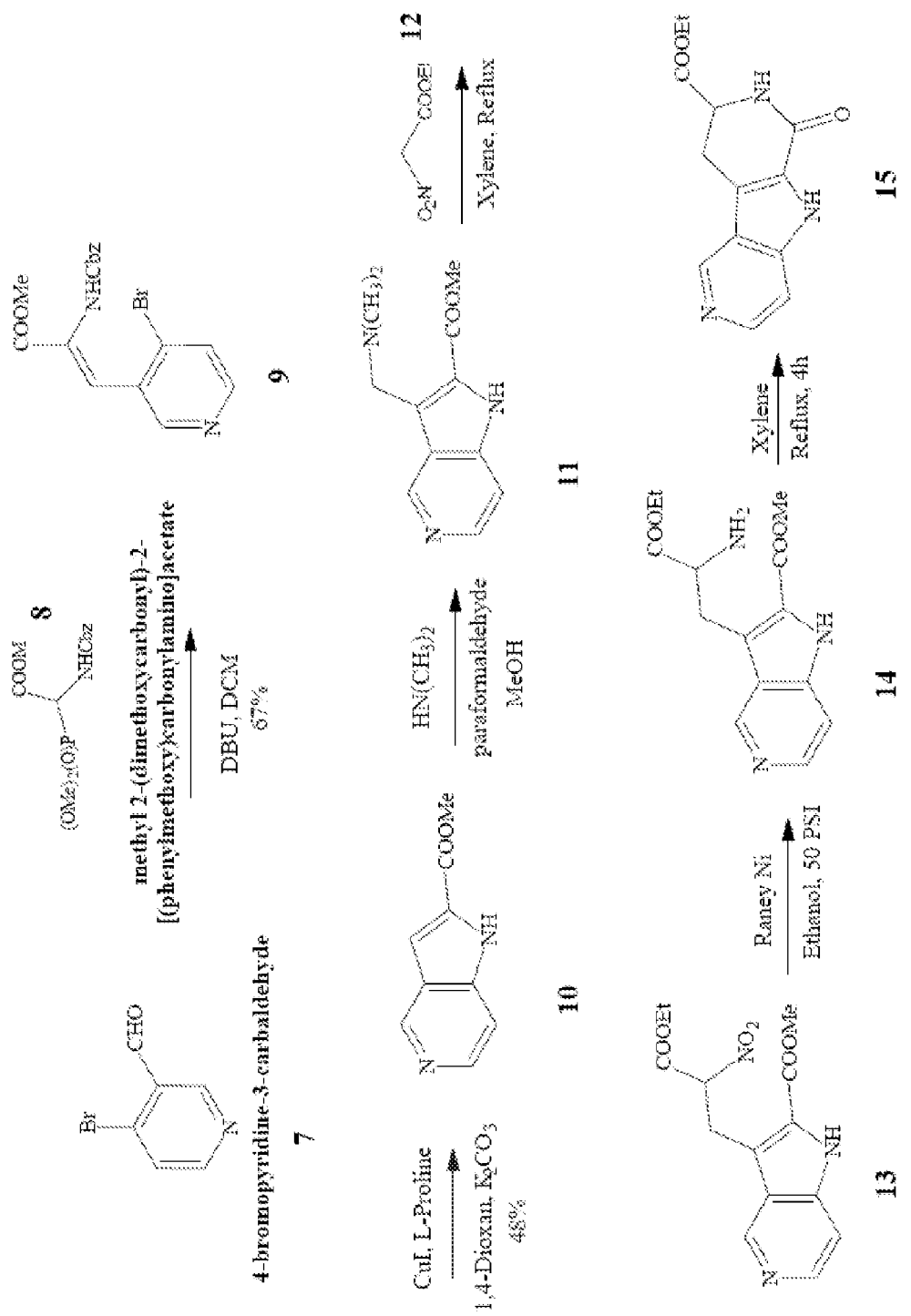
FIG. 7 (1 of 2)

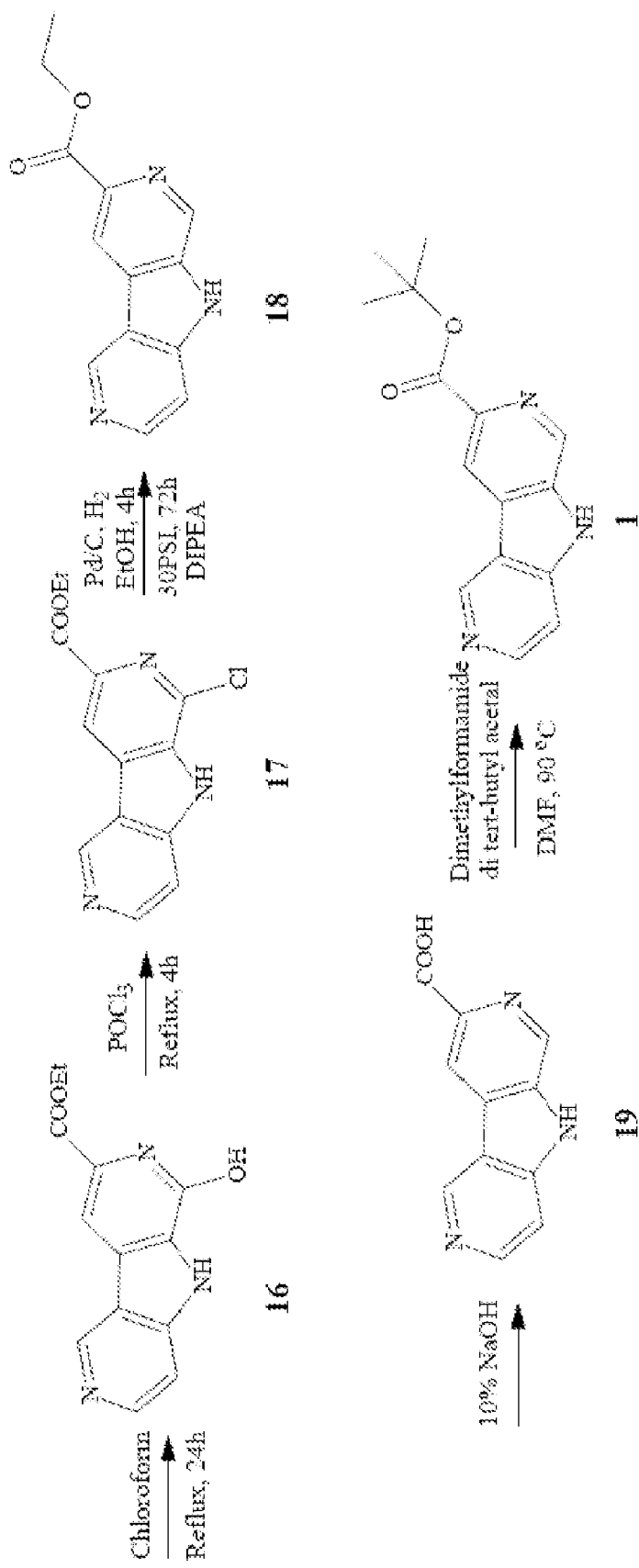
FIG. 7 (2 of 2)

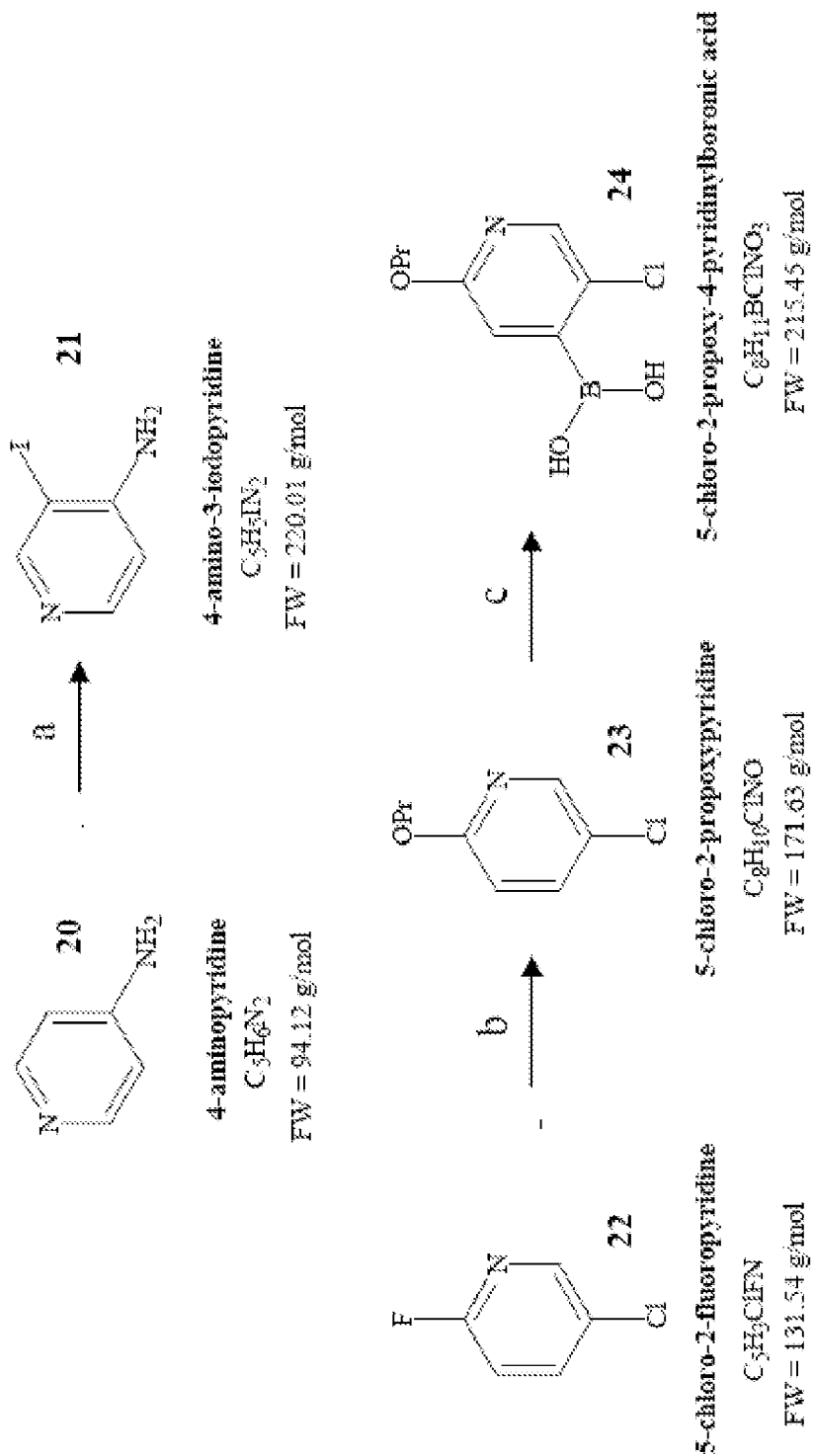
FIG. 8 (1 of 2)

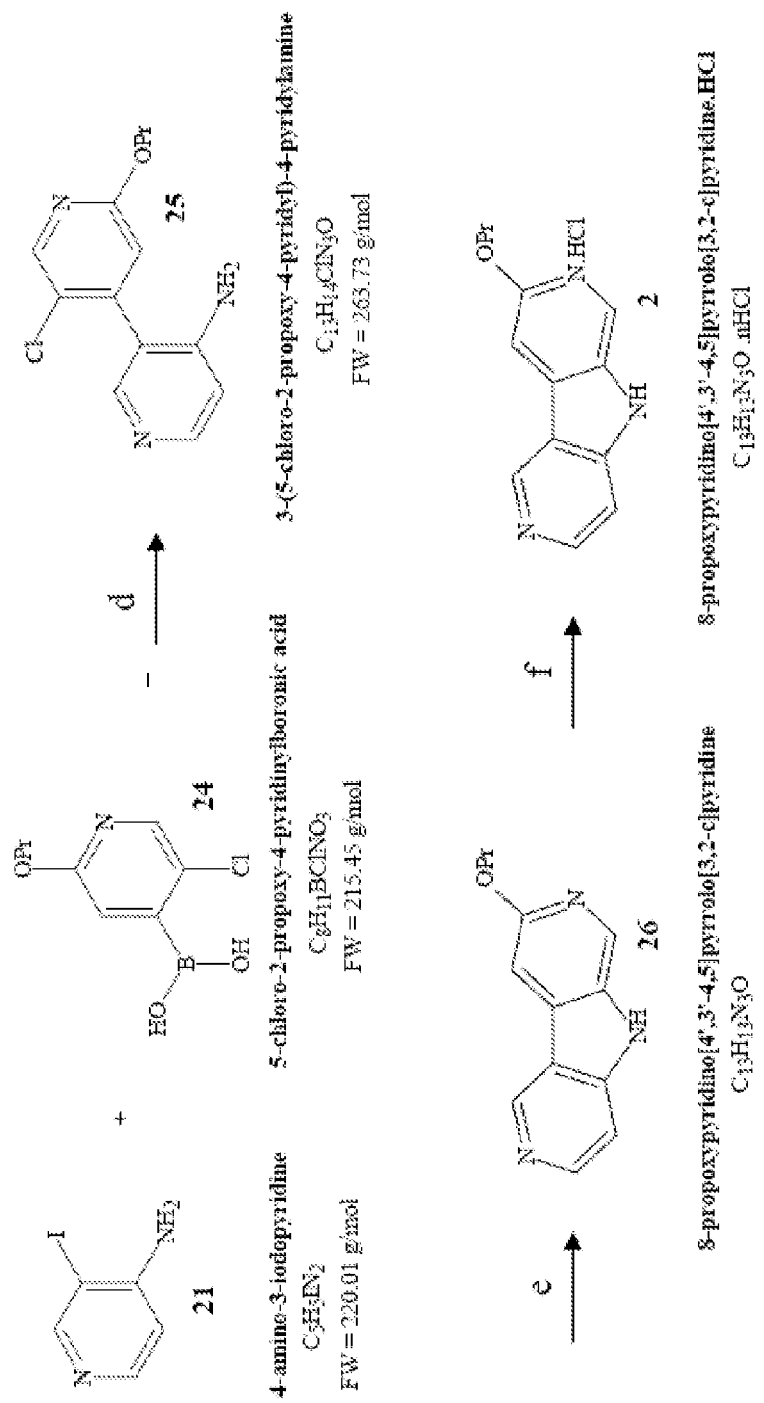
FIG. 8 (2 of 2)

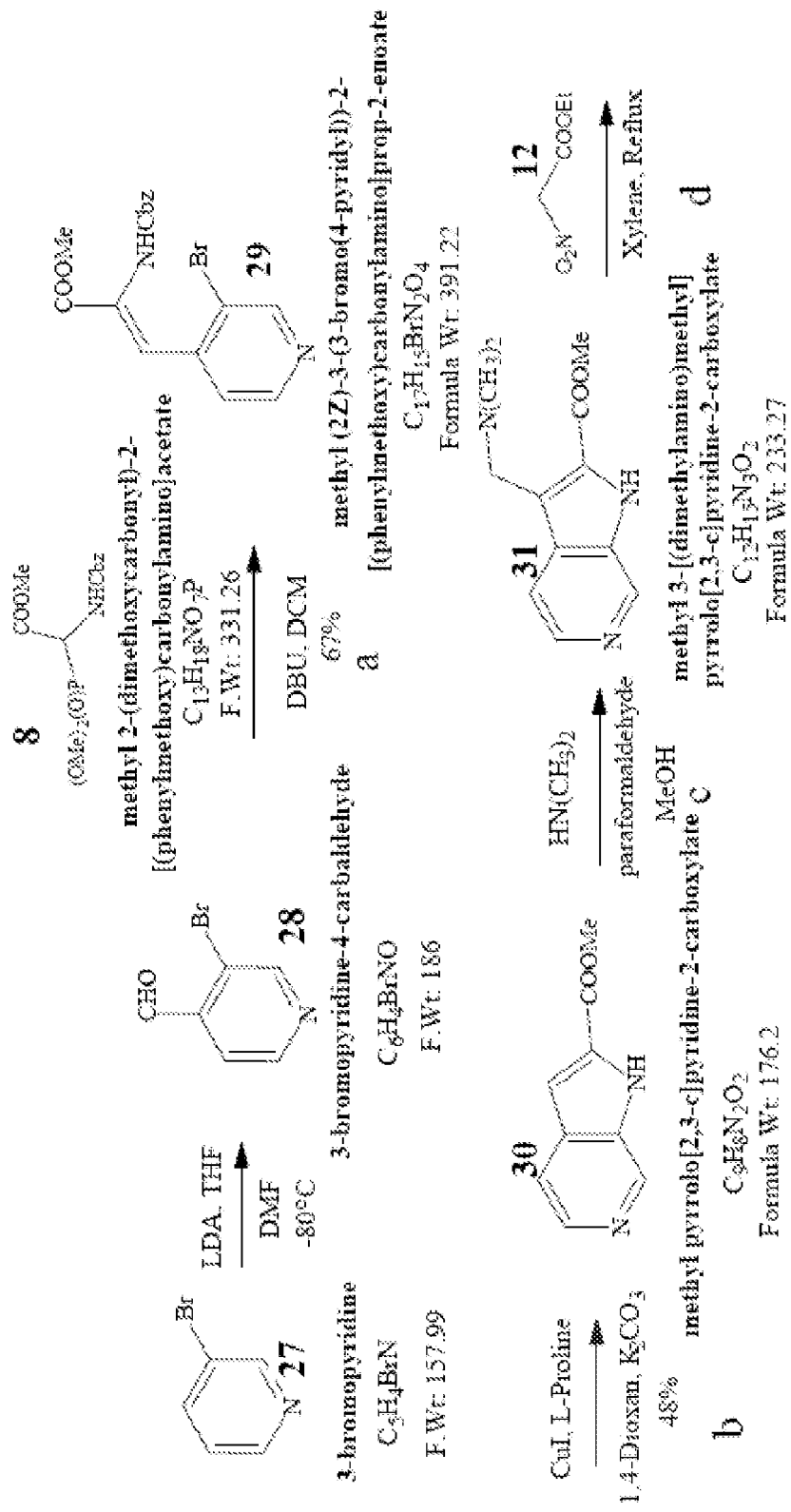
FIG. 9 (1 of 2)

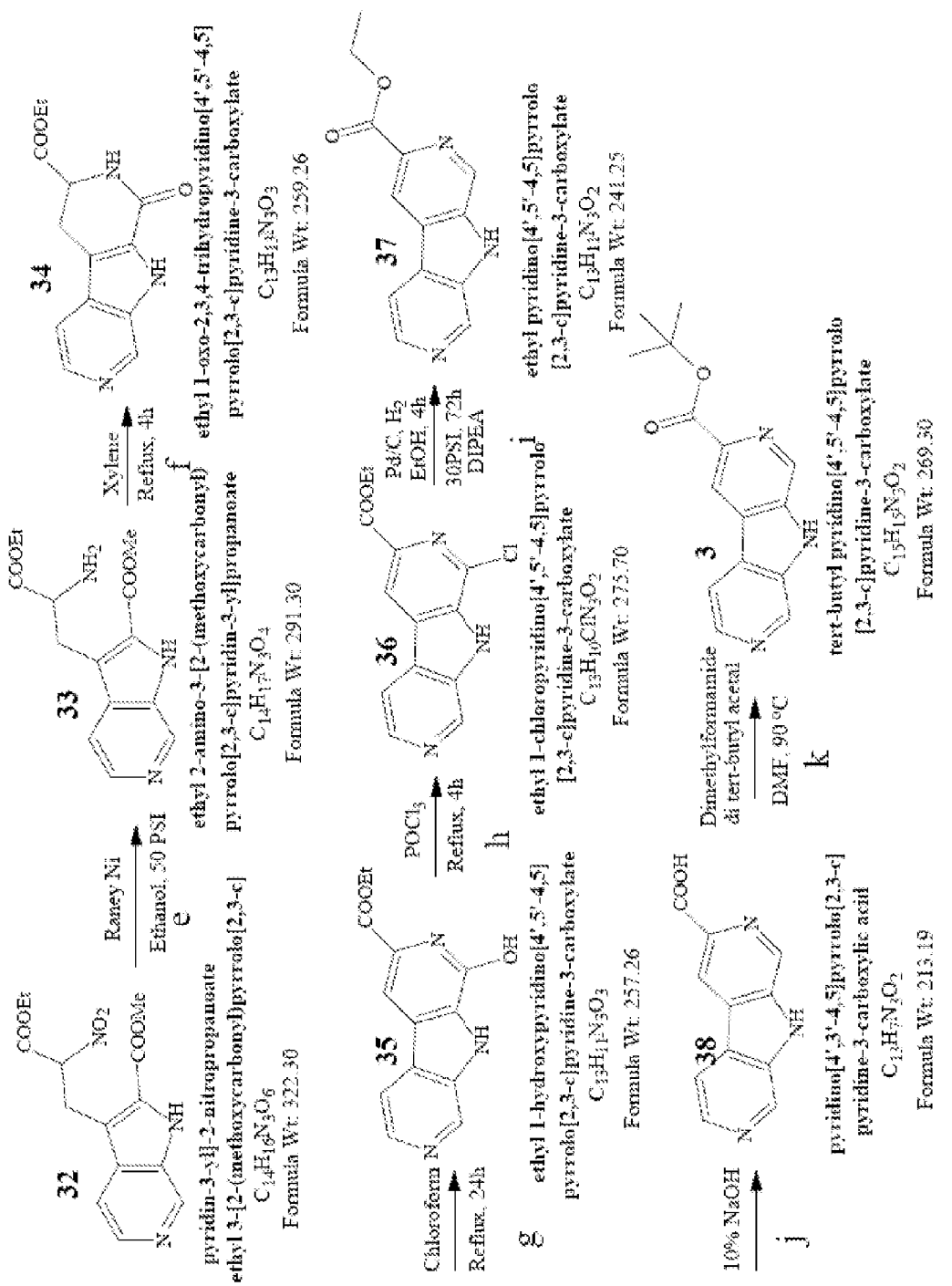
FIG. 9 (2 of 2)

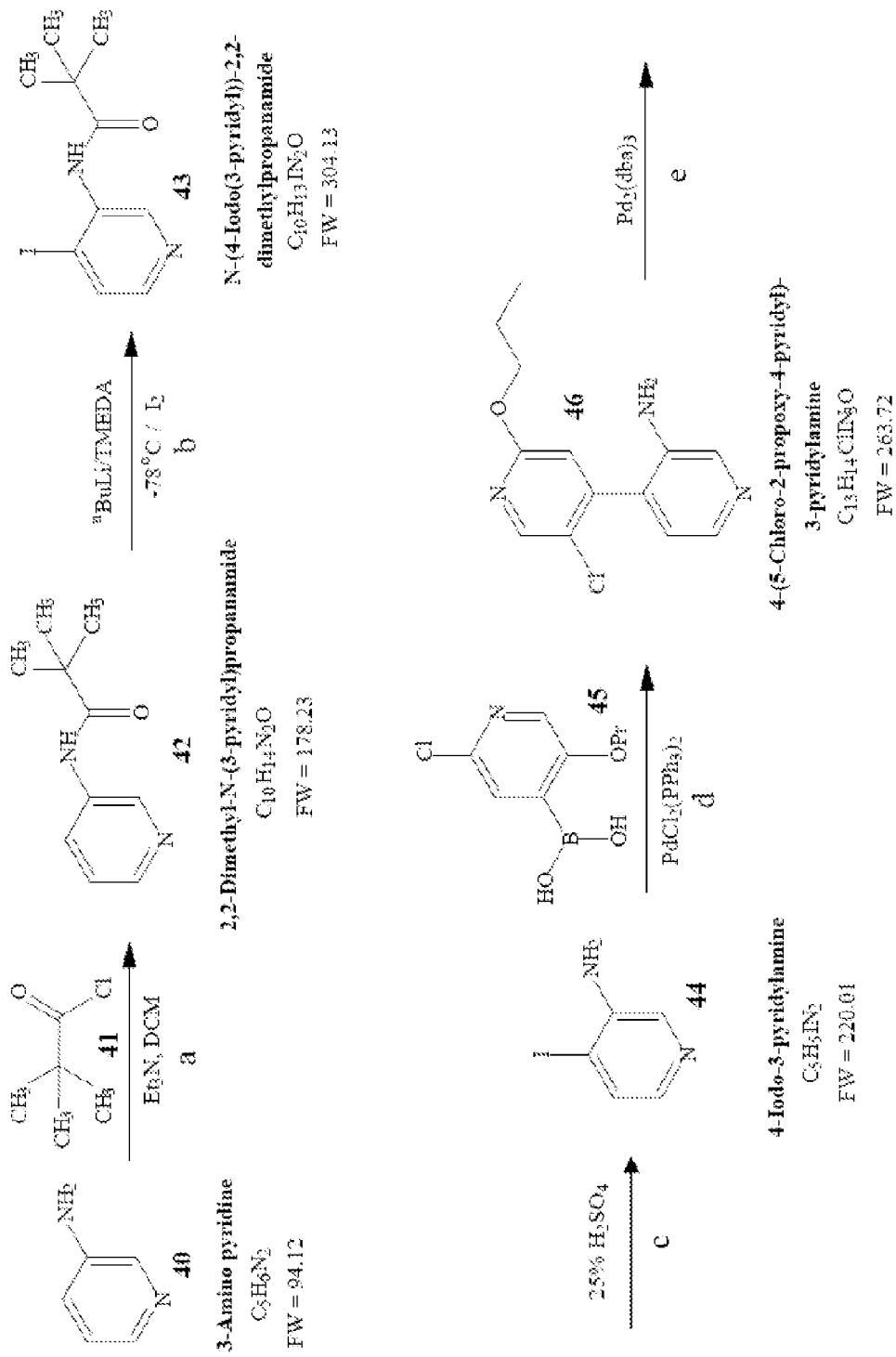
FIG. 10 (1 of 2)

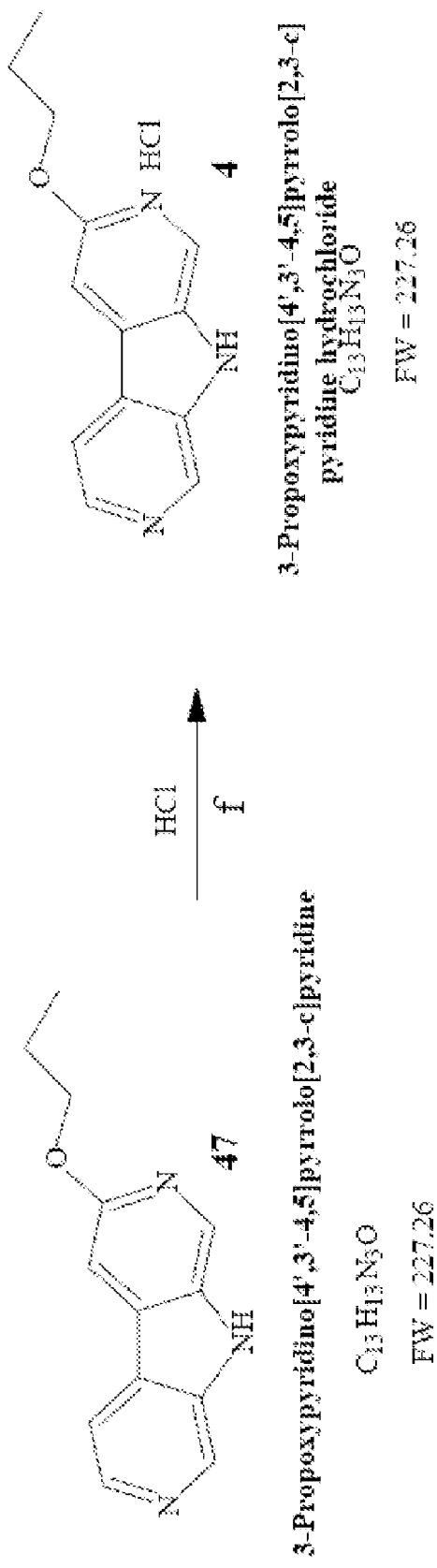
FIG. 10 (2 of 2)

AZA-BETA-CARBOLINES AND METHODS OF USING SAME

CROSS-REFERENCE TO RELATED APPLICATIONS

This application claims the benefit of U.S. Application Ser. No. 61/055,334, filed May 22, 2008, which is incorporated by reference herein.

STATEMENT OF GOVERNMENT SUPPORT

This invention was made with US Government support awarded by National Institute of Mental Health (NIMH), Grant No. MH 46851. The United States has certain rights in this invention.

BACKGROUND OF THE INVENTION

Drug and alcohol addiction and dependence remain a significant public health concern, impacting physical and mental well-being, family structure and occupational stability. While advances have been made in the development of novel therapies to treat alcoholism, alcohol-dependent individuals represent a heterogeneous group, and it is unlikely that a single pharmacological treatment will be effective for all alcoholics. Hence, a better understanding of the neuromechanisms which regulate alcohol seeking behaviors and the design of clinically safe and effective drugs that reduce drug and alcohol addiction and dependence remain a high priority. While the precise neuromechanisms regulating alcohol-seeking behaviors remain unknown, there is now compelling evidence that the $GABA_A$ receptors within the striatopallidal and extended amygdala system are involved in the "acute" reinforcing actions of alcohol. The striatopallidal and extended amygdala system include the sublenticular extended amygdala [substantia innominata-ventral pallidum (VP)], shell of the nucleus accumbens, and central nucleus of the amygdala. Among the potential GABA(A) receptor isoforms within the VP regulating alcohol-seeking behaviors, GABA receptors containing the al receptor subtype ($GABA_{A1}$) appear preeminent. Acute alcohol administration selectively enhanced the effects of ionotophoretically applied GABA in the VP. However, no effects were seen in the septum, VTA, and CA1 of the hippocampus. Further, a positive correlation was observed between alcohol-induced GABA enhancement and [$^3$H] zolpidem binding (an αl subtype selective agonist). A dense reciprocal projection from the VP to the NACC has been identified, and many of these have been found to be GABAergic neurons. The NACC is well established as a substrate that regulates the reinforcing properties of abused drugs. Finally, immunohistochemical and in situ hybridization studies have demonstrated that the VP contains one of the highest concentrations of mRNA encoding the al subunit in the CNS. These findings, together with pharmacological studies suggesting the VP plays a role in reward-mediated behaviors of psychostimulants and opiates suggest a possible role of the VP-al receptors in the euphoric properties of alcohol.

SUMMARY OF THE INVENTION

The present invention relates to compounds having a structure according to Formula (I):

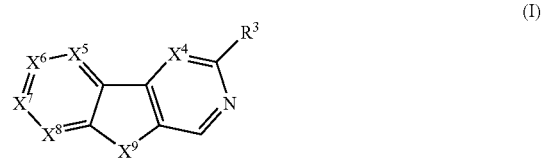

with variables as defined below.

The compounds of the present invention are useful for the treatment of a variety of diseases and conditions such as chemical addiction, e.g. alcoholism, nicotine addiction and opioid addiction, anhedonia, anxiety and other conditions associated with withdrawal from the chemical (e.g. alcohol, nicotine or opioid). Accordingly, the invention further provides pharmaceutical compositions comprising these compounds. The invention still further provides methods of treating chemical addiction, methods of treating alcoholism, methods of reducing alcohol intake, methods of treating anhedonia, and methods of treating anxiety using theses compounds or the compositions containing them.

BRIEF DESCRIPTION OF THE DRAWINGS

FIG. 2 shows various compounds according to the present invention.

FIG. 3 is a scheme to synthesize aza-β-carbolines according to the present invention.

FIG. 4 is a scheme to synthesize aza-β-carbolines according to the present invention.

FIG. 7 is a scheme to synthesize compound 1 according to the present invention.

FIG. 8 is a scheme to synthesize compound 2 according to the present invention.

FIG. 9 is a scheme to synthesize compound 3 according to the present invention.

FIG. 10 is a scheme to synthesize compound 4 according to the present invention.

DETAILED DESCRIPTION OF THE INVENTION

Novel aza-β-carbolines have been developed. These compounds are designed to bind selectively at the α1 subtype GABA receptor and are suitably used as a treatment for alcoholism. The invention also provides methods for reducing alcohol drinking and for reducing the anxiety and anhedonia associated with alcohol drinking and alcohol withdrawal. The invention further provides methods of treating anxiety and/or anhedonia.

Compounds according to the present invention include those shown in Formula (I):

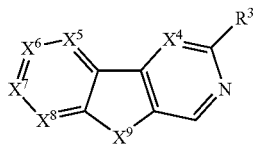

(I)

or isomers, salts, solvates, chemically protected forms or prodrugs thereof;
wherein $X^4$, $X^5$, and $X^8$ may independently be chosen from N or CH, $X^6$ may be N, $^+NR^6$ or $CR^6$, and $X^7$ may be N, $^+NR^6$ or $CR^7$, and wherein no more than any two of $X^5$, $X^6$, $X^7$ and $X^8$ is N;
wherein $X^9$ is NH, O or S;
wherein $R^3$ is $CO_2R$, or $OR^1$ or COR;
wherein $R^6$ and $R^7$ are independently H. X, aryl, heteroaryl, —C≡$CR^2$ lower alkyl, lower alkenyl, or lower alkynyl;
wherein R is —$C(CH_3)_{3-n}(CF_3)_n$, —$C(CH_3)_{3-r}(CH_{3-p}X_p)_r$, —$CH(CH_3)_{2-m}(CF_3)_m$, —$CH(CH_3)_{2-t}(CH_{3-p}X_p)_t$, aryl or heteroaryl;
wherein $R^1$ is —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$CH_2CH_2CH_2CH_2CH_3$, —$CH_2CH_2CH(CH_3)_2$, —$CH_2CH(CH_3)CH_2CH_3$, or —$CH(CH_3)CH_2CH_2CH_3$, wherein any of the hydrogens of $R^1$ may be replaced by X;
wherein $R^2$ is H, lower alkyl, $Me_3Si$, $Et_3Si$, $n$-$Pr_3Si$, $i$-$Pr_3Si$, aryl or heteroaryl;
wherein n is an integer from 0 to 3, m is an integer from 0 to 2, r is an integer from 1 to 3, p is an integer from 1 to 2, and t is an integer from 0 to 2; and
wherein X is independently selected from F, Cl, Br and I.

Figure 1:
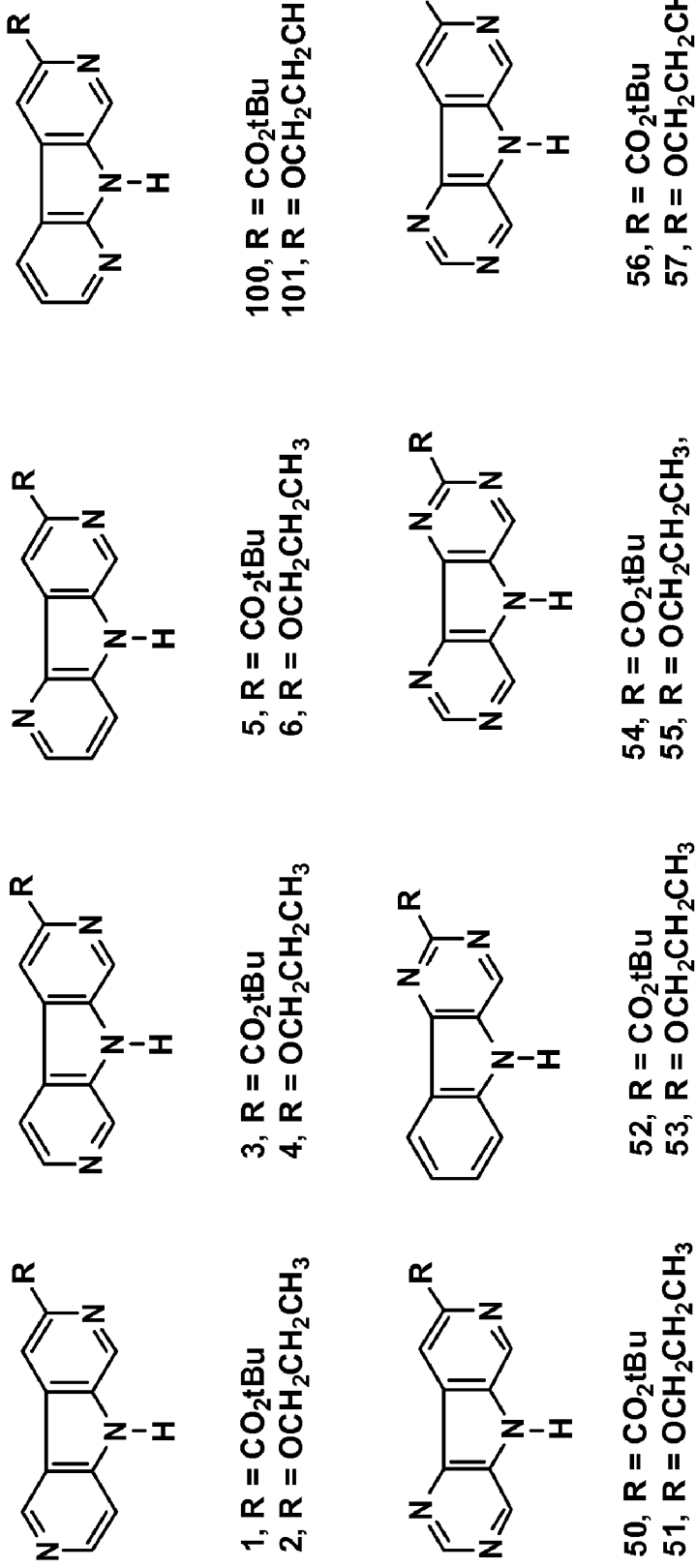
FIG. 1 shows various compounds according to the present invention.

Some compounds according to formula (I) are shown in FIGS. 1-2. Suitably, the compounds of formula (I) bind selectively at the α1 subtype GABA receptor.

DEFINITIONS

Alkyl: The term "alkyl" as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cylcoalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$ alkyl" as used herein, pertains to an alkyl group having from 1 to 4 carbon atoms. Examples of groups of alkyl groups include $C_{1-4}$ alkyl ("lower alkyl"), $C_{1-7}$ alkyl, $C_{1-20}$ alkyl and $C_{1-30}$ alkyl. Note that the first prefix may vary according to other limitations; for example, for unsaturated alkyl groups, the first prefix must be at least 2; for cyclic and branched alkyl groups, the first prefix must be at least 3; etc.

Examples of saturated alkyl groups include, but are not limited to, methyl (C1), ethyl (C2), propyl (C3), butyl (C4), pentyl (C5), hexyl (C6), heptyl (C7), octyl (C8), nonyl (C9), decyl (C10), undecyl (C11), dodecyl (C12), tridecyl (C13), tetradecyl (C14), pentadecyl (C15), and eicodecyl (C20).

Examples of saturated linear alkyl groups include, but are not limited to, methyl (C1), ethyl (C2), n-propyl (C3), n-butyl (C4), n-pentyl (amyl) (C5), n-hexyl (C6), and n-heptyl (C7).

Examples of saturated branched alkyl groups include iso-propyl (C3), iso-butyl (C4), sec-butyl (C4), tert-butyl (C4), iso-pentyl (C5), and neo-pentyl (C5).

Alkenyl: The term "alkenyl" as used herein, pertains to an alkyl group having one or more carbon-carbon double bonds. For example, the term "$C_{2-4}$ alkenyl" as used herein, pertains to an alkenyl group having from 2 to 4 carbon atoms. Examples of groups of alkenyl groups include $C_{2-4}$ alkenyl ("lower alkenyl"), $C_{2-7}$ alkenyl, and $C_{2-20}$ alkenyl.

Examples of alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (1-methylvinyl, —C($CH_3$)=$CH_2$), butenyl (C4), pentenyl (C5), and hexenyl (C6).

Alkynyl: The term "alkynyl" as used herein, pertains to an alkyl group having one or more carbon-carbon triple bonds. For example, the term "$C_{2-4}$ alkynyl" as used herein, pertains to an alkynyl group having from 2 to 4 carbon atoms. Examples of groups of alkynyl groups include $C_{2-4}$ alkynyl ("lower alkynyl"), $C_{2-7}$ alkynyl, and $C_{2-20}$ alkynyl.

Examples of alkynyl groups include, but are not limited to, ethynyl (ethinyl, —C≡CH) and 2-propynyl (propargyl, —$CH_2$—C≡CH).

Aryl: The term "aryl" as used herein, pertains to a monovalent moiety obtained by removing a hydrogen atom from an aromatic ring atom of an aromatic compound, which moiety has from 3 to 10 ring atoms (unless otherwise specified). Preferably, each ring has from 5 to 7 ring atoms.

In this context, the prefixes (e.g. $C_{3-10}$, $C_{5-7}$, $C_{5-6}$, etc.) denote the number of ring atoms, or range of number of ring atoms, whether carbon atoms or heteroatoms. For example, the term "$C_{5-6}$ aryl" as used herein, pertains to an aryl group having 5 or 6 ring atoms. Examples of groups of aryl groups include $C_{3-10}$ aryl, $C_{5-10}$ aryl, $C_{5-7}$ aryl, $C_{5-6}$ aryl, $C_5$ aryl, and $C_6$ aryl.

The ring atoms may be all carbon atoms, as in "carboaryl groups". Examples of carboaryl groups include $C_{3-10}$ carboaryl, $C_{5-10}$ carboaryl, $C_{5-7}$ carboaryl, $C_{5-6}$ carboaryl and $C_6$ carboaryl.

Examples of carboaryl groups include, but are not limited to, those derived from benzene (i.e., phenyl) (C6), naphthalene (C10), and azulene (C10).

Examples of aryl groups which comprise fused rings, at least one of which is an aromatic ring, include, but are not limited to, groups derived from indane (e.g., 2,3-dihydro-1H-indene) (C9), indene (C9), isoindene (C9), and tetraline (1,2,3,4-tetrahydronaphthalene (C10).

Alternatively, the ring atoms may include one or more heteroatoms, as in "heteroaryl groups". Examples of heteroaryl groups include $C_{3-10}$ heteroaryl, $C_{5-10}$ heteroaryl, $C_{5-7}$ heteroaryl, $C_{5-6}$ heteroaryl, $C_5$ heteroaryl, and $C_6$ heteroaryl.

Examples of monocyclic heteroaryl groups include, but are not limited to, those derived from:
N1: pyrrole (azole) (C5), pyridine (azine) (C6);
O1: furan (oxole) (C5);
S1: thiophene (thiole) (C5);
N1O1: oxazole (C5), isoxazole (C5), isoxazine (C6);
N2O1: oxadiazole (furazan) (C5);
N3O1: oxatriazole (C5);

N1S1: thiazole (C5), isothiazole (C5);

N2: imidazole (1,3-diazole) (C5), pyrazole (1,2-diazole) (C5), pyridazine (1,2-diazine) (C6), pyrimidine (1,3-diazine) (C6) (e.g., cytosine, thymine, uracil), pyrazine (1,4-diazine) (C6);

N3: triazole (C5), triazine (C6); and,

N4: tetrazole (C5).

Examples of heteroaryl groups which comprise fused rings, include, but are not limited to:

C9 heteroaryl groups (with 2 fused rings) derived from benzofuran (O1), isobenzofuran (O1), indole (N1), isoindole (N1), indolizine (N1), indoline (N1), isoindoline (N1), purine (N4) (e.g., adenine, guanine), benzimidazole (N2), indazole (N2), benzoxazole (N1O1), benzisoxazole (N1O1), benzodioxole (O2), benzofurazan (N2O1), benzotriazole (N3), benzothiofuran (S1), benzothiazole (N1S1), benzothiadiazole (N2S);

C10 heteroaryl groups (with 2 fused rings) derived from chromene (O1), isochromene (O1), chroman (O1), isochroman (O1), benzodioxan (O2), quinoline (N1), isoquinoline (N1), quinolizine (N1), benzoxazine (N1O1), benzodiazine (N2), pyridopyridine (N2), quinoxaline (N2), quinazoline (N2), cinnoline (N2), phthalazine (N2), naphthyridine (N2), pteridine (N4);

C11 heteroaryl groups (with 2 fused rings) derived from benzodiazepine (N2);

C13 heteroaryl groups (with 3 fused rings) derived from carbazole (N1), dibenzofuran (O1), dibenzothiophene (S1), carboline (N2), perimidine (N2), pyridoindole (N2); and, C14 heteroaryl groups (with 3 fused rings) derived from acridine (N1), xanthene (O1), thioxanthene (S1), oxanthrene (O2), phenoxathiin (O1S1), phenazine (N2), phenoxazine (N1O1), phenothiazine (N1S1), thianthrene (S2), phenanthridine (N1), phenanthroline (N2), phenazine (N2).

Heteroaryl groups which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$ alkyl, $C_{3-20}$ heterocyclyl, $C_{5-20}$ aryl, and acyl groups.

Heterocyclic groups (including heteroaryl groups) which have a nitrogen ring atom in the form of an —N═ group may be substituted in the form of an N-oxide, that is, —N(→O)═ (also denoted —N+(→O—)═). For example, quinoline may be substituted to give quinoline N-oxide; pyridine to give pyridine N-oxide; benzofurazan to give benzofurazan N-oxide (also known as benzofuroxan).

The above groups, whether alone or part of another substituent, may themselves optionally be substituted with one or more groups selected from themselves and the additional substituents listed below.

Halo: —F, —Cl, —Br, and —I.

Hydroxy: —OH.

Ether: —OR, wherein R is an ether substituent, for example, a $C_{1-7}$ alkyl group (also referred to as a $C_{1-7}$ alkoxy group, discussed below), a $C_{3-20}$ heterocyclyl group (also referred to as a $C_{3-20}$ heterocyclyloxy group), or a $C_{5-20}$ aryl group (also referred to as a $C_{5-20}$ aryloxy group), preferably a $C_{1-7}$ alkyl group.

Alkoxy: —OR, wherein R is an alkyl group, for example, a $C_{1-7}$ alkyl group. Examples of $C_{1-7}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Oxo (keto, -one): ═O.

Acyl (keto): —C(═O)R, wherein R is an acyl substituent, for example, a $C_{1-7}$ alkyl group (also referred to as $C_{1-7}$ alkylacyl or $C_{1-7}$ alkanoyl), a $C_{3-20}$ heterocyclyl group (also referred to as $C_{3-20}$ heterocyclylacyl), a $C_{5-20}$ aryl group (also referred to as $C_{5-20}$ arylacyl), preferably a $C_{1-7}$ alkyl group or a halo. Examples of acyl groups include, but are not limited to, —C(═O)CH$_3$ (acetyl), —C(═O)CH$_2$CH$_3$ (propionyl), —C(═O)C(CH$_3$)$_3$ (t-butyryl), —C(═O)Ph (benzoyl, phenone), —C(═O)Cl.

Carboxy (carboxylic acid): —C(═O)OH.

Ester (carboxylate, carboxylic acid ester, oxycarbonyl): —C(═O)OR, wherein R is an ester substituent, for example, a $C_{1-7}$ alkyl group, a $C_{3-20}$ heterocyclyl group, or a $C_{5-20}$ aryl group, preferably a $C_{1-7}$ alkyl group. Examples of ester groups include, but are not limited to, —C(═O)OCH$_3$, —C(═O)OCH$_2$CH$_3$, —C(═O)OC(CH$_3$)$_3$, and —C(═O)OPh.

Amino: —NR$_2$, wherein each R is independently an amino substituent, for example, hydrogen, a $C_{1-7}$ alkyl group (also referred to as $C_{1-7}$ alkylamino or di-$C_{1-7}$ alkylamino), a $C_{3-20}$ heterocyclyl group, or a $C_{5-20}$ aryl group, preferably H or a $C_{1-7}$ alkyl group, or, in the case of a "cyclic" amino group, both R's, taken together with the nitrogen atom to which they are attached, form a heterocyclic ring having from 4 to 8 ring atoms. Amino groups may be primary (—NH$_2$), secondary (—NHR), or tertiary (—NR$_2$), and in cationic form, may be quaternary (—+NR$_3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Amido (carbamoyl, carbamyl, aminocarbonyl, carboxamide): —C(═O)NR$_2$, wherein each R is independently an amino substituent, as defined for amino groups. Examples of amido groups include, but are not limited to, —C(═O)NH$_2$, —C(═O)NHCH$_3$, —C(═O)N(CH$_3$)$_2$, —C(═O)NHCH$_2$CH$_3$, and —C(═O)N(CH$_2$CH$_3$)$_2$, as well as amido groups in which both R's, together with the nitrogen atom to which they are attached, form a heterocyclic structure as in, for example, piperidinocarbonyl, morpholinocarbonyl, thiomorpholinocarbonyl, and piperazinocarbonyl.

Cyano (nitrile, carbonitrile): —CN.

Alkylsilyl groups: —SiR$_3$, wherein each R is independently an alkyl group. Suitably the alkyl groups are lower alkyl groups such as methyl, ethyl or propyl.

Isomers, Salts, Solvates, Protected Forms, and Prodrugs

Certain compounds may exist in one or more particular geometric, optical, enantiomeric, diasterioisomeric, epimeric, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

If the compound is in crystalline form, it may exist in a number of different polymorphic forms.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$ alkyl includes n-propyl and isopropyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol, imine/enamine, amide/imino alcohol, amidine/amidine, nitroso/oxime, thioketone/enethiol, N-nitroso/hyroxyazo, and nitro/aci-nitro.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

It may be convenient or desirable to prepare, purify, and/or handle the active compound in the form of a prodrug. The term "prodrug", as used herein, pertains to a compound which, when metabolised (e.g. in vivo), yields the desired active compound. Typically, the prodrug is inactive, or less active than the active compound, but may provide advantageous handling, administration, or metabolic properties.

It may be convenient or desirable to prepare, purify, and/or handle the active compound in the form of a salt. Suitable salts include those commonly used for pharmaceuticals, such as the hydrochloride salt.

Synthesis

Aza-β-carbolines according to the present invention can be prepared by the chemistry outlined in FIGS. 3-4. In brief, an aza-iodoaniline is reacted with an acetylene substituted Schöllköpf chiral auxiliary in the presence of a palladium catalyst to provide an aza indole. The triethylsilyl group is removed by stirring with TBAF followed by hydrolysis to provide an aza-tryptophan ethyl ester. This ester is reacted with formaldehyde and then converted to the desired aza-β-carboline as shown in FIGS. 3-4. See e.g., W. Yin, P. V. V. S. Sarma, J. Ma, D. Han, J. Chen and J. M. Cook, Synthesis of Bivalent Ligands of β-Carboline-3-Carboxylates via a Palladium-Catalyzed Homo-Coupling Process, *Tetrahedron Lett.*, 46, 6363-6368 (2005), which is incorporated by reference herein; E. Cox, T. Hagen, R. McKernan and J. M. Cook, Bz1 Receptor Subtype Specific Ligands. Synthesis and Biological Properties of βCCt, a Bz1 Receptor Subtype Specific Antagonist, *Med. Chem. Res.*, 5, 710-718 (1995), which is incorporated by reference herein; M. S. Allen, T. J. Hagen, M. L. Trudell, P. Skolnick and J. M. Cook, Synthesis of Novel 3-Substituted β-Carbolines as Benzodiazepine Receptor Ligands: Probing the Benzodiazepine Receptor Inverse Agonist Site," *J. Med. Chem.*, 31, 1854-1861 (1988), which is incorporated by reference herein; S. Harvey, K. Foster, P. McKay, M. Carroll, R. Seyoum, J. E. Woods II, C. Grey, C. Jones S. McCane, R. Cummings, D. Mason, C. Ma, J. M. Cook, and H. June, The GABA(A) Receptor α1 Subtype in the Ventral Pallidum Regulates Alcohol-Seeking Behaviors, *J. Neuroscience*, 22, 3765-3775 (2002), which is incorporated by reference herein; W. Yin, X. Liao, H. June and J. M. Cook, Search for Benzodiazepine/GABA(A) Subtype Selective Ligands that Reverse Alcohol Self-Administration, Abstracts of Papers, 224$^{th}$ ACS National Meeting, Boston, Mass., August 18-22 (2002), MEDI-244, which is incorporated by reference herein; and H. June, C. Ma and J. M. Cook, Methods for Reducing Alcohol Cravings in Chronic Alcoholics, US Patent Application Publication No. US2003/0176456A1, Sep. 18, 2003; which is incorporated by reference herein.

Figure 5:
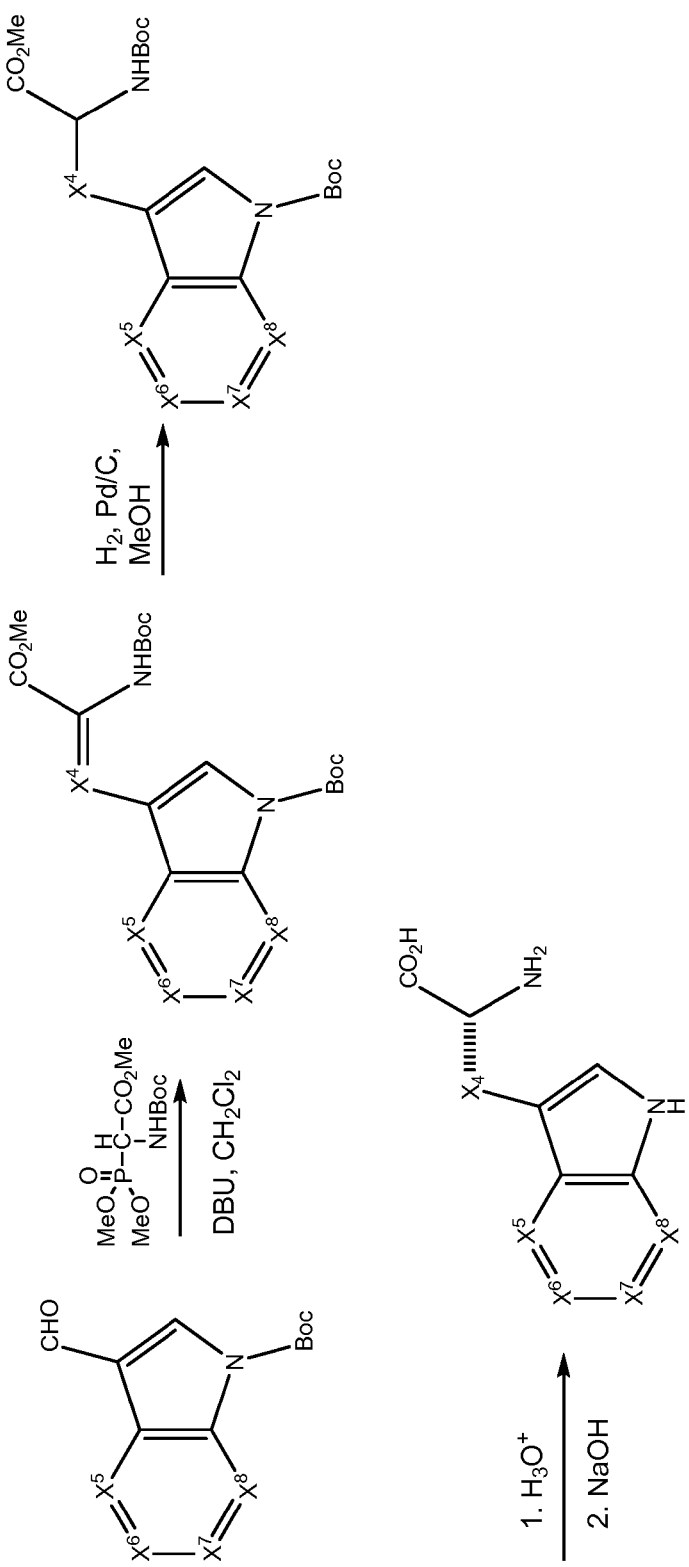
FIG. 5 is a scheme to synthesize aza-tryptophans according to the present invention.

The aza-tryptophans used in the above synthesis can also be synthesized by the route shown in FIG. 5. A Boc-protected formyl-azaindole is reacted with a Wadsworth Horner Emmons reagent in the presence of DBU to provide an aza-indole olefin. Reduction of the double bond, followed by hydrolysis provides an aza-tryptophan, set up for the steps depicted in FIGS. 3-4. See, e.g. X. Li, W. Yin, P. V. V. S. Sarma, H. Zhao, J. Ma and J. M. Cook, "Synthesis of Optically Active Tryptophas as IDO Inhibitors," *Tet. Lett.*, 45, 8569-8573 (2004), which is incorporated by reference herein; and J. Yu, T. Wang, X. Liu, J. Deschamps, J. Flippen-Anderson, X. Liao, J. M. Cook, "General Approach for the Synthesis of Sarpagine Indole Alkaloids. Enantiospecific Total Synthesis of (+)-Vellosimine, (+)-Normacusine B, (−)-Alkaloid Q3, (−)-Panarine, (+)-N$_2$-Methylvellosimine, and (+)-N$_a$-Methyl-16-epipericyclivine," *J. Org. Chem.*, 68, 7565-7581 (2003), which is incorporated by reference herein.

Figure 6:
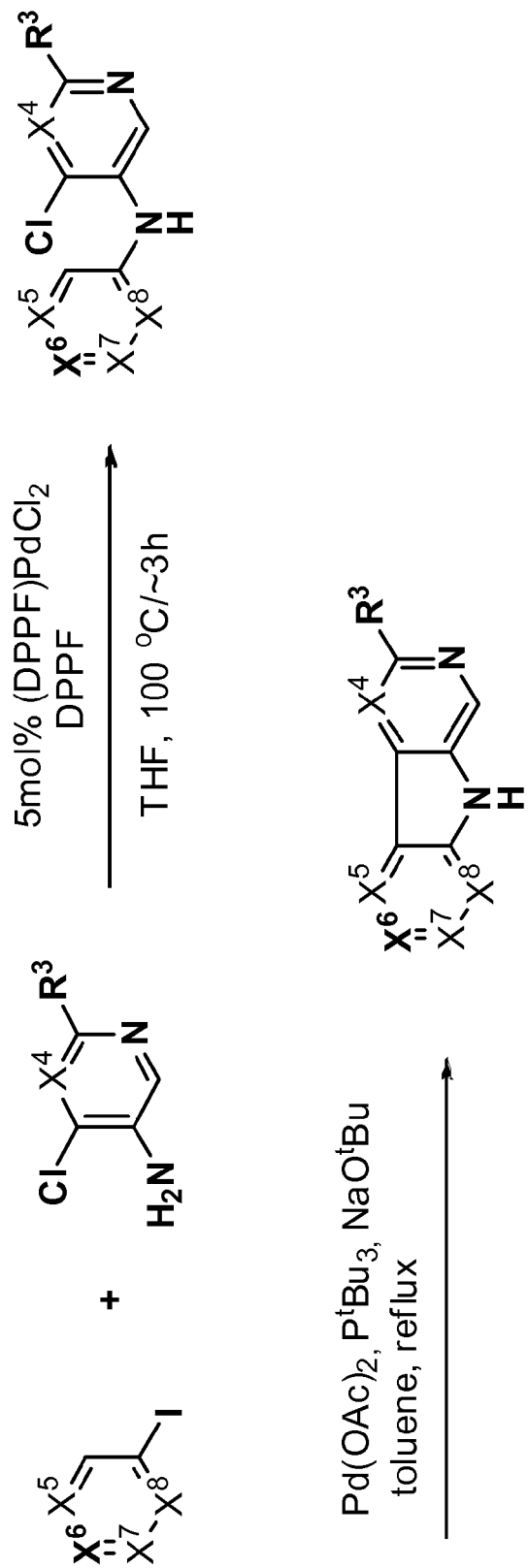
FIG. 6 is a scheme for Pd-mediated synthesis of aza-β-carbolines.

Aza-β-carbolines according to the present invention can also be prepared via a Pd-mediated synthesis shown presented in FIG. 6 In brief, an iodopyridine will be reacted with a 4-chloro, 5-amino pyridine in the presence of a Buchwald-Hartwig amination catalyst to provide bipyridyl analog. This amine will be subjected to a Buchwald-type coupling process with the chloride to generate the desired aza-β-carboline. See, e.g., Driver, M. S, and Hartwig, J. F. A Second-Generation Catalyst for Aryl Halide Amination, J. Am. Chem. Soc., 118, 7217-7218 (1996), which is incorporated by reference herein; Bedford, R. B. and Betham, M. N—H Carbazole Synthesis from 2-Chloroanilines via Consecutive Amination and C—H Activation, J. Org. Chem. 71, 9403-9410 (2006), which is incorporated by reference herein; and Jonckers, T. et al. Syn. Lett., 615-617 (2003), which is incorporated by reference herein.

Activity

In one embodiment, the present invention provides a method of treating chemical addiction comprising administering a therapeutically effective amount of a compound of formula (I) to a subject in need thereof. In some embodiments, the chemical may be alcohol, nicotine or opioids. In a further embodiment, the present invention provides a method of reducing chemical intake comprising administering a therapeutically effective amount of a compound of formula (I) to a subject in need thereof.

In another embodiment, the present invention provides a method of treating alcoholism comprising administering a therapeutically effective amount of a compound of formula (I) to a subject in need thereof. In another embodiment, the present invention provides a method for reducing alcohol intake comprising administering a therapeutically effective amount of a compound of formula (I) to a subject in need thereof.

In a further embodiment, the present invention provides a method for reducing anxiety comprising administering a therapeutically effective amount of a compound of formula (I) to a subject in need thereof. In yet another embodiment, the present invention provides a method of treating anhedonia comprising administering a therapeutically effective amount of a compound of formula (I) to a subject in need thereof. In some embodiments, the anxiety and/or anhedonia is associated with chemical withdrawal or reducing chemical intake.

In yet another embodiment, the invention provides a method of reducing physical symptoms (e.g., tremors and seizures) associated with chemical withdrawal comprising administering a therapeutically effective amount of a compound according to formula (I) to a subject in need thereof.

The compounds of formula (I) may be administered alone or in combination with other active compounds, for example, those known to be useful in treating chemical addiction or alcoholism or anxiety or anhedonia, such as anxiolytics (e.g. diazepam, clonazepam, clorazepate, alprazolam, buspirone, and meprobamate), or alcoholism treatments (e.g. naltrexone, naltrexone hydrochloride, disulfuram, nalmefene, metadoxine, acamposate calcium, and chlordiazepoxide hydrochloride). If administered in combination, the additional active compound can be administered simultaneously or sequentially with the compound of formula (I). In some embodiments, the additional active compound can be administered before or after the compound of formula (I).

$GABA_A$-receptors containing α1 subunits in the VP are thought to play an important role in regulating alcohol seeking behaviors. Without wishing to be bound by theory, it is thought that "competitive" benzodiazepine antagonists that exhibit binding selectivity at the α1 subtype, while concurrently displaying a partial agonist efficacy at non-α1 containing subtypes, may have important treatment implications in the design and development of novel pharmacotherapies for alcohol-dependent subjects. Thus, from a clinical perspective, α1 subtype antagonists capable of reducing alcohol intake, and capable of concurrently eliminating or attenuating the anxiety associated with abstinence or detoxification, would be useful pharmacotherapeutic agents in treating alcohol dependent individuals.

Administration

The compounds of this invention can be administered in a therapeutically effective amount by any of the accepted modes of administration for agents that serve similar utilities, e.g., oral, nasal, rectal and parenteral. As used herein, "parenteral" includes, but is not limited to, subcutaneous, intradermal, intravenous, intramuscular, intraperitoneal and intrathecal administration, such as by injection or infusion. The compounds of the invention may be administered separately or combined with each other or other agents known to be effective for the treatment of alcoholism or anxiety or anhedonia (e.g., naltrexone). The effective dose of the compounds of this invention, i.e., the active ingredient, will depend upon numerous factors such as the severity of the disease to be treated, the age, body weight, sex, diet and relative health of the subject, the potency of the compound used, the route and form of administration, and other factors. For example, it is well within the level of ordinary skill in the art to start doses at lower than those required to achieve the desired effect and to gradually increase the dosage until the desired effect is achieved.

Therapeutically effective amounts of the compounds may range from approximately 0.1-50 mg per kilogram body weight of the recipient per day; alternatively about 0.5-20 mg/kg/day can be administered. Thus, for administration to a 70 kg person, the dosage range could be about 40 mg to 1.4 g per day. In some embodiments, the compounds are administered more than once per day (e.g. 2×, 3× or 4× per day). In other embodiments, the compounds are administered once a day. Administration may also be less frequent than once a day, e.g., weekly, bi-weekly, monthly, etc. If desired, the effective daily dose may be divided into multiple doses for the purposes of administration.

Compositions containing aza-β-carbolines can be formulated according to known methods for preparing pharmaceutically useful compositions. In general, the compositions will be formulated such that an effective amount of the aza-β-carboline is combined with a suitable carrier in order to facilitate effective administration of the composition. The compositions of the invention may be prepared in various forms for administration. These include, for example, solid, semi-solid, and liquid dosage forms, such as tablets, caplets, pills, powders, capsules, dragees, liquid solutions or suspension, suppositories, injectable and infusible solutions, and sprays. The form will depend on the intended mode of administration and therapeutic application. As used herein, "carrier" includes any and all solvents, excipients, diluents, other liquid vehicle, dispersion or suspension aids, surface active ingredients, preservatives, solid binders, lubricants, and the like, as suited to the particular dosage form desired. Remington's Pharmaceutical Sciences, Fifteenth Edition, E. W. Martin (Mack Publishing Co., Easton Pa. 1975) discloses various vehicles or carriers used in formulating pharmaceutical compositions and known techniques for the preparation thereof. Except insofar as any carrier is incompatible with the compounds of the invention, such as by producing any undesirable biological effect or otherwise interacting in a deleterious manner with any other component(s) of the pharmaceutical composition, its use is contemplated to be within the scope of the invention.

The pharmaceutical compositions may comprise between about 0.1% and 99%, and suitably between about 1 and 75% by weight of the total of one or more of the aza-β-carbolines of the present invention based on the weight of the total composition.

In some embodiments, the compositions described herein are formulated in dosage unit form for ease of administration and uniformity of dosage. A "dosage unit form" as used herein refers to a physically discrete unit of pharmaceutical composition for the patient to be treated. Each dosage should contain the quantity of active material calculated to produce the desired therapeutic effect either as such, or in association with the selected carrier.

The following examples are provided to facilitate the practice of the present invention. They are not intended to limit the invention in anyway.

EXAMPLES

Example 1

Synthesis of tert-Butyl pyridine[4',5'-4,5]pyrrolo[3,2-c]pyridine-8-carboxylate (1)

Tert-Butyl pyridine[4',5'-4,5]pyrrolo[3,2-c]pyridine-8-carboxylate (1) is synthesized from commercially available 4-bromopyridine-3-carbaxaldehyde (7) according to FIG. 7 ("bz" is benzene; "et" is ethyl). Commercially available reagents are used as received unless otherwise noted. Reactions requiring inert atmospheres are run under nitrogen unless otherwise noted.

Commercially available 4-bromopyridine-3-carbaxaldehyde (7) is subjected to a Horner-Wadsworth-Emmons reaction with methyl 2-(dimethoxycarbonyl)-2-[(phenylmethoxy) carbonylamino]acetate (8) in dichloromethane (DCM) with 1,8-diazabicyclo[5.4.0]undec-7-ene (DBU) to give methyl (2Z)-3-(4-bromo(3-pyridyl))-2-[(phenylmethoxy)carbonyl amino]prop-2-enoate (9). This compound is cyclized with CuI and L-Proline in 1,4-dioxane and potassium carbonate (base) to yield methylpyrrolo[4,5-c]pyridine 2-carboxylate (10). This compound is converted to the gramine derivative, methyl 3-[(dimethylamino)methyl]pyrrolo[4,5-c]pyridine-2-carboxylate (11) by refluxing with dimethyl amine hydrochloride and paraformaldehyde in methanol. Reaction of this gramine with ethyl nitro acetate (12) yields the nitro ester product, ethyl 3-[2-(methoxycarbonyl)pyrrolo[3,2-c]pyridine-3-yl]-2-nitropropanoate (13). This is reduced to its corresponding amine (14) with Raney Ni in ethanol and further cyclized to give ethyl 6-oxo-7,8,9-trihydropyridino[4',5'-4,5]pyrrolo[3,2-c]pyridine-8-carboxylate (15) by refluxing in xylene. The cyclic amide is aromatized with manganese dioxide in chloroform to give ethyl 6-hydroxypyridino[4',5'-4,5]pyrrolo[3,2-c]pyridine-8-carboxylate (16). Chlorination of this product with phosphorous oxychloride yields ethyl 6-chloropyridino[4',5'-4,5]pyrrol[3,2-c]pyridine-8-carboxylate (17) which upon reduction with Pd/C/$H_2$ in the presence of diisopropyl ethyl amine (as HCl scavenger) in ethanol gives ethyl pyridine[4',5'-4,5]pyrrolo[3,2-c]pyridine-8-carboxylate (18). The ethyl ester of this compound is hydrolyzed with 10% NaOH to give the corresponding acid product, pyridino[4',3'-4,5]pyrrolo[3,2-c]pyridine-8-carboxylic acid (19), which upon esterification with dimethylformamide di tert-butyl acetal in dimethylformamide (DMF) delivers the desired tert-Butyl pyridine[4',5'-4,5]pyrrolo[3,2-c]pyridine-8-carboxylate (1).

To isolate the product (tert-Butyl pyridine[4',5'-4,5]pyrrolo [3,2-c]pyridine-8-carboxylate, 1), the reaction mixture is cooled to ambient temperature and diluted with water (~30 mL). The reaction mixture is transferred to a separatory funnel and extracted with ethyl acetate (2×150 mL). The combined organic extracts are washed with water (30 mL) and saturated brine solution (60 mL), and then dried over magnesium sulfate. The mixture is filtered through a glass fiber filter, and the filtrate is concentrated under reduced pressure to complete dryness. The residue is triturated with methyl tert-butyl ether (MTBE) (6 mL) and filtered. The solid is dried under high vacuum overnight at room temperature.

Example 2

Synthesis of 8-Propoxypyridino[4,3'-5,4]pyrrolo[3,2-c]pyridine hydrochloride (2)

8-Propoxypyridino[4',3'-5,4]pyrrolo[3,2-c]pyridine hydrochloride (2) was synthesized from commercially available 4-aminopyridine (20) and 5-chloro-2-fluoropyridine (22) according to FIG. 8 ("Pr" is propyl). Commercially available reagents were used as received unless otherwise noted. Reactions requiring inert atmospheres were run under nitrogen unless otherwise noted.

Synthesis of 4-amino-3-iodopyridine (21, Step a)

A 2 L three-neck round-bottom flask was equipped with a mechanical stirrer, thermocouple, addition funnel, nitrogen inlet, and reflux condenser fitted with a drying tube and placed into a heating mantle. The flask was charged with glacial acetic acid (523 mL), and stirring was initiated. 4-aminopyridine (20, 95 g) was added to the reaction as a single portion, and the dissolution of the material was exothermic to ~30° C. Iodine monochloride (101 mL) was added slowly over a 2 hour period at a rate to keep the internal temperature below 45° C. At the end of the addition the temperature had reached ~42° C. After the complete addition of iodine monochloride, the exotherm was allowed to subside and then heating was applied to the reaction to maintain the temperature at 45-50° C. Stirring was continued at 45-50° C. overnight and continued for 10 days until the reaction was deemed to be complete, i.e., when no significant progress was being made towards product. The reaction was monitored by HPLC (MPP-LC1 (270)) by diluting an aliquot of the reaction mixture (~1 mL) at various time points with (1:1) acetonitrile/water (~2 mL) and submitting for analysis. The starting material eluted at 2.8 min, and the product eluted at 8.1 min. Materials used in the synthesis are detailed in Table 1.

TABLE 1

Materials used in synthesis of 4-amino-3-iodopyridine (21)

| Compound | MW (g/mol) | d (g/mL) | Equivalents | Amt/mol | Lot # |
|---|---|---|---|---|---|
| Reaction | | | | | |
| 4-Aminopyridine | 94.12 | — | 1.0 eq. | 95 g/101 mol | R11-2408-03 |
| Iodine monochloride (ICl) | 162.36 | 3.240 | 2.0 eq. | 101 ml/2.02 mol | R03-0508-01 |
| glacial Acetic acid | 60.05 | 1.049 | 5.5 vols. | 523 ml | |
| Isolation | | | | | |
| Water | 18.02 | 1.000 | 41 vols. | 3.9 L | RO water |
| 50% Sodium hydroxide solution | 40.00 | 1.515 | — | As required | 08-2208-01 |
| Ethyl acetate | 88.11 | 0.902 | 84 vols. | 8 L | R09-0508-02 |
| 15% Sodium thiosulfate | — | — | 42 vols. | 4 L | R07-1107-06 |
| Saturated brine solution | — | — | 21 vols. | 2 L | R08-1208-09 |

To isolate 4-amino-3-iodopyridine (21), the reaction mixture was cooled to ambient temperature and diluted with 1.9 L of water. The solution was cooled in an ice/water bath to 0-5° C. and adjusted to pH ~10 with 50% sodium hydroxide solution and strong stirring. The addition of NaOH was strongly exothermic, and ice was added if required. During the pH adjustment brown solids formed. Ethyl acetate (4 L) was added, the biphasic solution was agitated, and the layers were allowed to separate. The brown solids dissolved during the extraction, by maintaining agitation and adding more ethyl acetate if needed. The aqueous layer was extracted with fresh ethyl acetate (4 L), the biphasic solution was agitated, and the layers were allowed to separate. The combined ethyl acetate extracts were washed sequentially with 15% sodium thiosulfate solution (2×2 L), water (2 L), and saturated brine solution (2 L), and then dried over sodium sulfate. The mixture was filtered through a glass microfiber filter, and the filtrate was evaporated under reduced pressure to give a brown solid. The solids were dissolved in 5% methanol in 1 L dichloromethane (DCM) and filtered through a 2" silica plug, washing with an additional 2 L of eluent. The solution was evaporated under reduced pressure to give a brown waxy solid. The solids were dried under vacuum at ambient temperature for a minimum of 12 h.

Results are shown in Table 2. 4-Amino-3-iodopyridine (21) (lot #1357-69-1) was a brown, waxy solid, synthesized with a yield of 173 g/78%. 4-Amino-3-iodopyridine (21) was analyzed using HPLC, and according to results, it was 92.3% pure. Mass spectrometry and $^1$H-NMR (300 MHz, CDCl$_3$) were also used to analyze 4-amino-3-iodopyridine (21), confirming the identity of the compound.

TABLE 2

Lot summary for the preparation of 4-amino-3-iodopyridine (21)

| SM Lot # | SM Batch Size | Yield (g/%) | Analysis | Product Lot # | Comments |
|---|---|---|---|---|---|
| R11-2408-03 | 5 g | 8.6 g/74% | HPLC: 92.5% | 1357-64-1 | 9 days reaction time |
| R11-2408-03 | 95 g | 173 g/78% | HPLC: 92.3% | 1357-69-1 | 10 days reaction time |

Synthesis of 5-chloro-2-propoxypyridine (23, Step b)

A 12 L three-neck round-bottom flask with a mechanical stirrer, thermocouple, addition funnel, nitrogen inlet, and a drying tube were equipped and placed into a cooling bath. An oversized flask was used due to the large amount of foaming and effervescence during the additions. The flask was charged with tetrahydrofuran (THF, 1.8 L), and stirring was initiated. Sodium hydride was added in portions. A mild exotherm was observed initially due to residual moisture in the solvent. After this had subsided the bulk of the material was added. The reaction mixture was cooled to 0-5° C. using an ice/water bath, and a solution of propanol (103 mL) in THF (350 mL) was added slowly over a 1 hour period at a rate to keep the internal temperature below 5° C. The addition was strongly exothermic and accompanied by the evolution of hydrogen gas. There was a significant delay (~45 mins) to the hydrogen release, which was sudden and caused foaming. After the complete addition of propanol, the reaction was stirred for a further 1 h. A solution of 5-chloro-2-fluoropyridine (22, 86 g) in tetrahydrofuran (THF, 350 mL) was added slowly over a 1.5 hour period at a rate to keep the internal temperature below 5° C. The addition was strongly exothermic and accompanied by the evolution of hydrogen gas. There was a significant delay (~45 mins) to the hydrogen release, which was sudden and caused foaming. The cooling bath was allowed to expire naturally overnight. Stirring was continued at ambient temperature until the reaction was complete, i.e., typically after overnight stirring without the requirement for additional reagents and when no starting material was observed. If reaction was not complete, it was cooled back to 0-5° C. and treated with fresh sodium hydride (0.5 eq.), the reaction was stirred at ambient temperature overnight, resampled, and the reaction was continued until deemed to be complete. The reaction was monitored by TLC (SiO$_2$, 25% ethyl acetate in heptanes, UV) by diluting an aliquot of reaction mixture (~1 mL) with water (~2 mL), extracting with ethyl acetate, and spotting the organic layer. The starting material had retention factor (RF)=0.38; the product had RF=0.45. Materials used in the synthesis are detailed in Table 3.

TABLE 3

Materials used in the synthesis of 5-chloro-2-propoxypyridine (23)

| Compound | MW (g/mol) | d (g/mL) | Equivalents | Amt/mol | Lot # |
|---|---|---|---|---|---|
| Reaction | | | | | |
| 5-Chloro-2-fluoropyridine | 131.54 | 1.311 | 1.0 eq. | 86 g/0.65 mol | R11-2408-04 |
| Sodium hydride (60% suspension on mineral oil) | 24.0 | — | 2.0 eq. | 52.3 g/1.31 mol | R03-1907-19 |
| Propan-1-ol (anhydrous) | 60.1 | 0.804 | 2.1 eq. | 103 ml/1.37 mol | R10-0108-04 |
| THF (anhydrous) | 72.11 | 0.889 | 15 vols. | 2.5 L | R10-2808-02 |
| Isolation | | | | | |
| Ethyl acetate | 88.11 | 0.902 | 46.5 vols. | 4 L | R09-0508-02 |
| Saturated ammonium chloride solution | — | — | 11.6 vols. | 1 L | R06-0808-04 |
| Saturated brine solution | — | — | 11.6 vols. | 1 L | R08-1208-09 |

To isolate 5-chloro-2-propoxypyridine (23), the reaction mixture was cooled to 0-5° C. using an ice/water bath. The reaction was quenched by the addition of a slow stream of saturated aqueous ammonium chloride solution (1 L). The addition was exothermic and may be accompanied by hydrogen gas evolution. The mixture was extracted with ethyl acetate (2×2 mL). The combined organic extracts were washed with saturated brine solution (1 L), dried over magnesium sulfate and charcoal, and filtered through a glass fiber filter. The filtrate was concentrated under reduced pressure to give a pale yellow liquid.

The reaction was successfully carried out on multi-gram scale giving both excellent yield and purity, and the results are shown in Table 4. 5-Chloro-2-propoxypyridine (23) (lot

1357-96-1) was a pale yellow liquid, synthesized with a yield of 110 g/98%. 5-Chloro-2-propoxypyridine (23) was analyzed using HPLC, and according to results, it was 99.0% pure. $^1$H-NMR (300 MHz, CDCl$_3$) was also used to analyze 5-chloro-2-propoxypyridine (23), confirming the identity of the compound.

TABLE 4

Lot summary for the preparation of 5-chloro-2-propoxypyridine (23)

| SM Lot # | SM Batch Size | Yield (g/%) | Analysis | Product Lot # | Comments |
|---|---|---|---|---|---|
| R11-2408-04 | 5 g | 6.4 g/98% | HPLC: 98.2% | 1357-75-1 | None |
| R11-2408-04 | 25 g | 32 g/98% | HPLC: 99.0% | 1357-79-1 | None |
| R11-2408-04 | 86 g | 110 g/98% | NMR conforms | 1357-96-1 | None |

Synthesis of 5-Chloro-2-propoxy-4-pyridinylboronic acid (24, Step c)

A 2 L three-neck round-bottom flask was equipped with a mechanical stirrer, thermocouple, addition funnel, nitrogen inlet, and reflux condenser fitted with a drying tube and placed into a cooling bath. The flask was charged with a solution of 5-chloro-2-propoxypyridine (23, 32 g) in THF (600 mL), and stirring was initiated. The solution was cooled in a dry ice/ether/acetone bath to −78 to −82° C. It was important to maintain this temperature throughout the entire reaction. Lithium diisopropylamide (LDA, 112 mL) was added as a slow stream over about a 1 hour period at a rate to keep the internal temperature between −78 to −82° C. The addition was mildly exothermic, leading to a clear orange-brown solution. The reaction was stirred for a further 2 h. Triisopropylborate (TPB, 88 mL) was added as a steady stream over about a 30 minute period at a rate to keep the internal temperature between −78 to −82° C. The addition was mildly exothermic, leading to an orange solution. Some solids were present at this time. The reaction was stirred for a further 3 h. Water (500 mL) was added as a steady stream over about a 30 minute period at a rate to keep the internal temperature between −60 to −82° C. The addition was strongly exothermic. The reaction was allowed to reach ambient temperature, and it was stirred rapidly overnight. It was observed that this reaction was highly temperature sensitive; it was maintained below −78° C. throughout. It was also observed that an increase in temperature, particularly during anion formation, could result in lower yields and byproduct formation. The materials used to synthesize 5-chloro-2-propoxy-4-pyridinylboronic acid (24) are shown in Table 5.

TABLE 5

Materials used in the synthesis of 5-chloro-2-propoxy-4-pyridinylboronic acid (24)

| Compound | MW (g/mol) | d (g/mL) | Equivalents | Amt/mol | Lot # |
|---|---|---|---|---|---|
| Reaction | | | | | |
| 5-Chloro-2-propoxy pyridine | 171.63 | — | 1.0 eq. | 32 g/0.18 mol | 1357-79-1 |
| Lithium diisopropylamide (2.0 M solution in THF/heptanes/ethyl benzene) (LDA) | 107.12 | 0.812 | 1.2 eq. | 112 mL/0.22 mol | R11-2408-05 |
| Triisopropylborate (TPB) | 188.08 | 0.878 | 2.05 eq. | 88 mL/0.38 mol | R07-1007-03 |
| THF (anhydrous) | 72.11 | 0.889 | 20 vols. | 600 mL | R10-2808-02 |
| Isolation | | | | | |
| Water | 18.02 | 1.000 | 15.6 vols. | 500 mL | RO water |
| Diethyl ether | 74.12 | 0.706 | 28.1 vols. | 900 mL | NA |
| Ethyl acetate | 88.11 | 0.902 | 65.6 vols. | 2.1 L | R09-0508-02 |
| 50% Sodium hydroxide | 40.00 | 1.515 | | As required | 08-2208-01 |
| 48% Hydrobromic acid | 80.91 | 1.490 | | As required | NA |
| Saturated brine solution | — | — | 15.6 vols. | 500 mL | R08-1208-09 |

To isolate 5-chloro-2-propoxy-4-pyridinylboronic acid (24), the biphasic reaction mixture was transferred to a Buchi flask and concentrated under reduced pressure to remove the THF, leaving the aqueous residue. The pH of the aqueous layer was checked, and it was adjusted to pH ~10 with a small amount of 50% sodium hydroxide solution if needed. The aqueous mixture was extracted with diethyl ether (3×300 mL), and the organic extracts were discarded. The pH of the aqueous layer was adjusted to ~3-4 using 48% hydrobromic acid. The addition was exothermic, so ice cooling was used. The aqueous layer was extracted with ethyl acetate (3×700 mL), and the combined organic extracts were washed with saturated brine solution (500 mL) and dried over magnesium sulfate. The mixture was filtered through a glass microfiber filter, and the filtrate was evaporated under reduced pressure to give a sticky off-white solid. The solids were slurried in 15% (methyl tert-butyl ether, MTBE)/heptanes (300 mL) for a minimum of 30 min. The solids were filtered onto a polypropylene filter pad and washed with fresh heptanes (100 mL). The solids were dried under vacuum at ambient temperature for a minimum of 12 h.

Results are shown in Table 6. 5-Chloro-2-propoxy-4-pyridinylboronic acid (24) (lot #1357-82-1) was a white solid, synthesized with a yield of 29.9 g/74%. 5-Chloro-2-propoxy-4-pyridinylboronic acid (24) was analyzed using HPLC, and according to results, it was 94.4% pure. $^1$H-NMR (300 MHz, Acetone-$_{d6}$) was also used to analyze 5-chloro-2-propoxy-4-pyridinylboronic acid (24), confirming the identity of the compound.

TABLE 6

Lot summary for the preparation of 5-chloro-2-propoxy-4-pyridinylboronic acid (24)

| SM Lot # | SM Batch Size | Yield (g/%) | Analysis | Product Lot # | Comments |
|---|---|---|---|---|---|
| 1357-75-1 | 5 g | 2.36 g/38% | HPLC: 98.0% | 1357-76-1 | None |
| 1357-79-1 | 32 g | 29.9 g/74% | HPLC: 94.4% | 1357-82-1 | None |
| 1357-96-1 | 125 g | 82 g/52% | HPLC: 89.1% | 1357-100-1 | None |

Synthesis of 3-(5-chloro-2-propoxy-4-pyridyl)-4-pyridylamine (25, Step d)

A 1 L three-necked round-bottomed flask was equipped with a magnetic bead, thermocouple, nitrogen inlet immersion tube, and reflux condenser and placed into a heating mantle. The flask was charged with 4-amino-3-iodopyridine (21, 10 g) and 1,4-dioxane (408 mL), and stirring was initiated. The resulting solution was degassed with nitrogen for 10 minutes. 5-Chloro-2-propoxy-4-pyridinylboronic acid (24, 14.7 g) was added as a single portion, followed by a solution of K$_3$PO$_4$ (28.93 g) and water (136 mL). The addition of the base solution facilitated dissolution of the boronic acid which remained mostly in suspension until then. The solution was continued to be degassed for a minimum of 10 minutes. Dichlorobis(triphenyl phosphine)palladium (II) (3.19 g) was charged. The resulting orange color solution was heated to reflux (~89° C.) for a minimum of 20 hours. The reaction mixture continued to be stirred at reflux until the reaction was complete, i.e., when no significant progress was being made towards product. If the reaction was not complete, stirring was continued at 89° C. overnight, a sample was taken, and stirring was continued until the reaction was deemed to be complete with addition of more boronic acid as needed. The reaction was monitored by HPLC (MPP-LC1 (270)) by diluting an aliquot of reaction mixture (~1 mL) with (1:1) acetonitrile/water (~2 mL) and submitting for analysis. The starting material eluted at 13.6 min, and the product eluted at 16.3 min. Materials used to synthesize 3-(5-chloro-2-propoxy-4-pyridyl)-4-pyridylamine (25) are shown in Table 7.

TABLE 7

Materials used to synthesize 3-(5-chloro-2-propoxy-4-pyridyl)-4-pyridylamine (25)

| Compound | MW (g/mol) | d (g/mL) | Equivalents | Amt/mol | Lot # |
|---|---|---|---|---|---|
| Reaction | | | | | |
| 4-Amino-3-iodopyridine | 220.01 | — | 1.0 eq. | 10 g/45.4 mmol | 1357-69-1 |
| 5-Chloro-2-propoxy-4-pyridinylboronic acid | 215.45 | — | 1.5 eq. | 12471019.2514.7 g/68.2 mmol | 1357-100-1 |
| Potassium phosphate tribasic (K$_3$PO$_4$) | 212.12 | — | 3.0 eq. | 28.93 g/0.14 mol | R07-0808-03 |
| Dichlorobis(triphenyl phosphine)palladium (II) | 701.89 | — | 0.1 eq. | 3.19 g/4.5 mmol | R09-1108-01 |
| 1,4-Dioxane | 88.11 | 1.034 | 40.8 vols. | 408 mL | R03-3007-06 |
| Water | 18.02 | 1.000 | 13.6 vols. | 136 mL | RO water |
| Isolation | | | | | |
| Diethyl ether | 74.12 | 0.706 | 10 vols. | 100 mL | NA |
| 2N Hydrochloric acid (HCl) | — | — | — | 100 mL | NA |
| Potassium carbonate | 138.21 | — | — | As required | NA |
| Ethyl acetate | 88.11 | 0.902 | 60 vols. | 600 mL | R09-0508-02 |
| Water | 18.02 | 1.000 | 10 vols. | 100 mL | RO water |
| Saturated brine solution | — | — | 10 vols. | 100 mL | R08-1208-09 |

To isolate 3-(5-chloro-2-propoxy-4-pyridyl)-4-pyridylamine (25), the reaction mixture was cooled to ambient temperature and concentrated under reduced pressure at 40° C. The residue was partitioned between 2N hydrochloric acid (HCl) solution (100 mL) and ether (100 mL), and the mixture was stirred at ambient temperature for 20 minutes. The reaction mixture was transferred to a separatory funnel, and the layers were allowed to separate. The ether extract was discarded. The pH of the aqueous layer was adjusted to ~pH 10 using potassium carbonate, and extracted with ethyl acetate (2×300 mL). The combined organic extracts were washed with water (100 mL), saturated brine solution (100 mL), and dried over magnesium sulfate. The mixture was filtered through a glass fiber filter, and the filtrate was concentrated under reduced pressure. The crude semisolid was loaded on top of a silica column (400 g) packed with DCM, using further DCM for loading. The column was eluted under gravity sequentially with DCM (1 L), 0.5% MeOH in DCM (0.5 L), 1% MeOH in DCM (0.5 L), and 1.5% MeOH in DCM (3 L), collecting fractions of ~150 mL. Increasing the methanol percentage in small increments helped facilitate effective purification. The column was eluted under gravity with 2% MeOH in DCM until complete removal of the clean product was observed by TLC analysis. All fractions containing clean product were combined and concentrated under reduced pressure to give a yellow semi-solid. The impure fractions were kept aside for further purification if necessary.

Results are shown in Table 8. 3-(5-Chloro-2-propoxy-4-pyridyl)-4-pyridylamine (25) (lot #1457-16-1) was a yellow semi-solid, synthesized with a yield of 4.15 g/35%. 3-(5-Chloro-2-propoxy-4-pyridyl)-4-pyridylamine (25) was analyzed using HPLC, and according to results, it was 96.3% pure. Mass spectrometry and $^1$H-NMR (300 MHz, CDCl$_3$) were used to confirm the identity of 3-(5-chloro-2-propoxy-4-pyridyl)-4-pyridylamine (25).

4-pyridylamine (25, 2.8 g) in toluene (150 mL), and stirring was initiated. The reaction was carried out in a sealed tube, using a blast shield during the reaction. Sodium tert-butoxide (2.04 g) was added, and the resulting yellow slurry was degassed with nitrogen for 10 minutes. 2-Dicyclohexylphosphino-2'-(N,N-dimethylamino)biphenyl (DavePHOS, 1.09 g) was charged, and the solution was continued to be degassed for a minimum of 10 minutes. Tris(dibenzylidene acetone) palladium (0.97 g) was charged, and the tube was sealed. The resulting orange color solution was heated to ~95° C. in an oil bath for a minimum of 48 hours. Stirring was continued at ambient temperature until the reaction was complete, i.e., when <1% starting material remained, or no further progress towards product was being observed. If reaction was not complete, it was degassed with nitrogen, fresh ligand and catalyst were added, stirring was continued at 95° C. for a minimum of 48 h, another sample was taken, and the reaction was continued until deemed to be complete. The reaction was maintained at 95° C. for 6 days before isolation, and it required addition of fresh catalyst and ligand after 3 days. The reaction was monitored by HPLC (LIL-LC4e (220)), by cooling the sealed tube and opening it under a nitrogen stream,

TABLE 8

Lot summary for the preparation of 3-(5-chloro-2-propoxy-4-pyridyl)-4-pyridylamine (25)

| SM Lot # | SM Batch Size | Yield (g/%) | Analysis | Product Lot # | Comments |
|---|---|---|---|---|---|
| 1357-64-1 | 213 mg | 110 mg/43% | — | 1357-78-1 | None |
| 1357-64-1 | 1.36 g | N/A | — | 1357-80-1 | Combined for |
| 1357-69-1 | 5 g | 4.4 g/74% | HPLC: 89.6% | 1357-94-1 | column |
| 1357-69-1 | 9.5 g | 9.02 g | HPLC: 73% | 1457-9-1 | Re-column gave 3.6 g clean |
| 1357-69-1 | 10 g | 4.15 g/35% | HPLC: 96.3% | 1457-16-1 | None |
|  |  | 4.7 g | HPLC: 82.1% | 1457-16-2 | Impure materials kept aside |

Synthesis of 8-propoxypyridino[4',3'-5,4]pyrrolo[3,2-c]pyridine (26, Step e)

A 250 mL thick-walled screw-capped reaction tube was charged with a solution of 3-(5-chloro-2-propoxy-4-pyridyl)- diluting an aliquot of reaction mixture (~1 mL) with (1:1) 9. acetonitrile/water (~2 mL), and submitting for analysis. The starting material eluted at 9.2 min, and the product eluted at 8.2 min. Materials used for the synthesis of 8-propoxypyridino[4',3'-5,4]pyrrolo[3,2-c]pyridine (26) are shown in Table

TABLE 9

Materials used in the synthesis of 8-propoxypyridino[4',3'-5,4]pyrrolo[3,2-c]pyridine (26).

| Compound | MW (g/mol) | d (g/mL) | Equivalents | Amt/mol | Lot # |
|---|---|---|---|---|---|
| Reaction | | | | | |
| 3-(5-Chloro-2-propoxy-4-pyridyl)-4-pyridylamine | 263.5 | — | 1.0 eq. | 2.8 g/10.6 mmol | 1457-16-1 |
| Sodium tert-butoxide | 96.11 | — | 2.0 eq. | 2.04 g/21.3 mmol | R09-0808-01 |
| Tris(dibenzylidene acetone)palladium | 915.7 | — | 0.1 eq. | 0.97 g/1.1 mmol | R06-1808-01 |
| 2-Dicyclohexylphosphino-2'-(N,N-dimethylamino)biphenyl (DavePHOS) | 342.51 | — | 0.3 eq. | 1.09 g/3.3 mmol | R12-1907-57 |

TABLE 9-continued

Materials used in the synthesis of
8-propoxypyridino[4',3'-5,4]pyrrolo[3,2-c]pyridine (26).

| Compound | MW (g/mol) | d (g/mL) | Equivalents | Amt/mol | Lot # |
|---|---|---|---|---|---|
| Toluene | 92.14 | 0.865 | 54 vols. | 150 mL | R09-1508-17 |
| Isolation | | | | | |
| Ethyl acetate | 88.11 | 0.902 | | 350 mL | R09-0508-02 |
| 2N HCl solution | — | — | | 100 mL | NA |
| Potassium carbonate | 138.21 | — | — | As required | NA |
| Saturated brine solution | — | — | | 50 mL | R08-1208-09 |

To isolate 8-propoxypyridino[4',3'-5,4]pyrrolo[3,2-c]pyridine (26), the reaction tube was allowed to cool to ambient temperature. The reaction was concentrated under reduced pressure to give the crude material. Material was combined with previous lots for purification. The crude material was partitioned between ethyl acetate (50 mL) and 1N HCl solution (100 mL), agitated, and the layers were allowed to separate. The aqueous layer was washed with further ethyl acetate (2×50 mL), and all the organic extracts were discarded. The aqueous layer was basified to pH ~8 using solid potassium carbonate and then extracted with ethyl acetate (2×100 mL). At this point solids precipitated which were insoluble in either phase, these were removed by filtration through a glass fiber filter. These solids contained some product, however, it was not possible to isolate the material from the residual catalyst and ligand, and this material was discarded. The organic layer was washed with saturated brine solution (50 mL), dried over magnesium sulfate, and concentrated to dryness under reduced pressure. The material was purified by column chromatography on silica gel [~200 g] eluting with an increasing percentage of methanol in dichloromethane (DCM) from 0-5%.

Results are shown in Table 10. 8-Propoxypyridino[4',3'-5,4]pyrrolo[3,2-c]pyridine (26) (lot #1457-25-3) was a pale yellow solid, synthesized with a yield of 1.22 g/36%. 8-Propoxypyridino[4',3'-5,4]pyrrolo[3,2-c]pyridine (26) was analyzed using HPLC, and according to results, it was 95.8% pure. $^1$H-NMR (300 MHz, CDCl$_3$) was used to confirm the identity of 8-propoxypyridino[4',3'-5,4]pyrrolo[3,2-c]pyridine (26).

TABLE 10

Lot summary for the preparation of
8-propoxypyridino[4',3'-5,4]pyrrolo[3,2-c]pyridine (26)

| SM Lot # | SM Batch Size | Yield (g/%) | Analysis | Product Lot # | Comments |
|---|---|---|---|---|---|
| 1457-16-1 | 100 mg | 1.22 g/ 36% | N/A | 1457-18-1 | Materials combined for isolation as new Lot # 1451-25-3. |
| 1457-16-1 | 1 g | | N/A | 1457-22-1 | |
| 1457-16-1 | 2.8 g | | NMR conforms HPLC: 95.8% | 1457-24-1 | |

Synthesis of 8-propoxypyridino[4,3'-5,4]pyrrolo[3,2-c]pyridine hydrochloride (2, Step f)

A 100 mL three-necked round-bottomed flask was equipped with a magnetic bead, thermocouple, nitrogen inlet, and drying tube and placed into a cooling bath. The flask was charged with 8-propoxypyridino[4',3'-5,4]pyrrolo[3,2-c]pyridine (26, 1.2 g) and ether (50 mL), and stirring was initiated. Some solids were present at this time. The slurry was cooled to 0-5° C. using an ice/water bath, and HCl in ether (2 M solution, 7.93 mL) was added slowly over 5 minutes. A mild exotherm was observed, with yellow solids forming over time. The reaction was continued to be stirred at ambient temperature for 5 hours. Materials used to synthesize 8-propoxypyridino[4',3'-5,4]pyrrolo[3,2-c]pyridine hydrochloride (2) are shown in Table 11.

TABLE 11

Materials used to synthesize 8-propoxypyridino[4',3'-5,4]pyrrolo[3,2-c]pyridine hydrochloride (2)

| Compound | MW (g/mol) | d (g/mL) | Equivalents | Amt/mol | Lot # |
|---|---|---|---|---|---|
| Reaction | | | | | |
| 8-Propoxypyridino[4',3'-5,4]pyrrolo[3,2-c]pyridine | 227.27 | — | 1.0 eq. | 1.2 g/5.3 mmol | 1457-25-3 |
| 2N HCl solution in diethyl ether | 36.46 | 0.747 | 3.0 eq. | 7.9 mL/15.9 mmol | R01-2609-01 |
| Diethyl ether | 74.12 | 0.706 | 42 vols. | 50 mL | NA |
| Isolation | | | | | |
| Diethyl ether | 74.12 | 0.706 | 12.5 vols. | 15 mL | NA |

To isolate 8-propoxypyridino[4',3'-5,4]pyrrolo[3,2-c]pyridine hydrochloride (2), the reaction mixture was cooled to 0-5° C. using an ice/water bath and stirred for a further 1 h. The solids were filtered onto a polypropylene filter pad and washed with fresh ether (15 mL) under a nitrogen atmosphere. The solids were dried under vacuum at 30° C. for a minimum of 24 h.

Results are shown in Table 12. 8-Propoxypyridino[4',3'-5,4]pyrrolo[3,2-c]pyridine hydrochloride (2) (lot #1457-26-1) was a yellow solid, synthesized with a yield of 1.49 g. 8-Propoxypyridino[4',3'-5,4]pyrrolo[3,2-c]pyridine hydrochloride (2) was analyzed using HPLC, and according to results, it was 95.8% pure. Mass spectrometry and $^1$H-NMR (300 MHz, $CDCl_3$) were used to confirm the identity of 8-propoxypyridino[4',3'-5,4]pyrrolo[3,2-c]pyridine hydrochloride (2).

TABLE 12

Lot summary for the preparation of 8-propoxypyridino[4',3'-5,4]pyrrolo[3,2-c]pyridine hydrochloride (2)

| SM Lot # | SM Batch Size | Yield (g/%) | Analysis | Product Lot # | Comments |
|---|---|---|---|---|---|
| 1457-25-3 | 1.2 g | 1.49 g | NMR conforms HPLC: 95.8% | 1457-26-1 | None |

Example 3

Synthesis of Tert-Butyl pyridine[4',5'-5,4]pyrrolo[2,3-c]pyridine-3-carboxylate (3)

Tert-Butyl pyridine[4',5'-5,4]pyrrolo[2,3-c]pyridine-3-carboxylate (3) was synthesized from commercially available 3-bromopyridine-4-carbaldehyde (28) according to FIG. 9. Alternatively, 3-bromopyridine-4-carbaldehyde (28) may be prepared from 3-bromopyrimidine (27) as shown in FIG. 9. Commercially available reagents were used as received unless otherwise noted. Reactions requiring inert atmospheres were run under nitrogen unless otherwise noted.

Synthesis of methyl(2Z)-3-(3-bromo(4-pyridyl))-2-[(phenylmethoxy) carbonyl amino]prop-2-enoate (29, Step a)

The reaction was carried out according to a procedure previously published and as previously described (*Tetrahedron Lett.* 2005, 46, 8877). A 3 L three-neck round-bottom flask was equipped with a mechanical stirrer, thermocouple, addition funnel, nitrogen inlet, and a drying tube and placed into a cooling bath. The flask was charged with methyl 2-(dimethoxycarbonyl)-2-[(phenylmethoxy)carbonylamino]acetate (8, 93.5 g) and dichloromethane (1000 mL). Stirring was initiated. The contents were cooled to 0° C. 1,8-diazabicyclo[5.4.0]undec-7-ene (44.22 mL) dissolved in dichloromethane (250 mL) was added dropwise over a period of 15 minutes. The solution was stirred at 0-5° C. for 30 minutes. The addition of the material was mildly exothermic to 5° C. 3-bromopyridine-4-carbaldehyde (28, 50 g) dissolved in dichloromethane (500 mL) was added as a slow steady stream through the addition funnel over a period of 30 minutes. The addition of the material was exothermic to ~30° C. The reaction mixture was allowed to warm to room temperature and continued to stir for a minimum of 3 h. The reaction mixture was continued to be stirred at ambient temperature until the reaction was deemed complete, i.e., upon complete disappearance of 3-bromopyridine-4-carbaldehyde (28). If reaction was not complete, stirring was continued at room temperature for additional 3 h then monitored again. Typically, the reaction was complete within 3-4 h and formed a yellow clear solution. The reaction was monitored by TLC ($SiO_2$, [5:5] EtOAc:Hept, UV) by spotting the reaction mixture directly on a TLC plate. The reactant (3-bromopyridine-4-carbaldehyde, 28) had an RF of 0.15, and the product (methyl (2Z)-3-(3-bromo(4-pyridyl))-2-[(phenylmethoxy)carbonyl amino]prop-2-enoate, 29) had an RF of 0.35. Materials used to synthesize methyl (2Z)-3-(3-bromo(4-pyridyl))-2-[(phenylmethoxy) carbonyl amino]prop-2-enoate (29) are shown in Table 13.

TABLE 13

Materials used to synthesize methyl (2Z)-3-(3-bromo(4-pyridyl))-2-[(phenylmethoxy) carbonyl amino] prop-2-enoate (29)

| Compound | MW (g/mol) | d (g/mL) | Equivalents | Amt/mol | Lot # |
|---|---|---|---|---|---|
| Reaction | | | | | |
| 3-bromopyridine-4-carbaldehyde | 186 | — | 1.0 eq. | 50 g/0.269 mol | 1177-7-1 |
| Methyl 2-(dimethoxycarbonyl)-2-[(phenylmethoxy)carbonyl amino]acetate | 331.26 | — | 1.05 eq. | 93.50 g/0.282 mol | R03-0909-01 |
| 1,8-diazabicyclo[5.4.0]undec-7-ene | 152.24 | 1.018 | 1.1 vols. | 44.22 mL/0.296 mol | R03-0909-05 |
| dichloromethane | 84.93 | 1.325 | 35 mL/1 g | 1750 mL | CML bulk |
| Isolation | | | | | |
| dichloromethane | 84.93 | 1.325 | 10 mL/1 g | 500 mL | CML bulk |
| 1N HCl | 36.5 | — | 10 mL/1 g | 500 mL/1M solution | CML bulk |
| Water | 18.02 | 1.000 | 10 vols. | 500 mL | RO water |
| Saturated brine solution | — | — | 10 vols. | 500 mL | CML bulk |

To isolate the product (methyl (2Z)-3-(3-bromo(4-pyridyl))-2-[(phenylmethoxy) carbonyl amino]prop-2-enoate, 29), the reaction mixture was diluted with dichloromethane (500 mL) and transferred to a separatory funnel. The reaction mixture was washed with 1N HCl solution (2×250 mL) followed by washing with water (1×500 mL). The reaction mixture was washed with brine solution (1×500 mL). All the aqueous layers were discarded. The organic layer was dried over magnesium sulfate and charcoal, and then filtered. The filtrate was concentrated to 1/10th volume (~200 mL). Heptane (~400 mL) was added, the mixture was heated to 40-50° C. on a rotary evaporator for 10 minutes, and stirring was continued at room temperature overnight. The solids were filtered and dried overnight under high vacuum at room temperature for a minimum of 12 h.

Results are shown in Table 14. Methyl (2Z)-3-(3-bromo(4-pyridyl))-2-[(phenylmethoxy)carbonyl amino]prop-2-enoate (29, lot #1458-75-11) was a light yellow solid, synthesized with a yield of 140 g/67% (yield from two batches of 50 g each). Methyl (2Z)-3-(3-bromo(4-pyridyl))-2-[(phenylmethoxy) carbonyl amino]prop-2-enoate (29) was analyzed using HPLC, and according to results, it was 92.3% pure. $^1$H-NMR (300 MHz, CDCl$_3$) was used to confirm the identity of methyl (2Z)-3-(3-bromo(4-pyridyl))-2-[(phenylmethoxy) carbonyl amino]prop-2-enoate (29).

repeated at least three times to ensure that the flask was free from oxygen. The rubber septum was opened and the reaction was charged with L-proline (2.64 g). The sealing and purging steps were repeated again at least three additional times to ensure that the flask was free from oxygen. The rubber septum was opened and the reaction was charged with copper iodide (99.999% purity, 2.2 g). The flask was sealed again, and the sealing and purging steps were repeated again at least three additional times to ensure that the flask was free from oxygen. The resulting slurry was heated at 100° C. for 24 h. Stirring was continued at 100° C. until the reaction was deemed complete, i.e., upon disappearance of starting material (methyl (2Z)-3-(3-bromo(4-pyridyl))-2-[(phenylmethoxy) carbonyl amino]prop-2-enoate, 29). If the reaction was not complete, 0.1 equivalent of CuI and 0.2 equivalents of L-proline were added, the reaction was degassed, nitrogen was purged,

TABLE 14

Lot summary for the preparation of Methyl (2Z)-3-(3-bromo(4-pyridyl))-2-[(phenylmethoxy) carbonyl amino] prop-2-enoate (29)

| SM Lot # | SM Batch Size | Yield (g/%) | Analysis | Product Lot # | Comments |
|---|---|---|---|---|---|
| 1177-7-1 | 20 g | 25 g/60% | HPLC: 94.4% | 1358-92-1 | none |
| 1177-7-1 | 50 g | 72 g/68% | HPLC: 91.3% | 1458-15-1 | none |
| 1177-7-1 | 2 × 50 g | 140 g/67% | HPLC: 92.3% | 1458-75-11 | none |

Synthesis of methylpyrrolo[2,3-c]pyridine-2-carboxylate (30, Step b)

A 2 L single neck round bottom flask was equipped with a magnetic bar and a rubber septum. The flask was charged with anhydrous 1,4-dioxane (~675 mL). Methyl (2Z)-3-(3-bromo (4-pyridyl))-2-[(phenylmethoxy) carbonyl amino]prop-2-enoate (29, 45 g) was added, followed by addition of potassium carbonate (47.6 g) to the flask while stirring. The flask was sealed with rubber septum and degassed using an oil pump, and nitrogen was purged into the evacuated flask using needle/balloon technique. The sealing and purging steps were repeated the vessel was sealed, and stirring was continued at 100° C. for 12 h. Typically, the reaction was complete within 24 h and formed a yellow clear solution. The reaction was monitored by TLC (SiO$_2$, [5:95], MeOH:DCM:2-3 drops of aqueous NH$_3$, UV, two developments by diluting an aliquot (0.2 mL) with methanol (1 mL) and spotting the reaction mixture directly on a TLC plate. The starting material had an RF of 0.8, and the product had an RF of 0.35 (fluorescent spot). Materials used to synthesize methylpyrrolo[2,3-c]pyridine-2-carboxylate (30) are shown in Table 15.

TABLE 15

Materials used to synthesize methylpyrrolo[2,3-c]pyridine-2-carboxylate (30)

| Compound | MW (g/mol) | d (g/mL) | Equivalents | Amt/mol | Lot # |
|---|---|---|---|---|---|
| Reaction | | | | | |
| Methyl (2Z)-3-(3-bromo(4-pyridyl))-2-[(phenylmethoxy)carbonyl amino] prop-2-enoate | 391.22 | — | 1.0 eq. | 45 g/0.115 mol | 1458-75-11 |
| Potassium carbonate | 138.21 | — | 3.0 eq. | 47.6 g/0.345 mol | CML bulk |
| Copper iodide, 99.999% purity | 190.44 | — | 0.1 eq. | 2.2 g/0.0115 mol | R03-1009-01 |
| L-Proline | 115.13 | — | 0.2 eq. | 2.64 g/0.023 mol | R03-0909-02 |
| 1,4-dioxane | — | — | 15 mL/1 g | 675 mL | CML bulk |
| Isolation | | | | | |
| Tetrahydrofuran | — | — | 16 mL/1 g | 720 mL | CML bulk |

To isolate the product (methylpyrrolo[2,3-c]pyridine-2-carboxylate, 30), the reaction mixture was cooled to room temperature. The reaction was concentrated under vacuum on a rotary evaporator to complete dryness. THF (~650 mL) was added to the residue and heated to reflux. The slurry was maintained at reflux, while stirring, for 3-4 h. The insolubles were removed by hot filtration through a glass fiber filter. The filter cake was washed with hot THF (~50 mL). The filtrate was concentrated to ¹/₁₀th volume (~70 mL) and stirred overnight at room temperature. A light yellow solid precipitated. The yellow solid was filtered, washed with ice-cold THF (~25 mL), and dried under high vacuum overnight at room temperature.

Results are shown in Table 16. Methylpyrrolo[2,3-c]pyridine-2-carboxylate (30, lot #1458-83-1) was a pale yellow solid, synthesized with a yield of 10 g/49%. Methylpyrrolo[2,3-c]pyridine-2-carboxylate (30) was analyzed using HPLC, and according to results, it was 98.4% pure. $^1$H-NMR (300 MHz, CD$_3$OD) was used to confirm the identity of methylpyrrolo[2,3-c]pyridine-2-carboxylate (30).

charged with methylpyrrolo[2,3-c]pyridine-2-carboxylate (30, 10 g) in methanol (40 mL), and stirring was initiated. Dimethyl amine hydrochloride (8.3 g) was added followed by paraformaldehyde (3.05 g), and the tube was sealed. The sealed tube was heated, while stirring the slurry, to 72° C. for 24 h. Heating was stopped, and the reaction vessel was removed from the oil bath. The reaction was deemed complete upon disappearance of starting material (methylpyrrolo[2,3-c]pyridine-2-carboxylate (30). If reaction was not complete, 1 equivalent of both the reagents was added, the vessel was sealed, and stirring was continued overnight. Typically, reaction was complete within 24 h and formed a yellow clear solution. The reaction was monitored by TLC (SiO$_2$, [5:95], MeOH:DCM:2-3 drops of aqueous NH$_3$, UV, two developments) by diluting an aliquot (0.2 mL) with methanol (1 mL)

TABLE 16

Lot summary for the preparation of methylpyrrolo[2,3-c]pyridine-2-carboxylate (30)

| SM Lot # | SM Batch Size | Yield (g/%) | Analysis | Product Lot # | Comments |
|---|---|---|---|---|---|
| 1358-92-1 | 6 g | 50 mg/2% | NMR conforms | 1358-95-1 | None |
| 1358-99-1 | 18 g | 4.5 g/55% | HPLC: 99.9% | 1358-99-1 | None |
| 1458-15-1 | 72 g | 8 g/32% | NMR conforms | 1458-18-1 | Reaction done in a 3N RB flask with continuous N$_2$ flow |
| 1458-75-11 | 25 g | 1.6 g/10% | NMR conforms | 1458-76-1 | Reaction done with continuous N$_2$ bubbling into the reaction slurry. |
| 1458-75-11 | 10 g | 1 g/22% | NMR conforms | 1458-77-1 | Cesium carbonate was used as base instead of potassium carbonate |
| 1458-75-11 | 20 g | 3.1 g/34% | HPLC: 97.4% | 1458-78-1 | none |
| 1458-75-11 | 50 g | 9 g/40% | HPLC: 86.4% | 1458-79-1 | None |
| 1458-75-11 | 45 g | 10 g/49% | HPLC: 98.4% | 1458-83-1 | None |

Synthesis of Methyl 3-[(dimethylamino)methyl]pyrrolo[2,3-c]pyridine-2-carboxylate (31, Step c)

An appropriately sized sealed tube was equipped with a magnetic bar and placed into an oil bath. The tube was and spotting the reaction mixture directly on a TLC plate. The starting material had an RF of 0.35, and the product had an RF of 0.15. Materials used to synthesize methyl 3-[(dimethylamino)methyl]pyrrolo[2,3-c]pyridine-2-carboxylate (31) are shown in Table 17.

TABLE 17

Materials used to synthesize methyl 3-[(dimethylamino)methyl]pyrrolo[2,3-c]pyridine-2-carboxylate (31)

| Compound | MW (g/mol) | d (g/mL) | Equivalents | Amt/mol | Lot # |
|---|---|---|---|---|---|
| Reaction | | | | | |
| Methylpyrrolo[2,3-c]pyridine-2-carboxylate | 176.2 | — | 1.0 eq. | 10 g/0.0567 mol | 1458-83-1 |
| Dimethyl amine hydrochloride | 81.55 | — | 1.8 eq. | 8.3 g/0.1017 mol | R01-0308-05 |
| Paraformaldehyde | 30 | — | 1.8 eq. | 3.05 g/0.1017 mol | R01-0308-08 |
| Methanol | — | — | 4 vols. | 40 mL | CML bulk |

TABLE 17-continued

Materials used to synthesize methyl 3-[(dimethylamino)methyl]pyrrolo[2,3-c]pyridine-2-carboxylate (31)

| Compound | MW (g/mol) | d (g/mL) | Equivalents | Amt/mol | Lot # |
|---|---|---|---|---|---|
| Isolation | | | | | |
| Aq. Ammonia (15% in water) | 17 | — | 2 vol. | 20 mL | CML bulk |
| Ethyl acetate | 88.11 | 0.902 | 100 vols. | 1 L | CML bulk |
| Saturated brine solution | — | — | 10 vols. | 100 mL | CML bulk |

To isolate methyl 3-[(dimethylamino)methyl]pyrrolo[2,3-c]pyridine-2-carboxylate (31), the reaction mixture was transferred immediately to a Büchi flask, and it was concentrated under reduced pressure to remove methanol. The residue was cooled to room temperature, ice (~5 mL) was added, and the mixture was diluted with aqueous ammonia (~15 mL). The pH was checked after complete dissolution of all the residue. If it was not basic (pH 8-10), an appropriate amount of aqueous ammonia was added to get pH 8-10. The aqueous mixture was extracted with ethyl acetate (5×200 mL). All the extracts were combined, washed with brine solution (~100 mL), dried over magnesium sulfate, and filtered. The result was concentrated to complete dryness. The result was triturated with MTBE (~10 mL), filtered, and dried in a vacuum oven overnight at room temperature.

Results are shown in Table 18. Methyl 3-[(dimethylamino)methyl]pyrrolo[2,3-c]pyridine-2-carboxylate (31, lot #1458-85-1) was a white/light yellow solid, synthesized with a yield of 7 g/50%. Methyl 3-[(dimethylamino)methyl]pyrrolo[2,3-c]pyridine-2-carboxylate (31) was analyzed using HPLC, and according to results, it was 94.4% pure. $^1$H-NMR (300 MHz, CD$_3$OD) was used to confirm the identity of methyl 3-[(dimethylamino)methyl]pyrrolo[2,3-c]pyridine-2-carboxylate (31).

TABLE 18

Lot summary for the preparation of Methyl 3-[(dimethylamino)methyl]pyrrolo[2,3-c]pyridine-2-carboxylate (31)

| SM Lot # | SM Batch Size | Yield (g/%) | Analysis | Product Lot # | Comments |
|---|---|---|---|---|---|
| 1358-99-1 1458-18-1 | 4.5 g | 2.2 g/37% | HPLC: 98.4 g | | none |
| 1358-99-1 1458-18-1 | 5.6 g | 2.6 g/35% | HPLC: 97.3% | 1458-37-1 | none |
| 1458-76-1 1458-78-1 | 3 g | 1.1 g/32% | NMR conforms | 1458-82-1 | In an attempt to improve the yield this reaction was attempted in ethanol/IPA/tBuOH. |
| 1458-78-1 | 1 g | 0.65 g/48% | NMR conforms | 1458-82-1 | None |
| 1458-78-1 1458-79-1 | 5 g (two batches) | 7.6 g/58% | HPLC: 91.7% | 1458-84-1 | None |
| 1458-83-1 | 10 g | 7 g/50% | HPLC: 98.5% | 1458-85-1 | None |

Synthesis of Ethyl 3-[2-(methoxycarbonyl)pyrrolo[2,3-c]pyridine-3-yl]-2-nitropropanoate (32, Step d)

Ethyl 3-[2-(methoxycarbonyl)pyrrolo[2,3-c]pyridine-3-yl]-2-nitropropanoate (32) was synthesized according to a procedure previously published (*Synthetic Commun.* 1997, 27, 3201-3211). A 1 L single-necked round-bottomed flask was equipped with a magnetic bead and a reflux condenser and placed into an oil bath. The flask was charged with methyl 3-[(dimethylamino)methyl]pyrrolo[2,3-c]pyridine-2-carboxylate (31, 8 g) and xylene (200 mL), and stirring was initiated. The solid did not dissolve in xylene and remained as a slurry. The resulting solution was degassed with nitrogen for 10 minutes. Ethyl nitroacetate (12, ~11.4 mL) was added as a single portion to the slurry. The solution was continued to be degassed with nitrogen for a minimum of 1 h while stirring. At this stage a slight change in the nature of the slurry was observed, probably due to the formation of the gramine salt of ethyl nitroacetate. The reaction mixture was heated to reflux (~156° C.) for 4 h. During reflux, the solid went into solution and simultaneously a white/light yellowish solid precipitated. The reaction mixture was continued to be stirred at reflux until the reaction was deemed complete, i.e., when no starting material peaks were observed on NMR. Indeed, the NMR matched with the NMR of pure product. If reaction was not complete, stirring was continued at 156° C. for another 3 h until the reaction was deemed to be complete, with additional ethyl nitroacetate added as required. This reaction was typically complete in 3-4 h. The reaction was monitored by NMR by taking an aliquot of reaction mixture (~1 mL), cooling to room temperature, filtering through a polypad, washing with diethyl ether (~2 mL), and submitting the solid for NMR analysis. Materials used to synthesize ethyl 3-[2-(methoxycarbonyl)pyrrolo[2,3-c]pyridine-3-yl]-2-nitropropanoate (32) are shown in Table 19.

TABLE 19

Materials used to synthesize ethyl 3-[2-(methoxycarbonyl)pyrrolo[2,3-c]pyridine-3-yl]-2-nitropropanoate (32)

| Compound | MW (g/mol) | d (g/mL) | Equivalents | Amt/mol | Lot # |
|---|---|---|---|---|---|
| Reaction | | | | | |
| Methyl 3-[(dimethyl amino)methyl]pyrrolo [2,3-c]pyridine-2-carboxylate | 233.27 | — | 1.0 eq. | 8 g/0.034 mmol | 1458-84-1 1458-85-1 |
| Ethyl nitroacetate | 133.1 | 1.203 | 3.0 eq. | 11.4 mL/0.1026 mmol | R03-1609-01 |
| Xylene | — | — | 25 vol | 200 mL | |
| Isolation | | | | | |
| Diethyl ether | 74.12 | 0.706 | 10 vols. | 80 mL | CML bulk |

To isolate the product (ethyl 3-[2-(methoxycarbonyl)pyrrolo[2,3-c]pyridine-3-yl]-2-nitropropanoate, 32), the reaction mixture was cooled to 0° C. and stirred for at least 1 h (may be stirred overnight). The solid was filtered onto a polypad and washed with diethyl ether (~60 mL). Ether washings removed the color, and clean product was white/light yellow in color. The solid was dried under high vacuum for at least 24 h at room temperature.

Results are shown in Table 20. Ethyl 3-[2-(methoxycarbonyl)pyrrolo[2,3-c]pyridine-3-yl]-2-nitropropanoate (32, lot #1458-89-1) was an off-white solid, synthesized with a yield of 8 g/73%. Ethyl 3-[2-(methoxycarbonyl)pyrrolo[2,3-c]pyridine-3-yl]-2-nitropropanoate (32) was analyzed using HPLC, and according to results, it was 93.9% pure. $^1$H-NMR (300 MHz, $CD_3OD$) was used to confirm the identity of ethyl 3-[2-(methoxycarbonyl)pyrrolo[2,3-c]pyridine-3-yl]-2-nitropropanoate (32).

TABLE 20

Lot summary for the preparation of Ethyl 3-[2-(methoxycarbonyl)pyrrolo[2,3-c]pyridine-3-yl]-2-nitropropanoate (32)

| SM Lot # | SM Batch Size | Yield (g/%) | Analysis | Product Lot # | Comments |
|---|---|---|---|---|---|
| 1458-82-1 | 2.4 g | 2.1 g/72% | NMR conforms | 1458-86-1 | None |
| 1458-84-1 1458-85-1 | 4.2 g | 4 g/71% | HPLC: 92.9% | 1458-88-1 | None |
| 1458-84-1 1458-85-1 | 8 g | 8 g/73% | HPLC: 93.9% | 1458-89-1 | None |

Synthesis of Ethyl 1-oxo-2,3,4-trihydropyridino[4',5'-4,5]pyrrolo[2,3-c]pyridine-3-carboxylate (34, Steps e and f)

A small autoclave (~2 L capacity) was charged with ethyl 3-[2-(methoxy carbonyl)pyrrolo[2,3-c]pyridine-3-yl]-2-nitropropanoate (32) and ethanol (~1000 mL). The solid did not dissolve in ethanol. An approximate amount (~1 g) of Raney Ni was added to the solution, and the vessel was sealed. The autoclave was pressurized with nitrogen (30 to 40 psi), agitated briefly, and vented to hood. The nitrogen purge was repeated two additional times. The autoclave was pressurized with hydrogen (30 to 40 psi), agitated briefly, and vented to hood. The hydrogen purge was repeated two additional times. The autoclave was pressurized with hydrogen (60 psi), and stirring was initiated. The vessel was recharged as necessary to maintain a pressure of 60 psi. The vessel was heated to 42° C. The mixture was stirred for a minimum of 24 hours at 60 psi and 42° C. The reaction mixture was continued to be stirred at 42° C. until the reaction was deemed complete, i.e., when <2-3% starting material was observed by TLC. If the reaction was not complete, stirring was continued at 42° C. for an additional 6 h. Typically, the reaction was complete within 24 h. The reaction was monitored by TLC ($SiO_2$, [5:95], MeOH:DCM:2-3 drops of aqueous $NH_3$, UV, two developments) by directly spotting an aliquot of reaction mixture on a TLC plate. The starting material had an RF of 0.75, and the product had an RF of 0.3 (fluorescent spot). Materials used to synthesize ethyl 1-oxo-2,3,4-trihydropyridino[4',5'-4,5]pyrrolo[2,3-c]pyridine-3-carboxylate (34) are shown in Table 21.

TABLE 21

Materials used to synthesize ethyl 1-oxo-2,3,4-trihydropyridino[4',5'-4,5]pyrrolo[2,3-c]pyridine-3-carboxylate (34)

| Compound | MW (g/mol) | d (g/mL) | Equivalents | Amt/mol | Lot # |
|---|---|---|---|---|---|
| Reaction | | | | | |
| Ethyl 3-[2-(methoxy carbonyl)pyrrolo[2,3-c]pyridine-3-yl]-2-nitropropanoate | 322.30 | — | 1.0 eq. | 4 g/0.0124 mmol | 1458-89-1 |
| Raney Nickel | — | — | 25% by wt | 1 g | R02-0507-19 |
| Ethanol | — | — | 250 mL/1 g | 1000 mL | CML bulk |
| Xylene | | | 100 mL/1 g | 400 mL | R04-0709-08 |

TABLE 21-continued

Materials used to synthesize ethyl 1-oxo-2,3,4-trihydropyridino[4',5'-4,5]pyrrolo[2,3-c]pyridine-3-carboxylate (34)

| Compound | MW (g/mol) | d (g/mL) | Equivalents | Amt/mol | Lot # |
|---|---|---|---|---|---|
| Isolation | | | | | |
| Ethyl acetate | 88.11 | 0.902 | 60 vols. | 600 mL | CML bulk |

To isolate the product when the reaction was complete, the reaction mixture was cooled to room temperature and hydrogen was removed. The reaction was pressurized with nitrogen (30-40 psi) three times, and the reaction mixture was filtered through a glass-fiber filter pad. The filter cake was washed with hot absolute ethanol (1 L, ~70° C.). The filter cake was not allowed to dry. The filtrate was transferred to a single neck 2 L RB flask and concentrated to complete dryness on a rotary evaporator. Xylene (~400 mL) was added to the flask. The solid residue did not dissolve in xylene. The resulting solution was degassed with nitrogen for 20 minutes while stirring. The reaction mixture was heated to reflux (~156° C.) and stirred for 4 h. Stirring was continued at reflux until the reaction was deemed complete, i.e. when <2-3% starting material was observed by TLC. If the reaction was not complete, stirring was continued at reflux for an additional 3 h. Typically, the reaction was complete within 4 h. The reaction was monitored by TLC (SiO$_2$, [5:95], MeOH:DCM:2-3 drops of aqueous NH$_3$, UV, two developments) by directly spotting an aliquot of the reaction mixture on a TLC plate. The starting material had an RF of 0.3, and the product had an RF of 0.35 (fluorescent spot). The reaction mixture was then cooled to room temperature and concentrated on a rotary evaporator under vacuum to complete dryness. The yellow solid was triturated with ethyl acetate (20 mL) and filtered. The solid was washed with ethyl acetate (~10 mL). The solids were dried under high vacuum overnight at room temperature. The impure material (filtrate) was kept aside for further purification if necessary.

Results are shown in Table 22. Ethyl 1-oxo-2,3,4-trihydropyridino[4',5'-4,5]pyrrolo[2,3-c]pyridine-3-carboxylate (34, lot #1458-91-1, a total of 13 g was hydrogenated and combined before the xylene reflux) was a yellow solid, synthesized with a yield of 4.6 g/44% (yield from 13 g of nitro ester). Ethyl 1-oxo-2,3,4-trihydropyridino[4',5'-4,5]pyrrolo[2,3-c]pyridine-3-carboxylate (34) was analyzed using HPLC, and according to results, it was 87.4% pure. $^1$H-NMR (300 MHz, CD$_3$OD) was used to confirm the identity of Ethyl 1-oxo-2,3,4-trihydropyridino[4',5'-4,5]pyrrolo[2,3-c]pyridine-3-carboxylate (34).

TABLE 22

Lot summary for the preparation of ethyl 1-oxo-2,3,4-trihydropyridino[4',5'-4,5]pyrrolo[2,3-c]pyridine-3-carboxylate (34)

| SM Lot # | SM Batch Size | Yield (g/%) | Analysis | Product Lot # | Comments |
|---|---|---|---|---|---|
| 1458-89-1<br>1458-88-1<br>1458-86-1 | 13 g | 4.6 g/44% | HPLC: 87.4% | 1458-91-1 | None |

Synthesis of Ethyl 1-hydroxypyridino[4',5'-4,5]pyrrolo[2,3-c]pyridine-3-carboxylate (35, Step g)

A 1 L three-necked round-bottomed flask was equipped with a magnetic bead, thermocouple, nitrogen inlet, and reflux condenser and placed into a heating mantle. The flask was charged with ethyl 1-oxo-2,3,4-trihydropyridino[4',5'-4,5]pyrrolo[2,3-c]pyridine-3-carboxylate (34, 4.5 g) and chloroform (300 mL), and stirring was initiated. The resulting solution was degassed with nitrogen for 10 minutes. Manganese dioxide (45 g) was added as a single portion, and the reaction mixture was heated to reflux for a minimum of 12 h. The solid did not dissolve in chloroform. The reaction mixture was continued to be stirred at reflux until the reaction was deemed complete, i.e., when <2-3% starting material was observed by TLC. If the reaction was not complete, stirring was continued at reflux for an additional 6 h. Typically, the reaction was complete within 12 h. The reaction was monitored by TLC (SiO$_2$, [5:95], MeOH:DCM:2-3 drops of aqueous NH$_3$, UV, two developments) by directly spotting an aliquot of the reaction mixture on a TLC plate. The starting material had an RF of 0.35 (fluorescent spot), and the product had an RF of 0.4 (fluorescent spot). Materials used to synthesize ethyl 1-hydroxypyridino[4',5'-4,5]pyrrolo[2,3-c]pyridine-3-carboxylate (35) are shown in Table 23.

TABLE 23

Materials used to synthesize ethyl 1-hydroxypyridino [4',5'-4,5]pyrrolo[2,3-c]pyridine-3-carboxylate (35)

| Compound | MW (g/mol) | d (g/mL) | Equivalents | Amt/mol | Lot # |
|---|---|---|---|---|---|
| Reaction | | | | | |
| Ethyl 1-oxo-2,3,4-trihydropyridino[4',5'-4,5]pyrrolo[2,3-c]pyridine-3-carboxylate | 259.26 | — | 1.0 eq. | 4.5 g/0.0174 mmol | 1458-91-1 |
| Manganese dioxide | 86.94 | — | 10 times by Wt. | 45 g | R10-1607-12 |
| Chloroform | — | — | 66 mL/1 g | 300 mL | CML bulk |

TABLE 23-continued

Materials used to synthesize ethyl 1-hydroxypyridino [4',5'-4,5]pyrrolo[2,3-c]pyridine-3-carboxylate (35)

| Compound | MW (g/mol) | d (g/mL) | Equivalents | Amt/mol | Lot # |
|---|---|---|---|---|---|
| Isolation | | | | | |
| Ethyl acetate | 88.11 | 0.902 | 100 vols. | 4500 mL | CML bulk |

To isolate the product, (ethyl 1-hydroxypyridino[4',5'-4,5]pyrrolo[2,3-c]pyridine-3-carboxylate, 35), the reaction mixture was filtered, while hot, through a bed of celite (~3 g). The celite was washed with hot ethyl acetate (1 L, ~70° C.). The filtrate was kept aside. A 3 L three-necked round-bottomed flask was equipped with a magnetic bead, thermocouple, nitrogen inlet, and reflux condenser and placed into a heating mantle. The filter cake (MnO$_2$+Celite) was transferred to the flask along with ethyl acetate/MeOH mixture (9:1) (~2 L). The solution was heated to reflux for 4-5 h. The solution was filtered, while hot, through a glass fiber filter. Both the filtrates were combined and concentrated to complete dryness. The resulting solid was triturated with ethyl acetate (~20 mL) and filtered. The solid was dried under high vacuum for 24 h overnight.

Results are shown in Table 24. Ethyl 1-hydroxypyridino [4',5'-4,5]pyrrolo[2,3-c]pyridine-3-carboxylate (35, lot #1458-94-1) was a yellow/semi-white solid, synthesized with a yield of 3.6 g/80%. Ethyl 1-hydroxypyridino[4',5'-4,5]pyrrolo[2,3-c]pyridine-3-carboxylate (35) was analyzed using HPLC, and according to results, it was 92% pure. Mass Spectrometry and $^1$H-NMR (300 MHz, CD$_3$OD) were used to confirm the identity of ethyl 1-hydroxypyridino[4',5'-4,5]pyrrolo[2,3-c]pyridine-3-carboxylate (35).

TABLE 24

Lot summary for the preparation of Ethyl 1-hydroxypyridino [4',5'-4,5]pyrrolo[2,3-c]pyridine-3-carboxylate (35)

| SM Lot # | SM Batch Size | Yield (g/%) | Analysis | Product Lot # | Comments |
|---|---|---|---|---|---|
| 1458-91-1 | 4.5 g | 3.6 g/80% | HPLC: 92% | 1458-94-1 | None |

Synthesis of ethyl 1-chloropyridino[4',5'-4,5]pyrrol[2,3-c]pyridine-3-carboxyalte (36, Step h)

A 1 L three-necked round-bottomed flask was equipped with a magnetic bead, thermocouple, nitrogen inlet, and reflux condenser and placed into a heating mantle. The flask was charged with ethyl 1-hydroxypyridino[4',5'-4,5]pyrrolo[2,3-c]pyridine-3-carboxylate (35, 3.6 g) and phosphorous oxychloride (30 mL), and stirring was initiated. The solution was heated to 100° C. for 4 h. The reaction mixture was continued to be stirred at reflux until the reaction was deemed to be complete, i.e. when <2-3% starting material was observed by TLC. If reaction was not complete, stirring was continued at reflux for an additional 3 h. Typically, the reaction was complete within 4 h. The reaction was monitored by TLC (SiO$_2$, [5:95], MeOH:DCM:2-3 drops of aqueous NH$_3$, UV, two developments) by quenching an aliquot of reaction mixture (~1 mL) with saturated NaHCO$_3$ (pH after quenching was 8), diluting with ethyl acetate (~2 mL), and spotting the organic layer directly on TLC plate. The starting material had an RF of 0.4 (fluorescent spot), and the product had an RF of 0.6 (fluorescent spot). Materials used to synthesize ethyl 1-chloropyridino[4',5'-4,5]pyrrol[2,3-c]pyridine-3-carboxyalte (36) are shown in Table 25.

TABLE 25

Materials used to synthesize ethyl 1-chloropyridino[4',5'-4,5]pyrrol[2,3-c]pyridine-3-carboxyalte (36)

| Compound | MW (g/mol) | d (g/mL) | Equivalents | Amt/mol | Lot # |
|---|---|---|---|---|---|
| Reaction | | | | | |
| Ethyl 1-hydroxypyridino [4',5'-4,5]pyrrolo[2,3-c]pyridine-3-carboxylate | 257.26 | — | 1.0 eq. | 3.6 g/0.0139 mmol | 1458-94-1 |
| Phosphorous oxychloride | 153.33 | 1.675 | 24 eq. | 30 mL/0.3358 mmol | R10-2507-01 |
| Isolation | | | | | |
| Sat. sodium bicarbonate | — | — | — | As required | NA |
| Ethyl acetate | 88.11 | 0.902 | 100 vols. | 360 mL | CML bulk |

TABLE 25-continued

Materials used to synthesize ethyl 1-chloropyridino[4',5'-4,5]pyrrol[2,3-c]pyridine-3-carboxyalte (36)

| Compound | MW (g/mol) | d (g/mL) | Equivalents | Amt/mol | Lot # |
|---|---|---|---|---|---|
| Water | 18.02 | 1.000 | 100 vols. | 360 mL | RO water |
| Saturated brine solution | — | — | 20 vols. | 72 mL | CML bulk |

To isolate the product (ethyl 1-chloropyridino[4',5'-4,5]pyrrol[2,3-c]pyridine-3-carboxyalte, 36), the reaction mixture was cooled to ambient temperature and concentrated under reduced pressure at 40° C. The residue was diluted with ice (~10 mL) and saturated NaHCO$_3$ (~20 mL, pH of the solution was basic). The aqueous layer was extracted with ethyl acetate (3×300 mL). The combined organic extracts were washed with water (100 mL), saturated brine solution (100 mL), and dried over magnesium sulfate. The mixture was filtered through a glass fiber filter, and the filtrate was concentrated under reduced pressure. The solid residue was triturated with ethyl acetate (~5 mL) and filtered. The solid was dried under high vacuum overnight at room temperature.

Results are shown in Table 26. Ethyl 1-chloropyridino[4',5'-4,5]pyrrol[2,3-c]pyridine-3-carboxyalte (36, lot #1458-97-1) was a yellow/semi-solid, synthesized with a yield of 3 g/79%. Ethyl 1-chloropyridino[4',5'-4,5]pyrrol[2,3-c]pyridine-3-carboxyalte (36) was analyzed using HPLC, and according to results, it was 94.2% pure. Mass Spectrometry and $^1$H-NMR (300 MHz, CD$_3$OD) were used to confirm the identity of ethyl 1-chloropyridino[4',5'-4,5]pyrrol[2,3-c]pyridine-3-carboxyalte (36).

TABLE 26

Lot summary for the preparation of ethyl 1-chloropyridino[4',5'-4,5]pyrrol[2,3-c]pyridine-3-carboxyalte (36)

| SM Lot # | SM Batch Size | Yield (g/%) | Analysis | Product Lot # | Comments |
|---|---|---|---|---|---|
| 1458-94-1 | 3.6 g | 3 g | HPLC: 94.2% | 1458-97-1 | none |

Synthesis of Ethyl pyridine[4',5'-4,5]pyrrolo[2,3-c]pyridine-3-carboxylate (37, Step i)

The synthesis was carried out according a procedure modified from a protocol previously published (*Tetrahedron Lett.* 2006, 62, 7926). To ethyl 1-chloropyridino[4',5'-4,5]pyrrol[2,3-c]pyridine-3-carboxyalte (36, 3 g) in EtOH (750 mL), diisopropyl ethylamine (~9.4 mL) is added in a small autoclave. The starting material did not always dissolve completely. Pd/C (10 wt %), ~50% wet (0.3 g, 0.1 g/g SM) was charged to the reaction mixture. The autoclave was purged with nitrogen (3×30 psi). At least 1 minute of stirring was allowed for each purge prior to venting. The autoclave was purged with hydrogen (1×30 psi). At least 1 minute of stirring was allowed for purge prior to venting. The autoclave was pressurized with hydrogen (30 psi), and it was hydrogenated at room temperature for 2436 hrs. The reaction mixture was continued to be stirred in the autoclave under 30 psi until it was determined that the reaction was complete, i.e. when <2-3% starting material was observed by TLC. If reaction was not complete, stirring at reflux was continued for an additional 6 h and the reaction was monitored again. This process was continued until the reaction was complete. Typically, reaction was complete within 24 h. The reaction was monitored by TLC (SiO$_2$, [5:95], MeOH:DCM:2-3 drops of aqueous NH$_3$, UV, two developments) by directly spotting an aliquot of the reaction mixture on the TLC plate. The starting material had an RF of 0.4 (fluorescent spot), and the product had an RF of 0.2 (fluorescent spot). Materials used to synthesize ethyl pyridine[4',5'-4,5]pyrrolo[2,3-c]pyridine-3-carboxylate (37) are shown in Table 27.

TABLE 27

Materials used to synthesize ethyl pyridine[4',5'-4,5]pyrrolo[2,3-c]pyridine-3-carboxylate (37)

| Compound | MW (g/mol) | d (g/mL) | Equivalents | Amt/mol | Lot # |
|---|---|---|---|---|---|
| Reaction | | | | | |
| Ethyl 1-chloropyridino[4',5'-4,5]pyrrol[2,3-c]pyridine-3-carboxyalte | 275.7 | — | 1.0 eq. | 3 g/0.011 mol | 1458-97-1 |
| 10 wt. % Pd on carbon, ~50% wet | N/A | N/A | 0.1 g/g SM | 0.3 g | 06-1807-2 |
| Diisopropyl ethylamine | 129.25 | 0.747 | 5.0 eq. | 9.4 mL/0.0544 mol | R08-0707-12 |
| Ethanol | — | — | 250 mL/1 g | 750 mL | CML bulk |
| Isolation | | | | | |
| Ethyl acetate | 88.11 | 0.902 | 100 vols. | 300 mL | CML bulk |
| Dichloromethane | 84.93 | 1.325 | 10 mL/1 g | 30 mL | CML bulk |

To isolate the product (ethyl pyridine[4',5'-4,5]pyrrolo[2,3-c]pyridine-3-carboxylate, 37), the autoclave was purged with nitrogen (3×30 psi). At least 1 minute of stirring was allowed for each purge prior to venting. The catalyst was filtered off from the reaction mixture using a double glass fiber. The filter cake was rinsed with ethyl acetate (300 mL). The filtrate was concentrated under reduced pressure at 35/40° C. to dryness. The residue was triturated with dichloromethane (15 mL) and filtered. The solid was dried under high vacuum overnight at room temperature.

Results are shown in Table 28. Ethyl pyridine[4',5'-4,5]pyrrolo[2,3-c]pyridine-3-carboxylate (37, lot #1458-98-1) was an off-white solid, synthesized with a yield of 1.9 g/72%. Ethyl pyridine[4',5'-4,5]pyrrolo[2,3-c]pyridine-3-carboxylate (37) was analyzed using HPLC, and according to results, it was 97.2% pure. $^1$H-NMR (300 MHz, CDCl$_3$) was used to confirm the identity of ethyl pyridine[4',5'-4,5]pyrrolo[2,3-c]pyridine-3-carboxylate (37).

TABLE 28

Lot summary for the preparation of ethyl pyridine[4',5'-4,5]pyrrolo[2,3-c]pyridine-3-carboxylate (37)

| SM Lot # | SM Batch Size | Yield (g/%) | Analysis | Product Lot # | Comments |
|---|---|---|---|---|---|
| 1458-97-1 | 3 g | 1.9 g | HPLC: 97.2% | 1458-98-1 | none |

Synthesis of Pyridino[4',3'-4,5]pyrrolo[2,3-c]pyridine-3-carboxylic acid (38, Step j)

A 100 mL three-necked round-bottomed flask was equipped with a magnetic bead, thermocouple, and a nitrogen inlet and placed into a cooling bath. The flask was charged with ethyl pyridino[4',5'-4,5]pyrrolo[2,3-c]pyridine-3-carboxylate (37, 1.7 g) and 10% sodium hydroxide (17 mL), and stirring was initiated. The solid did not dissolve initially, but over a period of time (~1 h) it went into solution. Simultaneously, a solid started to precipitate. The solution was stirred for a minimum of 3 h at room temperature. The reaction mixture was continued to be stirred until the reaction was deemed to be complete, i.e., when no starting material was observed by TLC. If the reaction was not complete, stirring was continued at room temperature for an additional 3 h and monitored again. This process was continued until the reaction was complete. Typically, the reaction was complete within 3 h. The reaction was monitored by TLC (SiO$_2$, [5:95], MeOH:DCM:2-3 drops of aqueous NH$_3$, UV, two developments) by directly spotting on a TLC plate an aliquot of a reaction mixture. The starting material had an RF of 0.2 (fluorescent spot), and the product had an RF of 0.0 (fluorescent spot). Materials used to synthesize pyridino[4',3'-4,5]pyrrolo[2,3-c]pyridine-3-carboxylic acid (38) are shown in Table 29.

TABLE 29

Materials used to synthesize pyridino[4',3'-4,5]pyrrolo[2,3-c]pyridine-3-carboxylic acid (38)

| Compound | MW (g/mol) | d (g/mL) | Equivalents | Amt/mol | Lot # |
|---|---|---|---|---|---|
| Reaction | | | | | |
| Ethyl pyridine[4',5'-4,5]pyrrolo[2,3-c]pyridine-3-carboxylate | 241.25 | — | 1.0 eq. | 1.7 g/0.007 mmol | 1458-98-1 |
| 10% Sodium hydroxide solution | 40.00 | 1.515 | 1 mL/0.1 g | 17 mL | CML bulk |
| Isolation | | | | | |
| Conc. Hydrochloric acid | — | — | — | As required | CML bulk |
| Water | 18.02 | 1.000 | 3 vols. | 5 mL | RO water |

To isolate the product (pyridino[4',3'-4,5]pyrrolo[2,3-c]pyridine-3-carboxylic acid, 38), the reaction mixture was cooled to 0° C. Concentrated HCl was added to the reaction mixture and the pH was monitored. HCl was continued to be added dropwise until the pH was 2-3. After reaching the pH, stirring was continued for 1 h and the pH was monitored. If the pH of the solution was acidic (2-3), the solid was filtered through a poly pad. If not, concentrated HCl was added until the mixture was pH 2-3. The solids were washed with water (~5 mL). The solids were dried under high vacuum at 40° C. for a minimum of 48 h.

The results are shown in Table 30. Pyridino[4',3'-4,5]pyrrolo[2,3-c]pyridine-3-carboxylic acid (38, lot #1458-101-1) was a light yellow solid, synthesized with a yield of 1.5 g/35%. $^1$H-NMR (300 MHz, DMSO-$d_6$) was used to confirm the identity of pyridino[4',3'-4,5]pyrrolo[2,3-c]pyridine-3-carboxylic acid (38).

TABLE 30

Lot summary for the preparation of pyridino[4',3'-4,5]pyrrolo[2,3-c]pyridine-3-carboxylic acid (38)

| SM Lot # | SM Batch Size | Yield (g/%) | Analysis | Product Lot # | Comments |
|---|---|---|---|---|---|
| 1357-64-1 | 213 mg | 110 mg/43% | — | 1357-78-1 | None |
| 1357-64-1 | 1.36 g | N/A | — | 1357-80-1 | Combined |
| 1357-69-1 | 5 g | 4.4 g/74% | HPLC: 89.6% | 1357-94-1 | for column |
| 1357-69-1 | 9.5 g | 9.02 g | HPLC: 73% | 1457-9-1 | Re-column gave 3.6 g clean |
| 1357-69-1 | 10 g | 4.15 g/35% | HPLC: 96.3% | 1457-16-1 | None |
| | | 4.7 g | HPLC: 82.1% | 1457-16-2 | Impure materials kept aside |

Synthesis of tert-Butyl pyridine[4',5'-5,4]pyrrolo[2,3-c]pyridine-3-carboxylate (3, Step k)

A 250 mL three-necked round-bottomed flask was equipped with a magnetic bead, thermocouple, nitrogen inlet immersion tube, and reflux condenser and placed into a heating mantle. The flask was charged with pyridino[4',3'-4,5]pyrrolo[2,3-c]pyridine-3-carboxylic acid (38, 1.5 g) and N,N-dimethylformamide (22.5 mL), and stirring was initiated. The resulting solution was degassed with nitrogen for 10 minutes. Dimethylformamide ditert-butyl acetal (17 mL) was added as a single portion, and the reaction was heated to 90° C. The reaction mixture was stirred at 90° C. for 2-3 h. The reaction was continued to be stirred until the reaction was deemed to be complete, i.e., when no starting material was observed by TLC. If the reaction was not complete, stirring was continued at 90° C. for an additional 2 h and the reaction was monitored again. This process was continued until the reaction was complete. Typically, the reaction was complete within 3 h. The reaction was monitored by TLC (SiO$_2$, [5:95], MeOH:DCM:2-3 drops of aqueous NH$_3$, UV, two developments) by diluting an aliquot of reaction mixture (~0.5 mL) with water (~1 mL), extracting with ethyl acetate (~2 mL), and spotting the organic layer directly on TLC plate. The starting material had an RF of 0.0 (fluorescent spot), and the product had an RF of 0.4 (fluorescent spot). Materials used to synthesize tert-butyl pyridine[4',5'-5,4]pyrrolo[2,3-c]pyridine-3-carboxylate (3) are shown in Table 31.

TABLE 31

Materials used to synthesize tert-butyl pyridine[4',5'-5,4]pyrrolo[2,3-c]pyridine-3-carboxylate (3)

| Compound | MW (g/mol) | d (g/mL) | Equivalents | Amt/mol | Lot # |
|---|---|---|---|---|---|
| Reaction | | | | | |
| Pyridino[4',3'-4,5]pyrrolo[2,3-c]pyridine-3-carboxylic acid | 213 | — | 1.0 eq. | 1.5 g/0.007 mmol | 1458-101-1 |
| Dimethylformamide ditert-butyl acetal | 203.33 | 0.848 | 10 eq. | 17 mL/0.0704 mmol | R04-2309-05 |
| Dimethylformamide | 73.09 | 0.944 | 15 mL/1 g Isolation | 22.5 mL | R04-2909-01 |
| Water | 18.02 | 1.000 | 40 vols. | 60 mL | RO water |
| Ethyl acetate | 88.11 | 0.902 | 200 vols. | 300 mL | R09-0508-02 |
| Saturated brine solution | — | — | 40 vols. | 60 mL | CML bulk |
| Methyl tert-butyl ether | — | — | 4 vols. | 6 mL | CML bulk |

To isolate the product (tert-butyl pyridine[4',5'-5,4]pyrrolo[2,3-c]pyridine-3-carboxylate, 3), the reaction mixture was cooled to ambient temperature and diluted with water (~30 mL). The reaction mixture was transferred to a separatory funnel and extracted with ethyl acetate (2×150 mL). The combined organic extracts were washed with water (30 mL) and saturated brine solution (60 mL), and then dried over magnesium sulfate. The mixture was filtered through a glass fiber filter, and the filtrate was concentrated under reduced pressure to complete dryness. The residue was triturated with MTBE (6 mL) and filtered. The solid was dried under high vacuum overnight at room temperature.

Results are shown in Table 32. Tert-butyl pyridine[4',5'-5,4]pyrrolo[2,3-c]pyridine-3-carboxylate (3, lot #1458-102-1) was a light yellow solid, synthesized with a yield of 0.85 g/45%. Tert-butyl pyridine[4',5'-5,4]pyrrolo[2,3-c]pyridine-3-carboxylate (3) was analyzed using HPLC, and according to results, it was 98.5% pure. Mass spectrometry and $^1$H-NMR (300 MHz, CDCl$_3$) were used to confirm the identity of tert-butyl pyridine[4',5'-5,4]pyrrolo[2,3-c]pyridine-3-carboxylate (3).

TABLE 32

Lot summary for the preparation of tert-butyl pyridine[4',5'-5,4]pyrrolo[2,3-c]pyridine-3-carboxylate (3)

| SM Lot # | SM Batch Size | Yield (g/%) | Analysis | Product Lot # | Comments |
|---|---|---|---|---|---|
| 1357-69-1 | 66 mg | 45 mg/54% | NMR conforms | 1457-100-1 | Scouting run |

TABLE 32-continued

Lot summary for the preparation of tert-butyl pyridine[4',5'-5,4]pyrrolo[2,3-c]pyridine-3-carboxylate (3)

| SM Lot # | SM Batch Size | Yield (g/%) | Analysis | Product Lot # | Comments |
|---|---|---|---|---|---|
| 1458-101-1 | 1.5 g | 0.85 g | HPLC: 98.5% | 1457-102-1 | The starting material was recovered and subjected to the reaction again with same amount of equivalents. Both the product lots were combined. |

Example 4

Synthesis of 3-Propoxy pyridino[4',3'-4,5]pyrrolo[2,3-c]pyridine hydrochloride (4)

3-Propoxy pyridino[4',3'-4,5]pyrrolo[2,3-c]pyridine hydrochloride (4) was synthesized from commercially available reagents including 3-amino pyridine (40) according to FIG. 10. Commercially available reagents were used as received unless otherwise noted. Reactions requiring inert atmospheres were run under nitrogen unless otherwise noted.

Synthesis of 2,2-dimethyl-N-(3-pyridyl)propanamide (42, Step a)

The reaction was performed according to a procedure available in the literature (*J. Org. Chem.* 1983, 48, 3401-3408). A 1 L three-neck round-bottom flask was equipped with a mechanical stirrer, thermocouple, nitrogen inlet, and drying tube and placed in a cooling bath. The flask was charged with 3-amino pyridine (40, 25 g) and DCM (225 mL), and stirring was initiated. The reaction mixture was cooled in an ice/water bath to 0-10° C. Triethyl amine (46.2 mL) was added over at least 5 minutes. Trimethyl acetyl chloride (41, 36 mL) in DCM (25 mL) was added over at least a 30 minute period, keeping the temperature below 10° C. The reaction mixture was stirred continually at ambient temperature until the reaction was deemed complete, i.e., upon disappearance of 3-amino pyridine (40). If the reaction was not complete, it was stirred at room temperature for additional 3 h then monitored. Typically, the reaction was complete within 6 h. The reaction was monitored by TLC (SiO$_2$, [9:1] EtOAc:Hept, UV) by spotting an aliquot of the reaction mixture directly on a TLC plate. The reaction mixture was stirred continually overnight at room temperature, and the reactant (3-amino pyridine, 40) had an RF of 0.15, while the product (2,2-dimethyl-N-(3-pyridyl)propanamide, 42) had an RF of 0.35. The reaction mixture formed a dark brown clear solution. Materials used to synthesize 2,2-dimethyl-N-(3-pyridyl)propanamide (42) are shown in Table 33.

TABLE 33

Materials used to synthesize 2,2-dimethyl-N-(3-pyridyl)propanamide (42)

| Compound | MW (g/mol) | d (g/mL) | Equivalents | Amt/mol | Lot # |
|---|---|---|---|---|---|
| Reaction | | | | | |
| 3-Amino pyridine | 94.12 | NA | 1.00 | 25 g/0.265 mol | R12-1208-1 |
| Trimethyl acetyl chloride | 120.58 | 0.98 | 1.03 | 36 mL/0.292 mol | R11-1607-1 |
| Triethyl amine (TEA) | 101.19 | 0.726 | 1.25 | 46.2 mL/0.331 mol | R01-3108-10 |
| Methylene chloride (DCM) | 84.93 | 1.325 | 10 vol | 250 mL | R05-2208-1 |
| Isolation | | | | | |
| Aq. NaHCO$_3$ solution | NA | NA | 20 vol | 500 mL | R10-2308-1 |
| Magnesium sulfate | NA | NA | 0.33 g/g SM | 8.2 g | R03-0408-4 |
| Charcoal | NA | NA | 0.05 g/g SM | 1.25 g | R03-1308-4 |
| Brine | NA | NA | 10 vol | 250 mL | R08-1208-9 |

To isolate 2,2-dimethyl-N-(3-pyridyl)propanamide (42), the reaction mixture was washed with aqueous NaHCO$_3$ solution (2×250 mL) and brine (250 mL). The organic layer was dried over MgSO$_4$ and charcoal, filtered through glass fiber filter paper, and concentrated to dryness. The solids were slurried with MTBE:heptane (1:1, 150 mL) and filtered. The product was air-dried for 2 h and then dried under high vacuum at 40° C. to constant weight.

2,2-Dimethyl-N-(3-pyridyl)propanamide (42, lot #1358-74-1) was an off-white solid, synthesized with a yield of 40 g (84.5%). 2,2-Dimethyl-N-(3-pyridyl)propanamide (42) was analyzed using HPLC (MPP-LC1, 245 nm), and according to results, it was 99.7% pure. $^1$H-NMR (300 MHz, CDCl$_3$) was used to confirm the identity of 2,2-Dimethyl-N-(3-pyridyl) propanamide (42).

Synthesis of N-(4-iodo(3-pyridyl))-2,2-dimethylpropanamide (43, Step b)

The reaction was performed according to a procedure in the literature (*J. Org. Chem.* 1988, 53, 2740-2744). A 3 L three-neck round-bottom flask was equipped with a mechanical stirrer, thermocouple, nitrogen inlet, and drying tube and placed in a cooling bath. The flask was charged with 2,2-dimethyl-N-(3-pyridyl)propanamide (42, 40 g), tetramethylethylenediamine (TMEDA, 84 mL) and THF (1400 mL), and stirring was initiated. The reaction mixture was cooled to −78° C. A suspension formed. n-BuLi (224 mL) was added over at least a 15 minute period at a rate to keep the temperature below −65° C. The reaction mixture was stirred continually at −78° C. for 15 minutes before being stirred for 2 h at −10° C. A yellow to white precipitate slowly developed. The reaction mixture was cooled back to −78° C. A solution of iodine (142 g) in THF (480 mL) was added over 30 minutes. The temperature increased from −78° C. to −65° C. The reaction mixture was stirred continually for 2 h at −78° C. The reaction mixture was continually stirred at −78° C. until the reaction was deemed complete, i.e., upon disappearance of 2,2-dimethyl-N-(3-pyridyl)propanamide (42). If reaction was not complete, it was stirred continually at −78° C. for additional 1 h then monitored again. The reaction was monitored by TLC (SiO$_2$, [7:3] EtOAc:Hept, UV, two developments) by partitioning an aliquot of the reaction mixture (~1 mL) between EtOAc (1 mL) and saturated ammonium chloride solution (3 mL), agitating, allowing the layers to separate, and spotting the organic layer. The starting material (2,2-dimethyl-N-(3-pyridyl)propanamide, 42) had an RF of 0.25, and the product (N-(4-iodo(3-pyridyl))-2,2-dimethylpropanamide, 43) had an RF of 0.33. Typically, the reaction conversion was ~80% to product based on TLC. Materials used to synthesize N-(4-iodo(3-pyridyl))-2,2-dimethylpropanamide (43) are shown in Table 34.

To isolate the product (N-(4-iodo(3-pyridyl))-2,2-dimethylpropanamide, 43), the reaction mixture was poured into a saturated (10%) NH$_4$Cl solution (100 mL). The mixture was extracted with ethyl acetate (2×500 mL). The combined organic layer was washed with a saturated (10%) sodium thiosulfate solution (2×100 mL) to remove excess iodine and brine (200 mL). The organic layer was dried over MgSO$_4$ and charcoal, filtered through glass fiber filter paper, and concentrated to dryness. The above crude material was purified by passing through a silica plug (4 g of SiO$_2$/1 g of crude mixture), and eluting the plug with 10-50% ethyl acetate in heptanes. All fractions that contained compound were combined and concentrated under reduced pressure at 45° C. to yield a beige solid. The solid was dried under vacuum at 25° C. for a minimum of 5 hours.

N-(4-iodo(3-pyridyl))-2,2-dimethylpropanamide (43, lot #1358-77-1) was a beige solid, synthesized with a yield of 48 g (70%). N-(4-iodo(3-pyridyl))-2,2-dimethylpropanamide (43) was analyzed using HPLC (MPP-LC1, 240 nm), and according to results, it was 95.9% pure. $^1$H-NMR (300 MHz, CDCl$_3$) was used to confirm the identity of N-(4-iodo(3-pyridyl))-2,2-dimethylpropanamide (43).

Synthesis of 4-iodo-3-pyridylamine (44, Step c)

The reaction was performed according to a procedure in the literature (*Tetrahedron Lett.* 2005, 46, 6363). A 1 L three-neck round-bottom flask was equipped with a mechanical stirrer, thermocouple, nitrogen inlet, and drying tube and placed in a heating mantle. The flask was charged with N-(4-iodo(3-pyridyl))-2,2-dimethylpropanamide (43, 45 g) and 25% sulfuric acid (270 mL). The solubility of starting material in 25% sulfuric acid was very high and formed light yellow clear solution. The reaction mixture was heated to 80° C. for 8 h. The reaction mixture was stirred continually at 80° C. until deemed to be complete, i.e., upon complete disappearance of starting material (N-(4-iodo(3-pyridyl))-2,2-dimethylpropanamide, 43). If reaction was not complete, stirring was continued at 80° C. for additional 6 h then monitored again, and repeated until complete. Typically, reaction was

TABLE 34

Materials used to synthesize N-(4-iodo(3-pyridyl))-2,2-dimethylpropanamide (43)

| Compound | MW (g/mol) | d (g/mL) | Equivalents | Amt/mol | Lot # |
|---|---|---|---|---|---|
| Reaction | | | | | |
| 2,2-Dimethyl-N-(3-pyridyl)propanamide | 178.23 | NA | 1.0 | 40 g/0.224 mol | 1358-74-1 |
| n-Buthyl lithium (2.5 M in hexanes) | 64.06 | 0.693 | 2.5 | 224 mL/0.561 mol | R10-3008-1 |
| N,N,N',N''-Tetramethyl-ethylenediamine (TMEDA) | 116.20 | 0.775 | 2.5 | 84 mL/0.561 mol | 11-2408-7 |
| Iodine | 253.81 | NA | 2.5 | 142 g/0.561 mol | R08-0207-7 |
| Tetrahydrofuran (THF) | 72.11 | 0.886 | 47 vol | 1880 mL | R03-2808-3 |
| Isolation | | | | | |
| Saturated (10%) ammonium chloride solution | NA | NA | 2.5 vol | 100 mL | R06-0808-4 |
| Saturated (10%) sodium thiosulphate solution | NA | NA | 5 vol | 200 mL | R07-1107-6 |
| Brine | NA | NA | 5 vol | 200 mL | R08-1208-9 | complete within 4-6 h. The reaction was monitored by TLC (SiO$_2$, 100% EtOAc, UV) by partitioning an aliquot of reaction mixture (~1 mL) between 50% NaOH solution (2 mL) and EtOAc (4 mL), agitating, allowing the layers to separate, and spotting the organic layer on TLC. The starting material (N-(4-iodo(3-pyridyl))-2,2-dimethylpropanamide, 43) had an RF of 0.55, and the product (4-iodo-3-pyridylamine, 44) had an RF of 0.35. Materials used to synthesize 4-iodo-3-pyridylamine (44) are shown in Table 35.

TABLE 35

Materials used to synthesize 4-iodo-3-pyridylamine (44)

| Compound | MW (g/mol) | d (g/mL) | Equivalents | Amt/mol | Lot # |
|---|---|---|---|---|---|
| Reaction | | | | | |
| N-(4-Iodo(3-pyridyl))-2,2-dimethylpropanamide | 304.13 | NA | 1.00 | 45 g/0.148 mol | 1358-77-1 |
| 25% Sulfuric acid | 98.01 | 1 | 6 vol | 270 mL | R01-1909-2 |
| Isolation | | | | | |
| 50% NaOH solution | NA | 1 | 1 vol | 45 g | 08-2208-1 |
| EtOAc | NA | 0.789 | 6.6 vol | 300 mL | R09-0508-2 |
| MTBE | NA | 0.741 | 1.2 vol | 60 mL | R10-2308-01 |

To isolate the product (4-iodo-3-pyridylamine, 44), the flask was cooled to −10° C. and the mixture was cautiously basified (pH 10-11) with 50% NaOH solution (45 g) while maintaining a temperature below 10° C. Additional ethyl acetate (200 mL) was added, the reaction was stirred for 10 minutes, and the layers were allowed to separate. The organic layer was collected, and the aqueous layer was extracted with ethyl acetate (2×50 mL). The combined organic layer was dried over MgSO$_4$ and charcoal, filtered through a glass fiber filter paper, and concentrated to dryness. The residue was diluted with MTBE (50 mL) and the solids were filtered, rinsing with MTBE (10 mL). The product was air-dried for 2 h and then dried under high vacuum at room temperature to constant weight.

4-Iodo-3-pyridylamine (44, lot #1358-86-1) was an off-white solid, synthesized with a yield of 24 g (75%). 4-Iodo-3-pyridylamine (44) was analyzed using HPLC (PLX-LC3, 220), and according to results, it was 100% pure. $^1$H-NMR (300 MHz, CDCl$_3$) was used to confirm the identity of 4-iodo-3-pyridylamine (44).

Synthesis of 4-(5-chloro-2-propoxy-4-pyridyl)-3-pyridyl amine (46, Step d)

A 1 L three-necked round-bottomed flask was equipped with a mechanical stirrer, thermometer, glass immersion tube for bubbling nitrogen, reflux condenser connected to a bubbler with silicone or mineral oil to monitor that a positive pressure of nitrogen was maintained in the reaction flask throughout the synthesis, and a heating mantle. The flask was charged with 3-amino-4-iodopyridine (44, 12.5 g), 5-chloro-2-propoxy-4-pyridinylboronic acid (45, 18.4 g), and dioxane (538 mL). Stirring was initiated. The resulting yellow solution was degassed by bubbling an intensive stream of nitrogen through the mixture for 10 minutes. Bubbling of nitrogen was maintained throughout the entire synthesis. A solution of K$_3$PO$_4$ (36.18 g) and water (175 mL) was charged. The resulting solution was degassed by bubbling an intensive stream of nitrogen through the mixture for 10 minutes. PdCl$_2$(PPh$_3$)$_2$ (4 g) was charged. The nitrogen flow was reduced, and the resulting orange color solution was heated to reflux (at approximately 95° C.) with bubbling of nitrogen. The reaction mixture was stirred at reflux for a minimum of 24 hours. The reaction mixture was continued to be stirred at 95° C. until the reaction was deemed to be complete, i.e., when <10% starting material was observed by TLC. If reaction was not complete, stirring was continued at 80° C. for an additional 6 h. Typically, reaction was complete within 24 h. The reaction was monitored by TLC (SiO$_2$, [5:95], MeOH:DCM: 2-3 drops of aqueous NH$_3$, UV, three developments) by spotting an aliquot of reaction mixture directly on a TLC plate at various time points. The starting material had an RF of 0.45, while the product had an RF of 0.5, which was a fluorescent spot. The materials used to synthesize 4-(5-Chloro-2-propoxy-4-pyridyl)-3-pyridyl amine (46) are shown in Table 36.

TABLE 36

Materials used to synthesize 4-(5-chloro-2-propoxy-4-pyridyl)-3-pyridyl amine (46)

| Compound | MW (g/mol) | d (g/mL) | Equivalents | Amt/mol | Lot # |
|---|---|---|---|---|---|
| Reaction | | | | | |
| 3-Amino-4-iodopyridine | 220.01 | NA | 1.00 | 12.5 g/0.058 | 1358-86-1 |
| 5-Chloro-2-propoxy-4-pyridinylboronic acid[1] | 215.45 | NA | 1.5 | 18.4 g/0.085 | 1357-100-1 |
| Potassium phosphate tri base (K$_3$PO$_4$) | 212.12 | NA | 3 | 36.18 g/0.17 | R07-0808-3 |

TABLE 36-continued

Materials used to synthesize 4-(5-chloro-2-propoxy-4-pyridyl)-3-pyridyl amine (46)

| Compound | MW (g/mol) | d (g/mL) | Equivalents | Amt/mol | Lot # |
|---|---|---|---|---|---|
| PdCl$_2$(PPh$_3$)$_2$ | 701.89 | NA | 0.1 | 4 g/0.0058 | R12-1907-57 |
| 1,4-Dioxane | NA | 1.034 | 43 vol | 538 mL | R03-3007-6 |
| Water | NA | 1 | 14 | 175 mL | RO water |
| Isolation | | | | | |
| Water | NA | 1 | 10 vol | 125 mL | RO water |
| EtOAc | NA | 0.789 | 40 vol | 500 mL | R09-0508-2 |

[1]This compound was not commercially available. It was prepared as reported in Example 2, the synthesis of 8-propoxypyridino [4',3'-5,4]pyrrolo[3,2-c]pyridine hydrochloride (2).

To isolate the product (4-(5-chloro-2-propoxy-4-pyridyl)-3-pyridyl amine, 46), the reaction mixture was cooled to 40° C. The reaction mixture was concentrated under reduced pressure at 40° C. to remove the majority of dioxane. The residue was diluted with water (125 mL) and EtOAc (300 mL), and the mixture was stirred at ambient temperature for 20 minutes. The reaction mixture was transferred to a separation funnel, the layers were allowed to separate, and the aqueous layer was extracted with EtOAc (2×100 mL). The organic layers were combined, washed with brine (200 mL), dried over MgSO$_4$ and charcoal, and filtered through a glass fiber filter. The filtrate was concentrated under vacuum to dryness (semi-solid, ~30 g). The crude semisolid was loaded on top of a silica plug (300 g) packed with DCM, using further DCM for loading. The column was eluted under gravity sequentially with DCM (1 L), 0.5% MeOH in DCM (0.5 L), 1% MeOH in DCM (0.5 L), and 1.5% MeOH in DCM (3 L) and collecting fractions of ~3 L. Increasing the methanol percentage in small increments helped facilitate effective purification. The column was eluted under gravity with 2% MeOH in DCM until complete removal of the clean product was observed by TLC analysis. All fractions containing clean product were combined and concentrated under reduced pressure to give an off-white solid.

4-(5-Chloro-2-propoxy-4-pyridyl)-3-pyridyl amine (46, lot #1458-20-1) was an off-white solid, synthesized with a yield of 7.6 g (51%). 4-(5-Chloro-2-propoxy-4-pyridyl)-3-pyridyl amine (46) was analyzed using HPLC (PLX-LC3, 220), and according to results, it was 96% pure. $^1$H-NMR (300 MHz, CDCl$_3$) was used to confirm the identity of 4-(5-chloro-2-propoxy-4-pyridyl)-3-pyridyl amine (46).

Synthesis of 3-propoxypyridino[4',3'-4,5]pyrrolo[2,3-c]pyridine (47, Step e)

A 500 mL sealed tube was charged with 4-(5-chloro-2-propoxy-4-pyridyl)-3-pyridyl amine (46, 5 g), dioxane (200 mL), Cs$_2$CO$_3$ (20.1 g), and water (7 mL). Stirring was initiated. The resulting yellow solution was degassed by bubbling an intensive stream of nitrogen through the mixture for 10 minutes. S—PHOS (1.56 g) was charged. The resulting solution was degassed by bubbling an intensive stream of nitrogen through the mixture for 10 minutes. Pd$_2$(dba)$_2$ (2.6 g) was charged. The resulting solution was degassed by bubbling an intensive stream of nitrogen through the mixture for 5 minutes. The tube was sealed. The reaction mixture was heated to approximately 95° C. at reflux for a minimum of 12 hours. Stirring of the reaction mixture was continued at 95° C. until it was deemed that the reaction was complete, i.e., when <15-20% of the starting material was observed by TLC. If the reaction was not complete, stirring was continued at 80° C. for an additional 6 h. Typically, the reaction was complete within 12 h. The reaction was monitored by TLC (SiO$_2$, [5:95], MeOH:DCM:2-3 drops of aqueous NH$_3$, UV, three developments) by spotting an aliquot of reaction mixture directly on TLC plate. The starting material had an RF of 0.5 (fluorescent spot), and the product had an RF of 0.45 (fluorescent spot). Materials used to synthesized 3-propoxypyridino[4',3'-4,5]pyrrolo[2,3-c]pyridine (47) are shown in Table 37.

TABLE 37

Materials used to synthesize 3-propoxypyridino[4',3'-4,5]pyrrolo[2,3-c]pyridine (47)

| Compound | MW (g/mol) | d (g/mL) | Equivalents | Amt/mol | Lot # |
|---|---|---|---|---|---|
| Reaction | | | | | |
| 4-(5-Chloro-2-propoxy-4-pyridyl)-3-pyridyl amine | 263.73 | NA | 1.00 | 5 g/0.019 | 1358-86-1 |
| Cesium carbonate (Cs$_2$CO$_3$) | 325.82 | NA | 3 | 20.1 g/ 0.057 | |
| Tris(dibenzylideneacetone)palladium (Pd$_2$(dba)$_3$) | 915.7 | NA | 0.15 | 2.6 g/ 0.0028 | R06-1808-01 |
| 2-Dicyclohexylphosphino-2',6'-dimethoxybiphenyl (S-PHOS) | 410.53 | NA | 0.2 | 1.56 g/ 0.0038 | R10-0506-53 |
| 1,4-Dioxane | NA | 1.034 | 40 vol | 200 mL | R03-3007-6 |
| Water | NA | 1 | 1.4 | 7 mL | RO water |

TABLE 37-continued

Materials used to synthesize 3-propoxypyridino[4',3'-4,5]pyrrolo[2,3-c]pyridine (47)

| Compound | MW (g/mol) | d (g/mL) | Equivalents | Amt/mol | Lot # |
|---|---|---|---|---|---|
| Isolation | | | | | |
| Water | NA | 1 | 20 vol | 100 mL | RO water |
| EtOAc | NA | 0.895 | 80 vol | 400 mL | R07-0808-4 |

To isolate the product (3-propoxypyridino[4',3'-4,5]pyrrolo[2,3-c]pyridine, 47), the reaction mixture was cooled to 40° C. The reaction mixture was concentrated under reduced pressure at 40° C. to remove the majority of dioxane. The residue was diluted with water (100 mL) and EtOAc (200 mL), and the mixture was stirred at ambient temperature for 20 minutes. The reaction mixture was transferred to an appropriate separation funnel, the layers were allowed to separate, and the aqueous layer was extracted with EtOAc (2×100 mL). The organic layers were combined, washed with brine (100 mL), dried over MgSO$_4$ and charcoal, and filtered through a glass fiber filter. The filtrate was concentrated under vacuum to dryness (~5 g). The crude semisolid was loaded on top of a silica plug (50 g) packed with DCM, using further DCM for loading. The column was eluted under gravity sequentially with DCM (0.5 L), 0.5% MeOH in DCM (0.5 L), 1% MeOH in DCM (0.5 L), and 1.5% MeOH in DCM (3 L), collecting fractions of ~3 L. Increasing the methanol percentage in small increments helped facilitate effective purification. The column was eluted under gravity with 3% MeOH in DCM until complete removal of the clean product was observed by TLC analysis. All fractions containing clean product were combined and concentrated under reduced pressure to give an off-white solid.

3-Propoxypyridino[4',3'-4,5]pyrrolo[2,3-c]pyridine (47, lot #1458-36-1) was a light yellow solid, synthesized with a yield of 2.6 g (60%). 3-Propoxypyridino[4',3'-4,5]pyrrolo[2,3-c]pyridine (47) was analyzed using HPLC (LIL-LC4, 2230), and according to results, it was 99.9% pure. $^1$H-NMR (300 MHz, CDCl$_3$) was used to confirm the identity of 3-propoxypyridino[4',3'-4,5]pyrrolo[2,3-c]pyridine (47).

Synthesis of 3-propoxypyridino[4',3'-4,5]pyrrolo[2,3-c]pyridine hydrochloride (4, Step f)

A 100 mL three-necked round-bottomed flask was equipped with a magnetic bead, thermocouple, nitrogen inlet, and drying tube and placed in a cooling bath. The flask was charged with 3-propoxypyridino[4',3'-4,5]pyrrolo[2,3-c]pyridine (47, 1.2 g) and ether (30 mL). Stirring was initiated. A suspension formed. HCl in ether (2 M solution, 3.43 mL) was added slowly over 5 minutes. A mild exotherm was observed, with the temperature increasing from 18.0° C. to 19.4° C. The reaction mixture was continued to be stirred at room temperature for a minimum of 6 hours. No procedure was available to monitor the reaction, so the reaction was continued for a minimum of 6 hours, assuming that reaction was complete. Materials used to synthesize 3-propoxypyridino[4',3'-4,5]pyrrolo[2,3-c]pyridine hydrochloride (4) are shown in Table 38.

TABLE 38

Materials used to synthesize 3-propoxypyridino[4',3'-4,5]pyrrolo[2,3-c]pyridine hydrochloride (4)

| Compound | MW (g/mol) | d (g/mL) | Equivalents | Amt/mol | Lot # |
|---|---|---|---|---|---|
| Reaction | | | | | |
| 3-Propoxypyridino[4',3'-4,5]pyrrolo[2,3-c]pyridine | 227.27 | NA | 1.0 | 1.2 g/5.28 | 1458-36-1 |
| HCl in ether (2 M solution) | 36.5 | 1 | 1.3 | 3.43 mL/ 6.86 | R01-2609-01 |
| Ether | | 1 | 25 vol | 30 mL | NA |
| Isolation | | | | | |
| Ether | | 1 | 10 vol | 12 mL | NA |

To isolate the product (3-propoxypyridino[4',3'-4,5]pyrrolo[2,3-c]pyridine hydrochloride, 4), the reaction mixture was cooled to 0° C. The solids were filtered, the cake was washed with ether (12 mL), and the solids were dried under N$_2$ atmosphere for approximately 3 h until constant weight.

3-Propoxypyridino[4',3'-4,5]pyrrolo[2,3-c]pyridine hydrochloride (4, lot #1458-45-1) was a yellow solid, synthesized with a yield of 1.25 g (90%). 3-Propoxypyridino[4',3'-4,5]pyrrolo[2,3-c]pyridine hydrochloride (4) was analyzed using HPLC (LIL-LC4, 2230), and according to results, it was 99% pure. LC-MS and $^1$H-NMR (300 MHz, DMSO-$d_6$) were used to confirm the identity of 3-propoxypyridino[4',3'-4,5]pyrrolo[2,3-c]pyridine hydrochloride (4).

Reference Example 1

Psychoactive Drug Screening Program (PDSP)

Primary and secondary radioligand binding assays are performed. In general, the primary assay is run at very high ligand (compound) concentration as a broad screen to determine whether a compound binds to a particular receptor. If greater than 50% inhibition at 10 μM (high concentration of compound) at a particular receptor is determined, a secondary assay is performed on that receptor. Data from the secondary assay is the binding affinity ($K_i$ value). Ki values indicating selective binding of a compound to a receptor are generally less than 10 nM.

Primary Radioligand Binding Assay

A solution of the compound to be tested is prepared as a 1 mg/ml stock in Standard Binding Buffer or dimethyl sulfoxide (DMSO) according to its solubility. A similar stock of a reference compound (positive control) is also prepared. Eleven dilutions (5× assay concentration) of the test and reference (reference compounds are presented in Table 19) compounds are prepared in Standard Binding Buffer (buffer compositions are presented in Table 20) by serial dilution: 0.05 nM, 0.5 nM, 1.5 nM, 5 nM, 15 nM, 50 nM, 150 nM, 500 nM, 1.5 µM, 5 µM, 50 µM (thus, the corresponding assay concentrations span from 10 µM to 10 µM and include semi-log points in the range where high-to-moderate affinity ligands compete with radioligand for binding sites).

Figure 11:
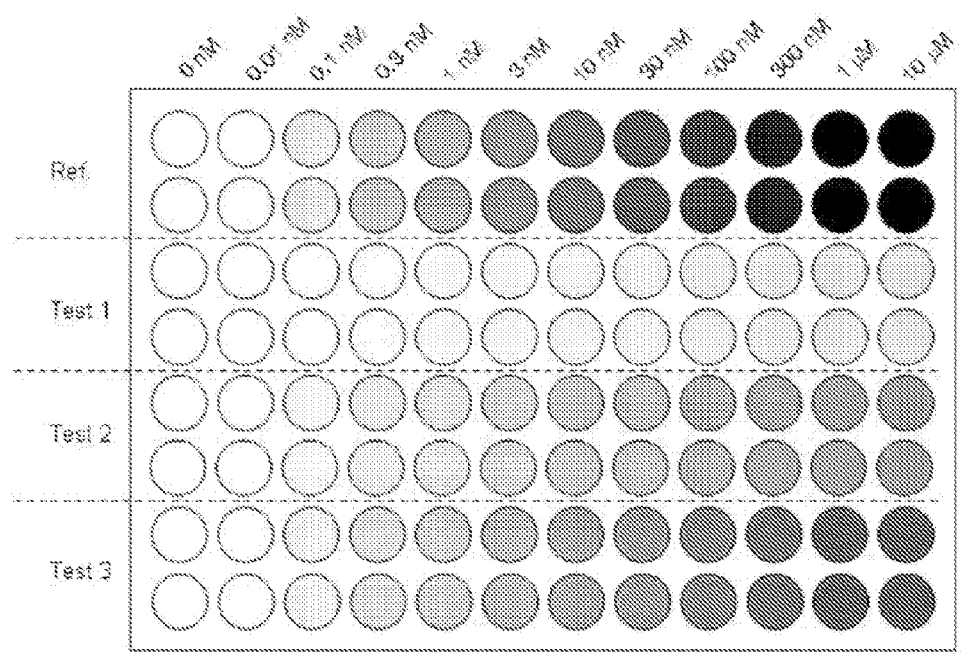
FIG. 11 is a schematic diagram of a binding assay plate for a radioligand binding assay.

Radioligand (radioligands are presented in Table 39) is diluted to five times the assay concentration (assay concentrations are presented in Table 39) in Standard Binding Buffer. Typically, the assay concentration of radioligand is a value between one half the KD and the KD of a particular radioligand at its target. Aliquots (50 µL) of radioligand are dispensed into the wells of a 96-well plate (see FIG. 11) containing 100 µL of Standard Binding Buffer (Table 40). Then, duplicate 50 µL aliquots of the test and reference compound dilutions are added (see FIG. 11). According to FIG. 11, increasing concentrations (from left to right) of reference or test compound (diluted in buffer) are added (50 µL aliquots, in duplicate) from 5× stock solutions to wells containing 50 µL of 5× radioligand (fixed concentration, prepared in buffer) and 100 µL of buffer. Finally, 50 µL of receptor-containing membrane homogenate (5× suspension in buffer) are added to achieve a final assay volume of 250 µL. Final concentrations of reference or test compound are listed above the columns in FIG. 11.

TABLE 39

Assay conditions for primary radioligand binding assays.

| RECEPTOR | RADIOLIGAND (ASSAY CONC.) | REFERENCE | ASSAY BUFFER |
|---|---|---|---|
| 5-HT1A | [$^3$H]8-OH-DPAT (O.5 nM) | Methysergide | Standard Binding Buffer |
| 5-HT1B | [$^3$H]GR127543 (0.3 nM) | Ergotamine | Standard Binding Buffer |
| 5-HT1D | [$^3$H]GR127543 (0.3 nM) | Ergotamine | Standard Binding Buffer |
| 5-HT1E | [$^3$H]5-HT (3 nM) | 5-HT | Standard Binding Buffer |
| 5-HT2A | [$^3$H]Ketanserin (0.5 nM) | Chlorpromazine | Standard Binding Buffer |
| 5-HT2B | [$^3$H]LSD (1 nM) | Methysergide | Standard Binding Buffer |
| 5-HT3 | [$^3$H]Mesulergine (0.5 nM) | Chlorpromazine | Standard Binding Buffer |
| 5-HT5a | [$^3$H]LSD (1 nM | Ergotamine | Standard Binding Buffer |
| 5-HT6 | [$^3$H]LSD (1 nM) | Chlorpromazine | Standard Binding Buffer |
| 5-HT7 | [$^3$H]LSD (1 nM) | Chlorpromazine | Standard Binding Buffer |
| D1 | [$^3$H]SCH233930 (0.2 nM) | SKF38393 | Dopamine Binding Buffer |
| D2 | [$^3$H]N-methylspiperone (0.2 nM) | Haloperidol | Dopamine Binding Buffer |
| D3 | [$^3$H]N-methylspiperone (0.2 nM) | Chlorpromazine | Dopamine Binding Buffer |
| D4 | [$^3$H]N-methylspiperone (0.3 nM) | Chlorpromazine | Dopamine Binding Buffer |
| D5 | [$^3$H]SCH233930 (0.2 nM) | SKF38393 | Dopamine Binding Buffer |
| Delta OR | [$^3$H]DADLE (0.3 nM) | Naltrindole | Standard Binding Buffer |
| Kappa OR | [$^3$H]U69593 (0.3 nM) | Salvinorin A | Standard Binding Buffer |
| Mu OR | [$^3$H]DAMGO (0.3 nM) | DAMGO | Standard Binding Buffer |
| H1 | [$^3$H]Pyrilamine (0.9 nM) | Chlorpheniramine | Histamine Binding Buffer |
| H2 | [$^3$H]Tiotidine (3 nM) | Cimetidine | Histamine Binding Buffer |
| H3 | [$^3$H]alpha-methylhistamine (0.4 nM) | Histamine | Histamine Binding Buffer |
| H4 | [$^3$H]Histamine (5 nM) | Clozapine | Histamine Binding Buffer |
| SERT | [$^3$H]Citalopram (0.5 nM) | Amitriptyline | Transporter Binding Buffer |
| NET | [$^3$H]Nisoxetine (0.5 nM) | Desipramine | Transporter Binding Buffer |
| DAT | [$^3$H]WIN35428 (0.5 nM) | GBR12909 | Transporter Binding Buffer |

TABLE 39-continued

Assay conditions for primary radioligand binding assays.

| RECEPTOR | RADIOLIGAND (ASSAY CONC.) | REFERENCE | ASSAY BUFFER |
|---|---|---|---|
| V1 | [$^3$H]Vasopressin (1 nM) | Vasopressin | Vasopressin Binding Buffer |
| V2 | [$^3$H]Vasopressin (1 nM) | Vasopressin | Vasopressin Binding Buffer |
| V3 | [$^3$H]Vasopressin (1 nM) | Vasopressin | Vasopressin Binding Buffer |
| EP3 | [$^3$H]PGE2 (10 nM) | EP2 | Prostaglandin Binding Buffer |
| EP4 | [$^3$H]PG32 (10 nM) | EP2 | Prostaglandin Binding Buffer |
| PKCalpha | [$^3$H]PDBU (3 nM) | PDBU | PKC Binding Buffer |
| PKCbeta | [$^3$H]PDBU (3 nM) | PDBU | PKC Binding Buffer |
| PKCgamma | [$^3$H]PDBU (3 nM) | PDBU | PKC Binding Buffer |
| PKCdelta | [$^3$H]PDBU (3 nM) | PDBU | PKC Binding Buffer |
| PKCepsilon | [$^3$H]PDBU (3 nM) | PDBU | PKC Binding Buffer |
| A1 | [$^3$H]NECA (5 nM) | NECA | Adenosine Binding Buffer |
| A2 | [$^3$H]NECA (10 nM) | NECA | Adenosine Binding Buffer |
| VMAT2 | [$^3$H]Tetrabenezine (1.5 nM) | Reserpine | VMAT Binding Buffer |
| GABAA | [$^3$H]Muscimol (1 nM) | GABA | 50 mM Tris Acetate, pH 7.4 |
| GABAB | [$^3$H]Baclofen (20 nM) | GABA | 50 mM Tris Acetate, pH 7.4 |
| PBR | [$^3$H]PK11195 (1 nM) | PK11195 | 50 mM Tris HCl, pH 7.4 |
| AMPA | [$^3$H]AMPA (1 nM) | Glutamic Acid | 50 mM Tris HCl, 2.5 mM CaCl$_2$, pH 7.4 |
| BZP | [$^3$H]Flunitrazepam (0.5 nM) | Diazepam | 50 mM Tris HCl, 2.5 mM CaCl$_2$, pH 7.4 |
| Kainate | [$^3$H]Kainic Acid | Glutamic Acid | 50 mM Tris HCl, 2.5 mM CaCl$_2$, pH 7.4 |
| Na Channel | [$^3$H]Batrachotoxin | Veratridine | Na Channel Buffer |
| NMDA | [$^3$H]MK801 (1 nM) | MK801 | 5 mM Tris, pH 7.4 |
| Oxytocin | [$^3$H]Oxytocin | Oxytocin | Oxytocin Binding Buffer |
| Alpha1A | [$^3$H]Prazosin (0.7 nM) | Urapidil | Alpha1 Binding Buffer |
| Alpha1B | [$^3$H]Prazosin (9.7 nM) | Corynanthine | Alpha1 Binding Buffer |
| Alpha2A | [$^3$H]Clonidine (1 nM) | Oxymetazolline | Alpha2 Binding Buffer |
| Alpha2B | [$^3$H]Clonidine (1 nM) | Prazosin | Alpha2 Binding Buffer |
| Alpha2C | [$^3$H]Clonidine (1 nM) | Prazosin | Alpha2 Binding Buffer |
| Beta1 | [$^{125}$H]Iodopindolol (0.1 nM) | Atenolol | Beta Binding Buffer |
| Beta2 | [$^{125}$H]Iodopindolol (9.1 nM) | ICI118551 | Beta Binding Buffer |
| Beta3 | [$^{125}$H]Iodopindolol (0.1 nM) | ICI118551 | Beta Binding Buffer |
| M1 | [$^3$H]QNB (0.5 nM) | Atropine | Muscarinic Binding Buffer |
| M2 | [$^3$H]QNB (0.5 nM) | Atropine | Muscarinic Binding Buffer |
| M3 | [$^3$H]QNB (0.5 nM) | Atropine | Muscarinic Binding Buffer |
| M4 | [$^3$H]QNB (0.5 nM) | Atropine | Muscarinic Binding Buffer |
| M5 | [$^3$H]QNB (0.5 nM) | Atropine | Muscarinic Binding Buffer |
| Alpha2Beta 2 | [$^3$H]Epibatidine (0.5 nM) | (−)-Nicotine | 50 mM Tris HCl, pH 7.4 |
| Alpha2Beta4 | [$^3$H]Epibatidine (0.5 nM) | (−)-Nicotine | 50 mM Tris HCl, pH 7.4 |
| Alpha3Beta2 | [$^3$H]Epibatidine (0.5 nM) | (−)-Nicotine | 50 mM Tris HCl, pH 7.4 |
| Alpha3Beta4 | [$^3$H]Epibatidine (0.5 nM) | (−)-Nicotine | 50 mM Tris HCl, pH 7.4 |
| Alpha4Beta2 | [$^3$H]Epibatidine (0.5 nM) | (−)-Nicotine | 50 mM Tris HCl, pH 7.4 |
| Alpha4Beta4 | [$^3$H]Epibatidine (0.5 nM) | (−)-Nicotine | 50 mM Tris HCl, pH 7.4 |

TABLE 39-continued

Assay conditions for primary radioligand binding assays.

| RECEPTOR | RADIOLIGAND (ASSAY CONC.) | REFERENCE | ASSAY BUFFER |
|---|---|---|---|
| Alpha4Beta2 (endog.) | [$^3$H]Epibatidine (0.5 nM) | (−)-Nicotine | 50 mM Tris HCl, pH 7.4 |
| CB1 | [$^3$H]CP55940 | CP55940 | Cannabinoid Binding Buffer |
| CB2 | [$^3$H]CP55940 | CP55940 | Cannabinoid Binding Buffer |
| Sigma1 | [$^3$H]Pentazocine (3 nM) | Haloperidol | Sigma Binding Buffer |
| Sigma2 | [$^3$H]DTG (3 nM) | Haloperidol | Sigma Binding Buffer |
| AT1 | [$^{125}$I]ATII (0.1 nM) | Candesartan | Angiotensin Binding Buffer |
| AT2 | [$^{125}$I]ATII (0.1 nM) | PD123319 | Angiotensin Binding Buffer |
| Ca++ Channel | [$^3$H]Nitrendipine (0.1 nM) | Nifendipine | Calcium Channel Buffer |
| Imidazoline1 | [$^{125}$I]Clonidine (0.1 nM) | Naphazoline | Imidazoline Binding Buffer |
| NT1 | [$^3$H]Neurotensin (2 nM) | Neurotensin | 50 mM Tris HCl, 0.2% BSA, pH 7.4 |
| NT2 | [$^3$H]Neurotensin (2 nM) | Neurotensin | 50 mM Tris HCl, 0.2% BSA, pH 7.4 |

TABLE 40

Buffer compositions for primary radioligand binding assays

| BUFFER | COMPOSITION |
|---|---|
| Standard Binding Buffer | 50 nM Tris HCl, 10 mM MgCl$_2$, 0.1 mM EDTA, pH 7.4 |
| Dopamine Binding Buffer | 50 mM HEPES, 50 mM NaCl, 5 mM MgCl$_2$, 0.5 mM EDTA, pH 7.4 |
| Histamine Binding Buffer | 50 mM Tris HCl, 0.5 mM EDTA, pH 7.4 |
| Transporter Binding Buffer | 50 mM Tris HCl, 150 mM NaCl, 5 mM KCl, pH 7.4 |
| Vasopressin Binding Buffer | 20 mM Tris HCl, 100 mM NaCl, 10 mM MgCl$_2$, 0.1 mg/ml bacitracin, 1 mg/ml BSA, pH 7.4 |
| Prostaglandin Binding Buffer | 25 mM Tris HCl, 10 mM MgCl$_2$, 1 mM EDTA, pH 7.4 |
| PKC Binding Buffer | 50 mM Tris HCl, 1 mM CaCl$_2$, 4 mg/ml BSA, 100 µg/ml phosphatidylserine, pH 7.4 |
| Adensoine Binding Buffer | 50 mM Tris HCl, 1 U/ml adenosine deaminase, pH 7.4 |
| VMAT Binding Buffer | 50 mM HEPES, 300 mM sucrose, pH 8.0 |
| Na Channel Buffer | 130 mM choline chloride, 5.4 mM KCl, 0.8 MgSO$_4$, 5.5 mM glucose, 50 mM HEPES, 1 µM tetrodotoxin, 1 mg/ml BSA, 30 µg/well scorpion venom, pH 7.4 at 37 degrees centigrade |
| Oxytocin Binding Buffer | 50 mM HEPES, 10 mM MnCl$_2$, pH 7.4 |
| Alpha1 Binding Buffer | 20 mM Tris HCl, 145 mM NaCl, pH 7.4 |
| Alpha2 Binding Buffer | 50 mM Tris HCl, 5 mM MgCl$_2$, pH 7.7 |
| Beta Binding Buffer | 50 mM Tris HCl, 3 mM MnCl$_2$, pH 7.7 |
| Muscarinic Binding Buffer | 50 mM Tris HCl, pH 7.7 |
| Cannabinoid Binding Buffer | 50 mM Tris HCl, 1 mM EDTA, 3 mM MgCl$_2$, 5 mg/ml fatty acid-free BSA, pH 7.4 |
| Sigma Binding Buffer | 50 mM Tris HCl, pH 8.0 |
| Angiotensin Binding Buffer | 50 mM Tris HCl, 5 mM MgCl$_2$, 150 mM NaCl, 0.5 mg/ml BSA, 100 mM bacitracin, protease inhibitor, pH 7.4 |
| Calcium Channel Buffer | 50 mM Tris HCl, 50 mM NaCl, 1 mM CaCl$_2$, pH 7.4 |
| Imidazoline Binding Buffer | 5 mM Tris HCl, 5 mM HEPES, 0.5 mM EGTA, 0.5 mM EDTA, 0.5 mM MgCl$_2$, pH 8.0 |

Finally, crude membrane fractions of cells expressing recombinant target (prepared from 10 cm plates by harvesting phosphate buffered saline (PBS)-rinsed monolayers, resuspending and lysing in chilled, hypotonic 50 mM Tris-HCl, pH 7.4, centrifuging at 20,000×g, decanting the supernatant and storing at −80° C.; typically, one 10 cm plate provides sufficient material for 24 wells) are resuspended in 3 mL of chilled Standard Binding Buffer and homogenized by several passages through a 26 gauge needle, and then 50 µL are dispensed into each well.

The 250 µL reactions are incubated at room temperature and shielded from light (to prevent photolysis of light-sensitive ligands) for 1.5 hours, then harvested by rapid filtration onto Whatman GF/B glass fiber filters pre-soaked with 0.3% polyethyleneimine using a 96-well Brandel harvester. Four rapid 500 µL washes are performed with chilled Standard Binding Buffer to reduce non-specific binding. Filters are placed in 6 mL scintillation tubes and allowed to dry overnight. The next day, 4 mL of EcoScint scintillation cocktail (National Diagnostics) are added to each tube. The tubes are capped, labeled, and counted by liquid scintillation counting.

For higher throughput assays, bound radioactivity is harvested onto 0.3% polyethyleneimine-treated, 96-well filter mats using a 96-well Filtermate harvester. The filter mats are dried, then scintillant is melted onto the filters, and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y = \text{bottom} + [(\text{top} - \text{bottom})/(1 + 10^{x - \log IC_{50}})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the $K_i$ by applying the Cheng-Prusoff approximation:

$$K_i = IC_{50}/(1 + [\text{ligand}]/K_D)$$

where [ligand] equals the assay radioligand concentration and $K_D$ equals the affinity constant of the radioligand for the target receptor.

Secondary Radioligand Binding Assay

This assay is used to test binding to receptors such as the serotonin receptors: $5\text{-HT}_{1A}$, $5\text{-HT}_{1B}$, $5\text{-HT}_{1D}$, $5\text{-HT}_{1E}$, $5\text{-HT}_{2A}$, $5\text{-HT}_{2B}$, $5\text{-HT}_{2C}$, $5\text{-HT}_{3}$, $5\text{-HT}_{5A}$, $5\text{-HT}_{6}$ and $5\text{-HT}_{7}$. The protocol is adapted from Roth et al. *J. Pharmacol. Exp. Ther.* 1986, 238, 480-485 and Roth et al. *J. Pharmacol. Exp. Ther.* 1994, 268, 1403-1410. The assay buffer is Standard Binding Buffer (50 mM Tris-HCl, 10 mM $MgCl_2$, 0.1 mM EDTA, pH 7.4). The membrane fraction source is transiently or stably transfected cell lines (e.g., HEK293, COS, CHO, NIH3T3).

A solution of the compound to be tested is prepared as a 1 mg/mL stock in Standard Binding Buffer or DMSO according to its solubility. A similar stock of a reference compound (positive control) is also prepared. Eleven dilutions (5× assay concentration) of the test and reference (see Table 41) compounds are prepared in Standard Binding Buffer by serial dilution: 0.05 nM, 0.5 nM, 1.5 nM, 5 nM, 15 nM, 50 nM, 150 nM, 500 nM, 1.5 μM, 5 μM, 50 μM (thus, the corresponding assay concentrations span from 10 pM to 10 μM and include semilog points in the range where high-to-moderate affinity ligands compete with radioligand for binding sites).

Radioligand (see Table 41) is diluted to five times the assay concentration (see Table 21) in Standard Binding Buffer. Typically, the assay concentration of radioligand is a value between one half the $K_D$ and the $K_D$ of a particular radioligand at its target. Aliquots (50 μL) of radioligand are dispensed into the wells of a 96-well plate (see FIG. 11) containing 100 μL of Standard Binding Buffer. Then, duplicate 50 μL aliquots of the test and reference compound dilutions are added (see FIG. 11).

TABLE 41

Radioligands, radioligands assay concentrations, and reference compounds for secondary radioligand binding assay

| RECEPTOR | RADIOLIGAND (ASSAY CONC.) | REFERENCE COMPOUND |
|---|---|---|
| $5\text{-HT}_{1A}$ | [$^3$H]8-OH-DPAT (0.5 nM) | Methysergide |
| $5\text{-HT}_{1B}$ | [$^3$H]GR125743 (0.3 nM) | Ergotamine |
| $5\text{-HT}_{1D}$ | [$^3$H]GR125743 (0.3 nM) | Ergotamine |
| $5\text{-HT}_{1E}$ | [$^3$H]5-HT (3 nM) | 5-HT |
| $5\text{-HT}_{2A}$ | [$^3$H]Ketanserine (0.5 nM) | Chlorpromazine |
| $5\text{-HT}_{2B}$ | [$^3$H]LSD (1 nM) | 5-HT |
| $5\text{-HT}_{2C}$ | [$^3$H]Mesulergine (0.5 nM) | Chlorpromazine |
| $5\text{-HT}_{3}$ | [$^3$H]LY278584 (0.3 nM) | LY278584 |
| $5\text{-HT}_{5A}$ | [$^3$H]LSD (1 nM) | Ergotamine |
| $5\text{-HT}_{6}$ | [$^3$H]LSD (1 nM) | Chlorpromazine |
| $5\text{-HT}_{7}$ | [$^3$H]LSD (1 nM) | Chlorpromazine |

Finally, crude membrane fractions of cells expressing recombinant target (prepared from 10-cm plates by harvesting PBS-rinsed monolayers, resuspending and lysing in chilled, hypotonic 50 mM Tris-HCl, pH 7.4, centrifuging at 20,000×g, decanting the supernatant and storing at −80° C.; typically, one 10 cm plate provides sufficient material for 24 wells) are resuspended in 3 mL of chilled Standard Binding Buffer and homogenized by several passages through a 26 gauge needle, and then 50 μL are dispensed into each well.

The 250 μL reactions are incubated at room temperature and shielded from light (to prevent photolysis of light-sensitive ligands) for 1.5 hours, then harvested by rapid filtration onto Whatman GF/B glass fiber filters pre-soaked with 0.3% polyethyleneimine using a 96-well Brandel harvester. Four rapid 500 μL washes are performed with chilled Standard Binding Buffer to reduce non-specific binding. Filters are placed in 6 mL scintillation tubes and allowed to dry overnight. The next day, 4 mL of EcoScint scintillation cocktail (National Diagnostics) are added to each tube. The tubes are capped, labeled, and counted by liquid scintillation counting. For higher throughput assays, bound radioactivity is harvested onto 0.3% polyethyleneimine-treated, 96-well filter mats using a 96-well Filtermate harvester. The filter mats are dried, then scintillant is melted onto the filters, and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in Prism 4.0 (GraphPad Software) using the built-in three parameter logistic model describing ligand competition binding to radioligand-labeled sites:

$$y = \text{bottom} + [(\text{top} - \text{bottom})/(1 + 10^{x - \log IC_{50}})]$$

where bottom equals the residual radioligand binding measured in the presence of 10 μM reference compound (i.e., non-specific binding) and top equals the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$K_i = IC_{50}/(1 + [\text{ligand}]/K_D)$$

where [ligand] equals the assay radioligand concentration and $K_D$ equals the affinity constant of the radioligand for the target receptor.

Example 5

Psychoactive Drug Screening Program (PDSP) Analysis of 8-Propoxypyridino[4,3'-5,4]pyrrolo[3,2-c]pyridine hydrochloride (2) and 3-Propoxy pyridino[4',3'-4,5]pyrrolo[2,3-c]pyridine hydrochloride (4)

8-Propoxypyridino[4',3'-5,4]pyrrolo[3,2-c]pyridine hydrochloride (2) and 3-propoxy pyridino[4',3'-4,5]pyrrolo[2,3-c]pyridine hydrochloride (4) were tested for binding to receptors according to Reference Example 1. Results are presented in Table 42, where data represent mean percentage inhibition (with n=4 determinations) for the compound tested at receptor subtypes. Data shown in Table 42 are results from primary assays, except numbers in parentheses are the $K_i$ values in nM as determined from secondary assays. Significant inhibition was considered to be >50% in primary assays. Where negative inhibition (−) was seen, it represented a stimulation of binding, as in some cases, compounds at high concentration non-specifically increase binding. The concentration of compound in primary assays was 10 μM.

8-Propoxypyridino[4',3'-5,4]pyrrolo[3,2-c]pyridine hydrochloride (2) demonstrated <50% binding at 10 μM in primary receptor binding assays, i.e., the compounds did not bind to the receptor, at the following receptors: Serotonin 5ht1a (human); Serotonin 5ht1b (human); Serotonin 5ht5a (human); Serotonin 5ht6 (human); Serotonin 5ht7 (human); Adrenergic Beta1 (human); Dopamine D1 (human); Dopamine D3 (rat); Dopamine D5 (human); Opiate DOR; Histamine H1 (human); Histamine H2 (human); Histamine H3 (human); Opiate KOR; Muscarinic (acetylcholine) M3 (human); and Opiate MOR. 8-Propoxypyridino[4',3'-5,4]pyrrolo[3,2-c]pyridine hydrochloride (2) demonstrated >50% binding at 10 μM in primary receptor binding assays at the Dopamine D2 (human) and Dopamine D4 (human) receptors, so secondary assay binding data was determined for these two receptors. The $K_i$ for binding of compound 2 at Dopamine D2 (human) and Dopamine D4 (human) receptors was found to be >10,000 nM and 7,503 nM, respectively, which indicated that compound 2 does not significantly bind these receptors.

3-Propoxy pyridino[4',3'-4,5]pyrrolo[2,3-c]pyridine hydrochloride (4) demonstrated <50% binding at 10 μM in primary receptor binding assays, i.e., the compounds did not bind to the receptor, at the following receptors: Serotonin 5ht1a (human); Serotonin 5ht1b (human); Serotonin 5ht3 (human); Serotonin 5ht5a (human); Serotonin 5ht6 (human); Serotonin 5ht7 (human); Adrenergic Beta1 (human); Dopamine D1 (human); Dopamine D5 (human); Opiate DOR; Histamine H1 (human); Histamine H2 (human); Histamine H3 (human); Histamine H4 (human); Opiate KOR; Muscarinic (acetylcholine) M3 (human); Opiate MOR; NET transporter; and SERT transporter. 3-Propoxy pyridino[4',3'-4,5]pyrrolo[2,3-c]pyridine hydrochloride (4) demonstrated >50% binding at 10 μM in primary receptor binding assays at the Dopamine D2 (human) receptor, so secondary assay binding data was determined for this receptor. The $K_i$ for binding of compound 4 at Dopamine D2 (human) receptor was found to be >10,000 nM, which indicated that compound 4 does not significantly bind this receptor.

TABLE 42

Results of Psychoactive Drug Screening Program (PDSP) Analysis of 8-propoxypyridino[4',3'-5,4]pyrrolo[3,2-c]pyridine hydrochloride (2) and 3-propoxy pyridino[4',3'-4,5]pyrrolo[2,3-c]pyridine hydrochloride (4)

| RECEPTOR[a] | COMPOUND 2 | COMPOUND 4 |
|---|---|---|
| Adrenergic receptor Beta1 | 3.2 | 3.5 |
| Dopamine receptor D1 | −8.8 | −14 |
| Dopamine receptor D2 | (>10,000)[b] | 50 (>10,000)[b] |
| Dopamine receptor D3 | 31.8 | 24.1 |
| Dopamine receptor D4 | (7,503)[b] | −18.1 |
| Opiate receptor DOR | 13.6 | 10 |
| Histamine receptor H1 | 17.1 | 9.3 |
| Histamine receptor H2 | 31.4 | 26.8 |
| Histamine receptor H3 | 21 | 11.3 |
| Histamine receptor H4 |  | 4.9 |
| Opiate receptor KOR | −10.2 | −6.1 |
| Opiate receptor MOR | 5.6 | 1.2 |
| Muscarinic receptor M3 | 15.6 | 2.4 |
| Serotonin receptor 5ht1a | 6.1 | 16.4 |
| Serotonin receptor 5ht1b | 47 | 4.1 |
| Serotonin receptor 5ht3 |  | 20.7 |
| Serotonin receptor 5ht5a | 15 | 8.3 |
| Serotonin receptor 5ht6 | 10.4 | 15.3 |
| Serotonin receptor 5ht7 | 6.4 | −12.1 |
| NET transporter |  | 36.8 |
| SERT transporter | 22.1 | 17.6 |

[a]Based on the primary (and secondary, if determined) binding assays, compounds 2 and 4 did not significantly bind to the receptors shown here.
[b]Secondary binding assay was performed, with the number in parentheses being the $K_i$ value in nM.

Example 6

Psychoactive Drug Screening Program (PDSP) Analysis of tert-Butyl pyridine[4',5'-4,5]pyrrolo[3,2-c]pyridine-8-carboxylate (1) and tert-Butyl pyridine[4',5'-5,4]pyrrolo[2,3-c]pyridine-3-carboxylate (3)

tert-Butyl pyridine[4',5'-4,5]pyrrolo[3,2-c]pyridine-8-carboxylate (1) and tert-butyl pyridine[4',5'-5,4]pyrrolo[2,3-c]pyridine-3-carboxylate (3) are tested for binding to receptors as described in Reference Example 1 and are shown to bind to $GABA_A$ receptor.

Reference Example 2

Competition Binding Assays

Competition binding assays are performed as described in Choudhary, M. S. et al. Mol. Pharmacol. 1992, 42, 627-633. Competition binding assay are performed in a total volume of 0.5 mL at 4° C. for 1 hour using [$^3$H]flunitrazepam as the radiolabelled ligand. A total of 6 μg of cloned human $GABA_A$ receptor DNA containing desired α subtype along with β2 and γ2 subunits are used for transfecting HEKT cell line using Fugene 6 (Roche Diagnostic) transfecting reagent. Cells are harvested 48 hrs after transfection, washed with Tris~Cl buffer (pH 7.0) and Tris~Acetate buffer (pH 7.4), and the resulting pellets are stored at −80° C. until assayed. On the day of the assay, pellets containing 20-50 μg of $GABA_A$ receptor protein are resuspended in 50 mM Tris-acetate pH 7.4 at 4° C. and incubated with the radiolabel as previously described (Choudhary et al., 1992). Nonspecific binding is defined as radioactivity bound in the presence of 100 μM compound and represents less than 20% of total binding. Membranes are harvested with a Brandel cell harvester followed by three ice-cold washes onto polyethyleneimine-pretreated (0.3%) Whatman GF/C filters. Filters are dried overnight and then soaked in Ecoscint A liquid scintillation cocktail (National Diagnostics; Atlanta, Ga.). Bound radioactivity is quantified by liquid scintillation counting. Membrane protein concentrations are determined using an assay kit from Bio-Rad (Hercules, Calif.) with bovine serum albumin as the standard.

Example 7

Competition Binding Assay Analysis of Compounds (2), (3) and (4)

8-Propoxypyridino[4',3'-5,4]pyrrolo[3,2-c]pyridine hydrochloride (2), tert-butyl pyridine[4',5'-5,4]pyrrolo[2,3-c] pyridine-3-carboxylate (3) and 3-propoxy pyridino[4',3'-4,5] pyrrolo[2,3-c]pyridine hydrochloride (4) were tested for binding to the BzR/GABAa-ergic receptors as detailed in Reference Example 2. As shown in Table 43, the compounds bind potently at the BzR/GABAa-ergic receptors.

TABLE 43

Results of Competition Binding Assay Analysis of Compounds (2), (3) and (4)

| Compound | $GABA_A$ RECEPTOR BINDING (nM) | | | |
|---|---|---|---|---|
| | $\alpha 1$ | $\alpha 2$ | $\alpha 3$ | $\alpha 5$ |
| 2 | 9.861 | 0.33 | 4.04 | 12.21 |
| 3 | 2.9 | 2.5 | 3.4 | 3.7 |
| 4 | 5.785 | 6.308 | 1.49 | 43.06 |

Example 8

Competition Binding Assay Analysis of tert-Butyl pyridine[4',5'-4,5]pyrrolo[3,2-c]pyridine-8-carboxylate (1)

Tert-butyl pyridine[4',5'-4,5]pyrrolo[3,2-c]pyridine-8-carboxylate (1) is tested for binding to the BzR/GABAa-ergic receptors as described in Reference Example 2, and results indicate the compound potently binds to the BzR/GABAa-ergic receptors.

Reference Example 3

Analysis of the In Vivo Effects

Electrophysiological Experiments $GABA_A$ receptor subunits $\alpha 1$, $\alpha 3$, and $\alpha 2$ are cloned into pCDM8 expression vectors (Invitrogen, CA) as been described elsewhere (Fuchs et al. *Eur. J. Pharmacol.* 1995, 289, 87-95). cDNAs for subunits $\alpha 2$, $\alpha 3$ and $\alpha 5$ are subcloned into pCI-vector. After linearizing the cDNA vectors with appropriate restriction endonucleases, capped transcripts are produced using the mMessage mMachine T7 transcription kit (Ambion, Tex.). The capped transcripts are polyadenylated using yeast poly(A) polymerase (USB, OH) and are diluted and stored in diethylpyrocarbonate-treated water at −70° C.

The methods used for isolating, culturing, injecting and defolliculating of the oocytes are identical as described previously (Sigel, E. *J. Physiol.* 1987, 386, 73-90; Sigel, E. et al. *Neuron* 1990, 5, 703-711.). Briefly, mature female *Xenopus laevis* (Nasco, Wis.) are anaesthetized in a bath of ice-cold 0.17% Tricain (Ethyl-m-aminobenzoate, Sigma, Mo.) before decapitation and removal of the frogs ovary. Stage 5 to 6 oocytes with the follicle cell layer around them are singled out of the ovary using a platinum wire loop. Oocytes are stored and incubated at 18° C. in modified Barths' Medium (MB, containing 88 mM NaCl, 10 mM HEPES-NaOH (pH 7.4), 2.4 mM $NaHCO_3$, 1 mM KCl, 0.82 mM $MgSO_4$, 0.41 mM $CaCl_2$, 0.34 mM $Ca(NO_3)_2$) that is supplemented with 100 U/mL penicillin and 100 µg/mL streptomycin. Oocytes with follicle cell layers still around them are injected with a total of 2.25 ng of cRNA. cRNA ratio used is 1:1:5 for the $\alpha$ subunits, $\beta 3$, and $\gamma 2$, respectively. After injection of cRNA, oocytes are incubated for at least 36 hours before the enveloping follicle cell layers are removed. To this end, oocytes are incubated for 20 min at 37° C. in MB that contains 1 mg/mL collagenase type IA and 0.1 mg/ml trypsin inhibitor I-S (both Sigma). This is followed by osmotic shrinkage of the oocytes in doubly concentrated MB medium supplied with 4 mM Na-EGTA and manually removing the follicle cell layer. After peeling off the follicle cell layer, the cells are allowed to recover overnight before being used in electrophysiological experiments.

For electrophysiological recordings, oocytes are placed on a nylon-grid in a bath of *Xenopus* Ringer solution (XR, containing 90 mM NaCl, 5 mM HEPES-NaOH (pH 7.4), 1 mM $MgCl_2$, 1 mM KCl and 1 mM $CaCl_2$). The oocytes are constantly washed by a flow of 6 mL/min XR which can be switched to XR containing GABA and/or the compounds. The compounds are diluted into XR from DMSO-solutions resulting in a final concentration of 0.1% DMSO perfusing the oocytes. Compounds are preapplied for 30 sec before the addition of GABA, which is coapplied with the drugs until a peak response is observed. Between two applications, oocytes are washed in XR for up to 15 min to ensure full recovery from desensitization. For measurements the oocytes are impaled with two microelectrodes (2-3 mΩ) which are filled with 2 mM KCl. All recordings are performed at room temperature at a holding potential of −60 mV using a Warner OC-725C two-electrode voltage clamp (Warner Instruments, Hamden, Conn.). Data are digitized, recorded, and measured using a Digidata 1322A data acquisition system (Axon Instruments, Union City, Calif.). Results of concentration response experiments are graphed using GraphPad Prism 4.00 (GraphPad Software, San Diego, Calif.). Data are graphed as mean±SEM of at least four oocytes from at least two batches.

Behavioral Experiments

Experiments are carried out on male Wistar rats (Military Farm, Belgrade, Serbia), weighing 220-250 g. All procedures in the study conform to EEC Directive 86/609 and are approved by the Ethical Committee on Animal Experimentation of the Faculty of Pharmacy in Belgrade. The rats are housed in transparent plastic cages, six animals per cage, and have free access to food pellets and tap water. The temperature of the animal room is 22±1° C., the relative humidity 40-70%, the illumination 120 lux, and the 12/12 h light/dark period (light on at 6:00 h). All handling and testing takes place during the light phase of the diurnal cycle. Separate groups of animals are used for three behavioral paradigms. The behavior is recorded by a ceiling-mounted camera and analyzed by the ANY-maze Video Tracking System software (Stoelting Co., Wood Dale, Ill., USA). The compounds are dissolved/ suspended with the aid of sonication in a solvent containing 85% distilled water, 14% propylene glycol, and 1% Tween 80, and are administered intraperitoneally in a volume of 2 ml/mL, 20 min before behavioral testing.

Measurement of Locomotor Activity

Twenty minutes after receiving the appropriate treatment, single rats are placed in a clear Plexiglas chamber (40×25×35 cm). Activity under dim red light (20 lux) is recorded for a total of 30 min or 45 min, without any habituation period, using ANY-maze software. Besides the total distance traveled, behavior is analyzed by dividing the locomotor activity data into 5-min bins. For purposes of improving data analysis, the central 20% of the chamber (200 cm$^2$) may be virtually set as a central zone. An entry into a zone is counted when 70% of the animal's body has crossed the zone border. An exit from the zone is counted when more than 50% of the animal's body has left the zone.

Locomotor influences of a compound dosed for example, at 30 mg/kg, are assessed in comparison with a reference compound. The dose response curve for the compound (for example, at 0; 2.5; 5; 10; 20 and 40 mg/kg) is determined. Examples of this characterization of other compounds may be found in Savić, M. M. et al. Brain Res. 2008, 1208, 150-159, which is incorporated by reference herein.

Behavior in the Elevated Plus Maze

The apparatus is constructed of sheet metal, with a black rubber floor. It consists of a maze elevated to a height of 50 cm with two open (50×10 cm) and two enclosed arms (50×10×40 cm), connected by a junction area (central platform) measuring 10×10 cm. A ledge of sheet metal (0.3 cm high) surrounding the open arms is added. The illumination in the experimental room consists of one red neon tube fixed on the ceiling, giving light intensity of 10 lux on the surface of the closed arms. At the beginning of the experiment, single rats are placed in the center of the maze, facing one of the enclosed arms, and their behavior is recorded for 5 min. An entry into an open or closed arm is scored when 90% of the animal crossed the virtual line separating the central square of the maze from the arm, whereas an exit occurs when more than 90% of the animal left the respective arm. After each trial, the maze is cleaned with dry and wet towels. The dose response curve for the compound is determined. Examples of this dose response curve characterization of other compounds may be found in Savić, M. M. et al. Brain Res. 2008, 1208, 150-159, which is incorporated by reference herein.

Behavior in the Morris Water Maze

The water maze consists of a black cylindrical pool (diameter: 200 cm, height: 60 cm), with a uniform inner surface. The pool is filled to a height of 30 cm with 23° C. (±1° C.) water. The escape platform made of black plastic (15×10 cm) is submerged 2 cm below the water surface. The platform is made invisible to rats by having it painted the same color as the pool wall. There are many distal cues in the testing room (doors, pipes on the walls and the ceiling, cupboards). An indirect illumination in the experimental room is provided by white neon tubes fixed on the walls near the pool.

The rats receive the appropriate treatment 20 min before a swimming block, each day for 5 consecutive days of spatial acquisition. Each block consists of 4 trials, lasting a maximum time of 120 s, the inter-trial interval being 60 s. For each trial the rat is placed in the water facing the pool at one of four pseudorandomly determined starting positions. As during spatial learning the platform is hidden in the middle of the NE quadrant, the four distal start locations are chosen: S, W, NW and SE. Once the rat finds and mounts the escape, it is permitted to remain on the platform for 15 s. The rat is guided to the platform by the experimenter if it does not locate the escape within 120 s. To assess the long-term spatial memory at the end of learning, a probe trial for 60 s, with the platform omitted, is given 24 h after the last acquisition day. The probe trial, starting from the novel, most distant SW location, is performed without any pre-treatment. The tracking software virtually divides the pool into four quadrants, three concentric annuli and a target region consisting of the intersection of the platform quadrant and the platform (middle) annulus. The central annulus is set up to 10% of the whole area; the platform annulus equals 40%, whereas the area of the peripheral annulus is 50% of the whole.

Dependent variables chosen for tracking during the acquisition trials are: latency to platform (time from start to goal), total distance swam (path length), average swim speed and path efficiency (the ratio of the shortest possible path length to actual path length). All these indices are, to a lesser or greater degree, related to goal-directed behavior, i.e. spatial learning. As thigmotaxis (the tendency to swim or float near the pool wall) represents a factor which accounts for much of the variance in the water maze performance, and normally weakens during consecutive trials, the persistence of the thigmotaxis in the target (NE) quadrant is quantified. The loss of thigmotaxis is related to the procedural component of acquisition, and the percent of the distance swum in the target region (away from the wall) of the target quadrant may be seen as a measure of procedural learning. The indices of memory, assessed during the probe trial, include the distance and time in the platform (target) quadrant, platform ring and target region, as well as the number of entries and distance swum in the area where the platform used to be during training. In addition, the distance swum during 60 sec in the probe trial is taken as a measure of overall activity, while peripheral ring parameters (distance and time) are connected to the thigmotaxic behavior. The dose-response curve for the compound at various dosages is determined.

Statistical Analysis

All numerical data will be given as the mean±SEM. For electrophysiological data Student's t-test is used. Data from the activity assay and elevated plus maze are assessed by a one-way ANOVA, whereas the results from the water maze test are analyzed using a two-way ANOVA with repeated measures. Where applicable, Student-Newman-Keuls or Dunnett's test (post hoc comparisons) and analysis of covariance are also used. Statistical analyses are performed with ANY-maze Video Tracking System software (Stoelting Co., Wood Dale, Ill., USA).

Reference Example 4

Effect of Compounds on Excessive Alcohol Consumption

Subjects

Male P rats are used as subjects. All animals are individually housed in shoebox cages in a temperature- and humidity-controlled room on a 12 h:12 h light/dark cycle (lights on at 8:00 AM, off at 8:00 PM) with food and water available ad libitum. All behavioral training and testing take place between 8:00 AM and 10:00 AM. All procedures are conducted in accordance with the NIH Guide for the Care and Use of Laboratory Animals.

Systemic Drug Administration and Oral Solutions

Figure 12:
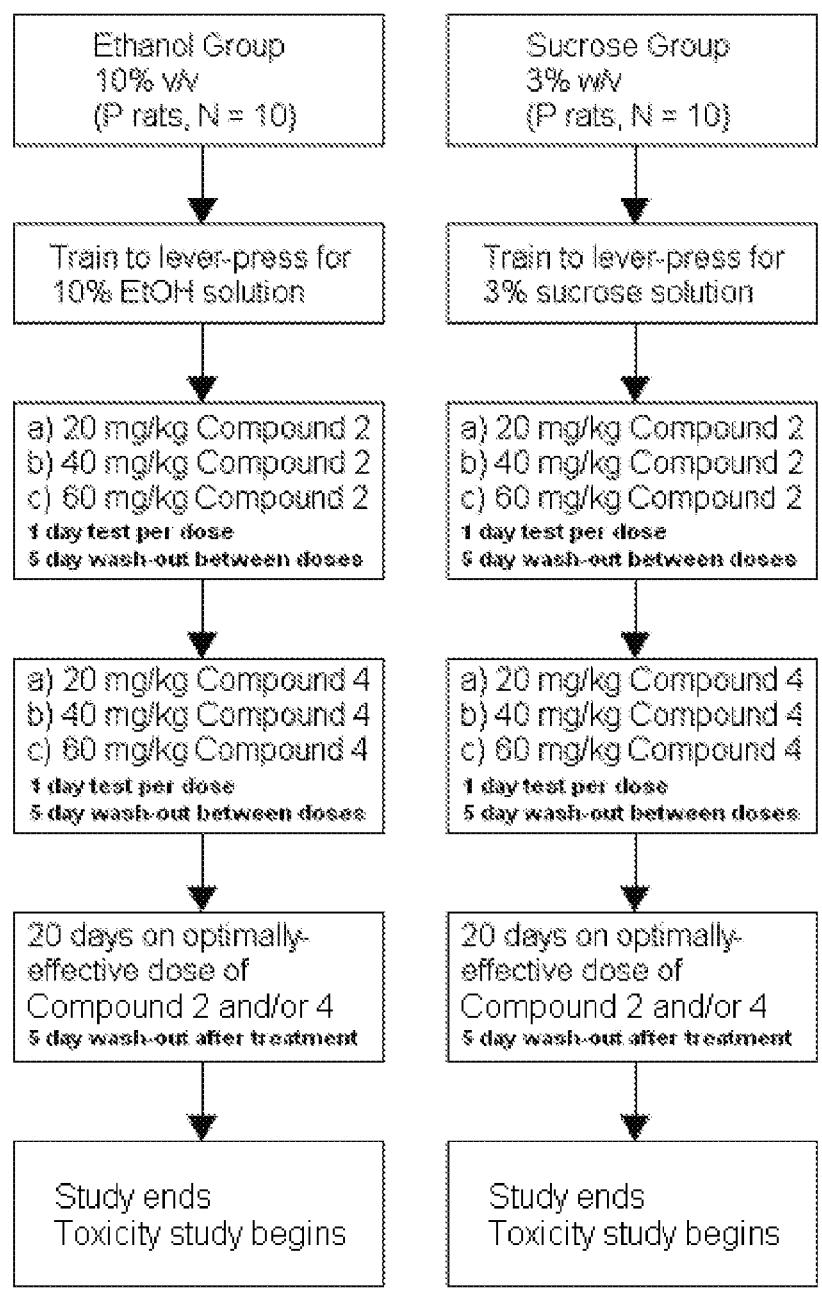
FIG. 12 is a schematic diagram of administration of compounds according to the invention by oral gavage for an animal model of excessive alcohol consumption.

10% (v/v) EtOH and 3% (w/v) sucrose solutions are prepared using previously published procedures (Harvey et al. J. Neurosci. 2002, 22, 3765-3775; June et al. Neuropsychopharmacology 2003, 28, 2124-2137) with deionized water. The solutions are prepared daily. Compounds are administered by oral gavage (20-60 mg/kg) in all studies (e.g., alcohol responding, sucrose responding) as indicated in FIG. 12. The compounds are mixed in deionized water and administered by gavage in an injection volume of 1 mL/kg 25 min prior to the behavioral task.

Animal Model of Excessive Alcohol Consumption

To initiate excessive "binge" alcohol drinking, a multiple-scheduled-access protocol is employed (Bell et al. Addict Biol. 2006, 11, 270-288, which is incorporated by reference herein) with P rats. First, the procedure entails adapting 20 P rats to a 12 h:12 h light/dark cycle which begins at 8:00 AM (lights on) and lasts to 8:00 PM (lights off). Beginning at 8:00 AM, one cohort of rats (N=10) are placed in the operant chamber for 30 min and presented with 10% (v/v) alcohol on both levers. After the initial 30 min session has elapsed, rats are then placed in the home cage with food and water ad libitum for 1 h. Rats then receive two additional 30 min alcohol access periods, spaced 1 h apart. In total, animals receive three 30 min access periods spaced 1 h apart across the cycle. Using this protocol, the P rats are expected to produce consistent blood alcohol concentration (BACs of approximately 144±22 mg %), while the HAD rats in the homecage procedure are expected to produce consistent BACs of approximately 158±15 mg %. Fluid deprivation is performed during the initiation period (1-2 days); this is discontinued after 1-2 days of successful lever pressing. Another cohort of rats (N=10) is trained in a similar manner; however, they lever press for a 3% (w/v) sucrose concentration. The sucrose control rats allow for evaluation of reinforcer specificity following administration of a compound. The duration of the binge period is 21 days, and responding is expected to increase over the 3 week period from 280 lever presses per 90 min to 500-750 lever presses per 90 min. BAC levels are taken immediately after the first two 30 min sessions every third day over the 21 day period. Data is collected every day of the 21 day period.

Behavioral testing is conducted in 20 standard operant chambers (Coulbourn Instruments, Allentown, Pa.), each equipped with two removable levers and two dipper fluid delivery systems enclosed in sound-attenuated cubicles as previously described (Harvey et al., *J. Neurosci.* 2002, 22, 3765-3775).

To ensure that animals are consuming pharmacologically-relevant amounts of alcohol during the binge operant sessions, BACs are collected in all animals on days that they do not receive drug treatment. Approximately 100 µL of whole blood is collected from a rat's tail tip into a heparin-coated microsample tube. The BAC samples are collected at select time points, depending on the experimental protocol. After collection, the whole blood is immediately centrifuged for 5 min at 1100 rpm. The results are calculated in units of mg/dL and printed within 20 s of each trial as previously reported (Harvey et al., *J. Neurosci.* 2002, 22, 3765-3775; June et al. *Neuropsychopharmacology* 2003, 28, 2124-2137). Measures are collected during the 2nd and 3rd week in the protocol after the 2nd 30 min session.

Compounds are tested for ability to effectively attenuate excessive/heavy alcohol drinking in binge-inducing models using the P rat. Separate cohorts of P rats (n=10/dosage group) undergo training for either the binge alcohol or sucrose drinking protocols. A power analysis reveals that this sample size is quite sufficient to detect independent variable manipulation for binge drinking. Following dose-response studies (for example, at 20, 40, and 60 mg/kg per compound) of each compound, the most effective dose (assuming efficacy) of the compound on binge alcohol drinking is tested for chronic treatment over a 20 day period as noted above. Efficacy is operationally defined as an agent which selectively reduces alcohol responding by >30% with little if any reduction (i.e., >than 10%) of a 3% sucrose concentration.

Data from the operant self-administration is analyzed using between-group analysis of variance (ANOVA) to determine the effects of the compounds on EtOH or sucrose responding. Any significant ANOVA is further analyzed by the use of an appropriate post-hoc test.

Example 9

Compounds 2 and 4 Reduce Excessive Alcohol Consumption

Figure 13:
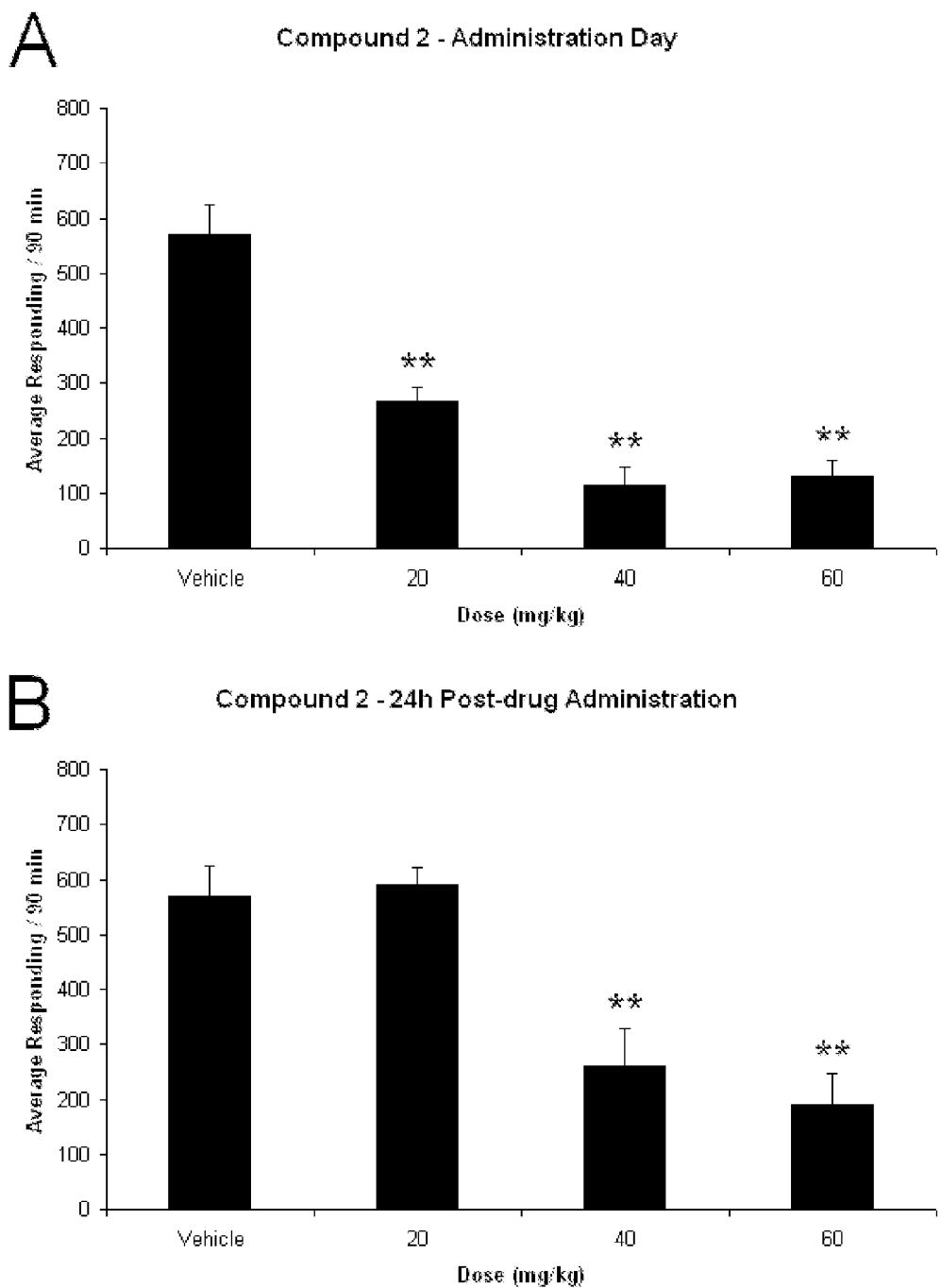
FIG. 13 is a graph of dose versus average responding, showing the effect of compound 2 on excessive alcohol consumption.
Figure 14:
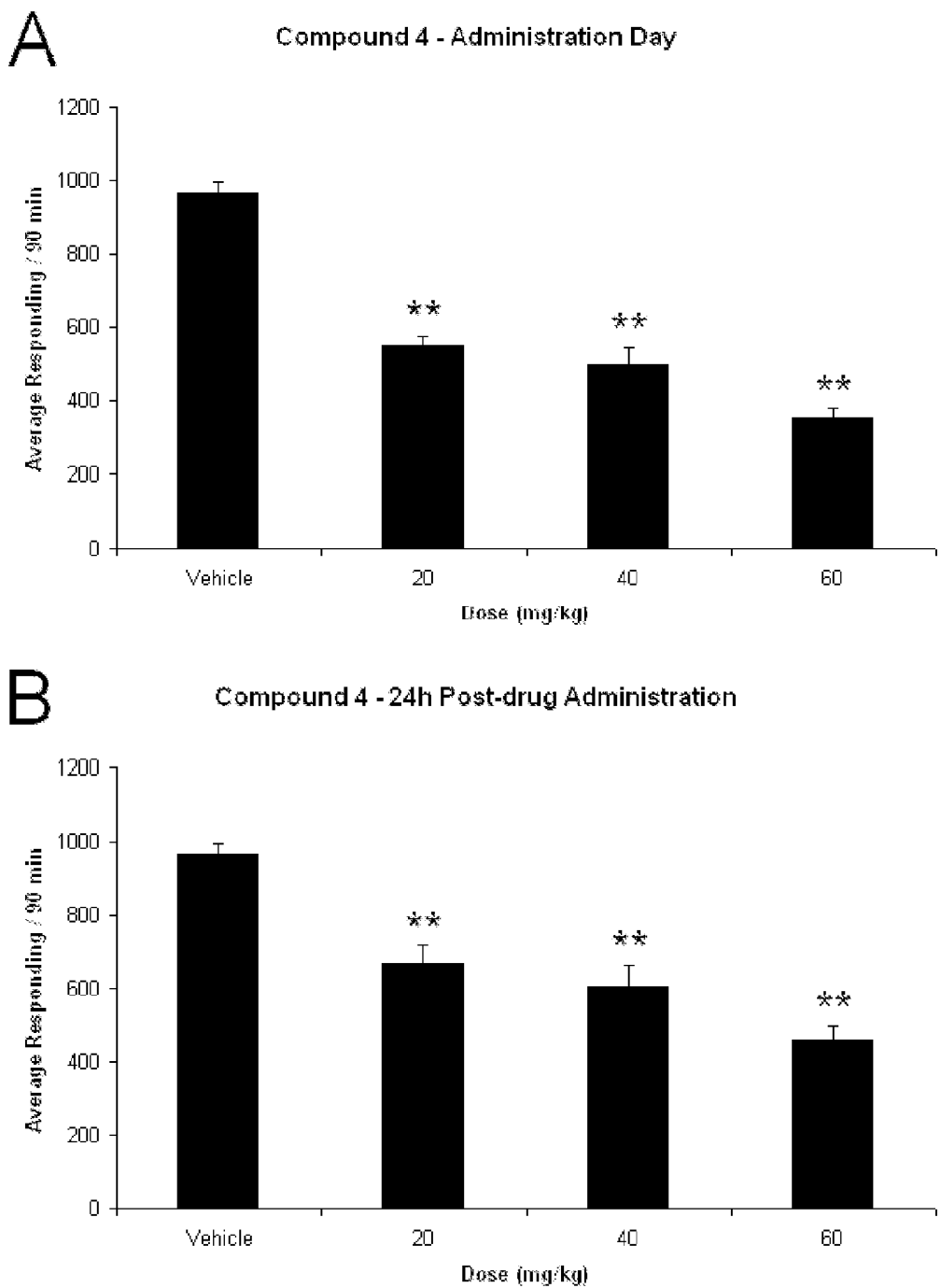
FIG. 14 is a graph of dose versus average responding, showing the effect of compound 4 on excessive alcohol consumption.

Compounds 2 and 4 were tested for their effect on excessive alcohol consumption as described in Example 10. Male P rats [N=5 per compound] were trained to lever press for alcohol under the excessive binge alcohol drinking model. Each cohort of rats received an oral gavage administration of compound 2 or 4, with at least 5 days in between for washout periods. Results for compound 2 are shown in FIG. 13, and results for compound 4 are shown in FIG. 14. The compounds remained effective in reducing excessive alcohol consumption 24 hr after compound administration.

The present invention is not limited to the embodiments specifically described above, but is capable of variation and modification without departure from the scope of the appended claims.

The invention claimed is:
1. A compound according to Formula (I):

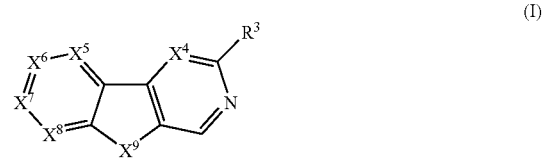

(I)

or isomers, or salts thereof;
wherein $X^4$, $X^5$, and $X^8$ are CH, $X^6$ may be N, $^+NR^6$ or $CR^6$, and $X^7$ may be N, $^+NR^6$ or $CR^7$, and wherein either $X^6$ or $X^7$ is N;
wherein $X^9$ is NH;
wherein $R^3$ is $CO_2R$, or $OR^1$ or COR;
wherein $R^6$ and $R^7$ are independently H, X, —C≡$CR^2$, lower alkyl, lower alkenyl, or lower alkynyl;
wherein R is —$C(CH_3)_{3-n}(CF_3)_n$, —$C(CH_3)_{3-r}(CH_{3-p}X_p)_r$, —$CH(CH_3)_{2-m}(CF_3)_m$, or —$CH(CH_3)_{2-t}(CH_{3-p}X_p)_t$;
wherein $R^1$ is —$CH_2CH_2CH_3$, —$CH(CH_3)_2$, —$CH_2CH_2CH_2CH_3$, —$CH_2CH(CH_3)_2$, —$CH(CH_3)$ $CH_2CH_3$, —$CH_2CH_2CH_2CH_2CH_3$, —$CH_2CH_2CH(CH_3)_2$, —$CH_2CH(CH_3)CH_2CH_3$, or —$CH(CH_3)CH_2CH_2CH_3$, wherein any of the hydrogens of $R^1$ may be replaced by X;
wherein $R^2$ is H, lower alkyl, $Me_3Si$, $Et_3Si$, n-$Pr_3Si$, or i-$Pr_3Si$;
wherein n is an integer from 0 to 3, m is an integer from 0 to 2, r is an integer from 1 to 3, p is an integer from 1 to 2, and t is an integer from 0 to 2; and
wherein X is independently selected from F, Cl, Br and I.
2. A compound according to claim 1, wherein $X^6$ is N.
3. A compound according to claim 2, wherein $X^7$ is CH.
4. A compound according to claim 1, wherein $X^7$ is N.
5. A compound according to claim 4, wherein $X^6$ is CH.
6. A compound according to claim 1, wherein $R^3$ is $CO_2R$.
7. A compound according to claim 6, wherein R is —$C(CH_3)_3$.
8. A compound according to claim 1, wherein $R^3$ is $OR^1$.
9. A compound according to claim 8, wherein $R^1$ is —$CH_2CH_2CH_3$.
10. A compound according to claim 1, wherein $X^4$ is CH, $X^5$ is CH, $X^6$ is N, $X^7$ is CH, $X^9$ is CH, $X^9$ is NH, and $R^1$ is —$CO_2C(CH_3)_3$.

11. A compound according to claim 1, wherein $X^4$ is CH, $X^5$ is CH, $X^6$ is N, $X^7$ is CH, $X^9$ is CH, $X^9$ is NH, and $R^1$ is —OCH$_2$CH$_2$CH$_3$.

12. A compound according to claim 1, wherein $X^4$ is CH, $X^5$ is CH, $X^6$ is CH, $X^7$ is N, $X^9$ is CH, $X^9$ is NH, and $R^1$ is —CO$_2$C(CH$_3$)$_3$.

13. A compound according to claim 1, wherein $X^4$ is CH, $X^5$ is CH, $X^6$ is CH, $X^7$ is N, $X^9$ is CH, $X^9$ is NH, and $R^1$ is —OCH$_2$CH$_2$CH$_3$.

14. A pharmaceutical composition comprising a compound according to claim 1 and a carrier.

15. The composition according to claim 14, further comprising an additional active agent.

16. The composition according to claim 15, wherein the additional active agent is an anxiolytic.

17. The composition according to claim 15, wherein the additional active agent treats a chemical addiction.

18. The composition according to claim 15, wherein the additional active agent is selected from the group consisting of diazepam, clonazepam, clorazepate, alprazolam, buspirone, meprobamate, naltrexone, naltrexone hydrochloride, disulfuram, nalmefene, metadoxine, acamposate calcium, and chlordiazepoxide hydrochloride.

* * * * *

UNITED STATES PATENT AND TRADEMARK OFFICE
CERTIFICATE OF CORRECTION

| | | |
|---|---|---|
| PATENT NO. | : 8,268,854 B2 | |
| APPLICATION NO. | : 12/471019 | |
| DATED | : September 18, 2012 | |
| INVENTOR(S) | : James M. Cook et al. | |

It is certified that error appears in the above-identified patent and that said Letters Patent is hereby corrected as shown below:

In the Specification

Column 1, line 15     Replace:
[[This invention was made with US Government support awarded by the National Institute of Mental Health (NIMH), Grant No. MH 46851. The United States as certain rights in this invention.]]

with:
--This invention was made with government support under MH 46851 awarded by the National Institutes of Health (NIH). The government has certain rights in the invention.--

Signed and Sealed this
Fourteenth Day of April, 2015

Michelle K. Lee
*Director of the United States Patent and Trademark Office*